(12) United States Patent
Shaaltiel et al.

(10) Patent No.: US 10,000,551 B2
(45) Date of Patent: Jun. 19, 2018

(54) CHIMERIC POLYPEPTIDES, POLYNUCLEOTIDES ENCODING SAME, CELLS EXPRESSING SAME AND METHODS OF PRODUCING SAME

(71) Applicant: Protalix Ltd., Carmiel (IL)

(72) Inventors: Yoseph Shaaltiel, Timrat (IL); Uri Hanania, Carmiel (IL); Tali Kizhner, Yishuv Atzmon-Segev (IL); Tami Ariel, Misgav (IL); Svetlana Gingis-Velitski, Kiryat-Motzkin (IL); Myriam Golembo, Moshav Netaim (IL)

(73) Assignee: Protalix Ltd., Carmiel (IL)

( * ) Notice: Subject to any disclaimer, the term of this patent is extended or adjusted under 35 U.S.C. 154(b) by 0 days. days.

(21) Appl. No.: 14/849,963

(22) Filed: Sep. 10, 2015

(65) Prior Publication Data

US 2016/0075754 A1 Mar. 17, 2016

Related U.S. Application Data

(60) Provisional application No. 62/048,932, filed on Sep. 11, 2014.

(51) Int. Cl.
*A61K 39/00* (2006.01)
*C07K 14/705* (2006.01)
*A61K 38/17* (2006.01)
*A61K 36/00* (2006.01)

(52) U.S. Cl.
CPC .... *C07K 14/70578* (2013.01); *A61K 38/1793* (2013.01); *A61K 36/00* (2013.01); *C07K 2319/02* (2013.01); *C07K 2319/30* (2013.01)

(58) Field of Classification Search
None
See application file for complete search history.

(56) References Cited

U.S. PATENT DOCUMENTS

| | | |
|---|---|---|
| 6,391,638 B1 | 5/2002 | Shaaltiel |
| 7,648,702 B2 | 1/2010 | Gombotz et al. |
| 7,901,905 B2 | 3/2011 | Frazer |
| 7,915,225 B2 | 3/2011 | Finck |
| 7,951,557 B2 | 5/2011 | Shaaltiel et al. |
| 8,007,790 B2 | 8/2011 | Li et al. |
| 8,102,229 B2 | 1/2012 | Simon et al. |
| 8,119,605 B2 | 2/2012 | Finck |
| 2003/0084482 A1 | 5/2003 | Hall et al. |
| 2003/0135887 A1 | 7/2003 | Brandle et al. |
| 2004/0072805 A1 | 4/2004 | Warren et al. |
| 2004/0220103 A1 | 11/2004 | Finck et al. |
| 2006/0204487 A1 | 9/2006 | Shaaltiel et al. |
| 2007/0243185 A1 | 10/2007 | Gombotz et al. |
| 2008/0038232 A1 | 2/2008 | Shaaltiel et al. |
| 2008/0122294 A1 | 5/2008 | Simon et al. |
| 2008/0269123 A1 | 10/2008 | Li et al. |
| 2011/0142832 A1 | 6/2011 | Finck |
| 2014/0286986 A1 | 9/2014 | Matoba et al. |

FOREIGN PATENT DOCUMENTS

| | | |
|---|---|---|
| WO | WO 99/67401 | 12/1999 |
| WO | WO 02/12502 | 2/2002 |
| WO | WO 2007/010533 | 1/2007 |
| WO | WO 2008/135991 | 11/2008 |
| WO | WO 2012/170938 | 12/2012 |
| WO | WO 2013/087911 | 6/2013 |
| WO | WO 2013/087912 | 6/2013 |
| WO | WO 2014/136113 | 9/2014 |
| WO | WO 2014/136114 | 9/2014 |
| WO | WO 2014/136117 | 9/2014 |

OTHER PUBLICATIONS

Sedger et al., Cytokine & Growth Factor Reviews vol. 25 (2014) pp. 453-472.*
Office Action dated Sep. 29, 2016 From the Israel Patent Office Re. Application No. 241151 and Its Translation Into English.
Office Action dated Sep. 29, 2016 From the Israel Patent Office Re. Application No. 241221 and Its Translation Into English.
International Preliminary Report on Patentability dated Sep. 17, 2015 From the International Bureau of WIPO Re. Application No. PCT/IL2014/050227.
International Preliminary Report on Patentability dated Sep. 17, 2015 From the International Bureau of WIPO Re. Application No. PCT/IL2014/050228.
Protalix "Study to Evaluate the Safety and Pharmacokinetics of Oral OPRX-106 (TNFR-Fc Fusion Protein) in Healthy Volunteers", ClinicalTrials.gov, Sevice of the U.S. National Institute of Health, 3 P., Last Verified Aug. 2015.
International Search Report and the Written Opinion dated Jul. 4, 2014 From the International Searching Authority Re. Application No. PCT/IL2014/050227.
International Search Report and the Written Opinion dated Jul. 4, 2014 From the International Searching Authority Re. Application No. PCT/IL2014/050228.
International Search Report and the Written Opinion dated Jul. 4, 2014 From the International Searching Authority Re. Application No. PCT/IL2014/050231.
Menassa et al. "Therapeutic Effectiveness of Orally Administered Transgenic Low-Alkaloid Tobacco Expressing Human Interleukin-10 in a Mouse Model of Colitis", Plant Biotechnology Journal, XP002725896, 5(1): 50-59, Jan. 2007.
Shaaltiel et al. "Oral Administration of a Plant Cell-Expressed Recombinant Anti-TNF Fusion Protein Is Biologically Active in the Gut and Alleviates Immune Mediated Hepatitis", Hepatology, AASLD Abstracts, XP002725897, 58(Suppl.1): 564A, #751, Oct. 2013. & 64th Annual Meeting and Postgraduate Course of the American Association for the Study of Liver Disease, Washington, DC, USA, Nov. 1-5, 2013. Abstract.

(Continued)

*Primary Examiner* — James S Ketter

(57) ABSTRACT

A plant produced chimeric polypeptide is provided. The plant produced chimeric polypeptide comprising:
(i) a first domain which comprises a TNF Alpha binding domain of a TNF receptor, and
(ii) a second domain which comprises an Fc domain of an immunoglobulin, wherein the first domain and the second domain are N-terminally to C-terminally respectively sequentially translationally fused and wherein the chimeric polypeptide specifically binds TNF Alpha.

24 Claims, 22 Drawing Sheets
(8 of 22 Drawing Sheet(s) Filed in Color)

(56) References Cited

OTHER PUBLICATIONS

U.S. National Institutes of Health "Study to Evaluate the Safety and Pharmacokinetics of Oral OPRX-106 (TNFR-Fc Fusion Protein) in Healthy Volunteers", Clinical Trials.gov, a Service of the U.S. National Institutes of Health, 3 P., Apr. 4, 2014.
Wilson et al. "Recent Advances Towards Development and Commercialization of Plant Cell Culture Processes for the Synthesis of Biomolecules", Plant Biotechnology Journal, XP002725895, 10(3): 249-268, Apr. 2012. p. 261, 1-h Col., Last Para—p. 262, 1-h Col., Para 1, p. 262, r-h Col., Para 2, Table 1.
Winichayakul et al. "Head-to-Tail Fusions of Camelid Antibodies Can Be Expressed in Planta and Bind in Rumen Fluid", Biotechnology and Applied Biochemistry, XP002725894, 53(Pt.2): 111-122, Jun. 2009.
Communication Pursuant to Article 94(3) EPC dated Jan. 11, 2017 From the European Patent Office Re. Application No. 147164354. (5 Pages).
Office Action dated Nov. 7, 2017 From the Israel Patent Office Re. Application No. 241151 and Its Translation Into English. (4 Pages).
Office Action dated Nov. 7, 2017 From the Israel Patent Office Re. Application No. 241221 and Its Translation Into English. (4 Pages).
Chan "Plant-Made Oral Vaccines Against Human Infectious Diseases—Are we there yet?",Plant Biotechnology Journal 13(8):1056-1070, Oct. 2015.
Kwon et al. "Oral Delivery of Protein Dmgs Bioencapsulated in Plant Cells", Molecular Therapy 24(8): 1342-1350, Aug. 2016.
MacEwan "Review TNF Ligands and Receptors a Matter of Life and Death", British Journal of Pharmacology, 135(4): 855-875, 2002.
No Author "Protalix Releases Preclinical Data on Anti-TNF Follow-On Biologic Arthritis Drug". Health and Beauty Close-Up. Sep. 29, 2009.
Rosales-Mendoza et al. "Immunological Aspects of Using Plant Cells as Delivery Vehicles for Oral Vaccines", Expert Review of Vaccines 13(6): 737-749, Apr. 28, 2014.
Notice of Reason for Rejection dated Apr. 3, 2018 From the Japan Patent Office Re. Application No. 2015-560846. (5 Pages).
Translation dated Apr. 19, 2018 of Notice of Reason for Rejection dated Apr. 3, 2018 From the Japan Patent Office Re. Application No. 2015-560846. (9 Pages).

* cited by examiner

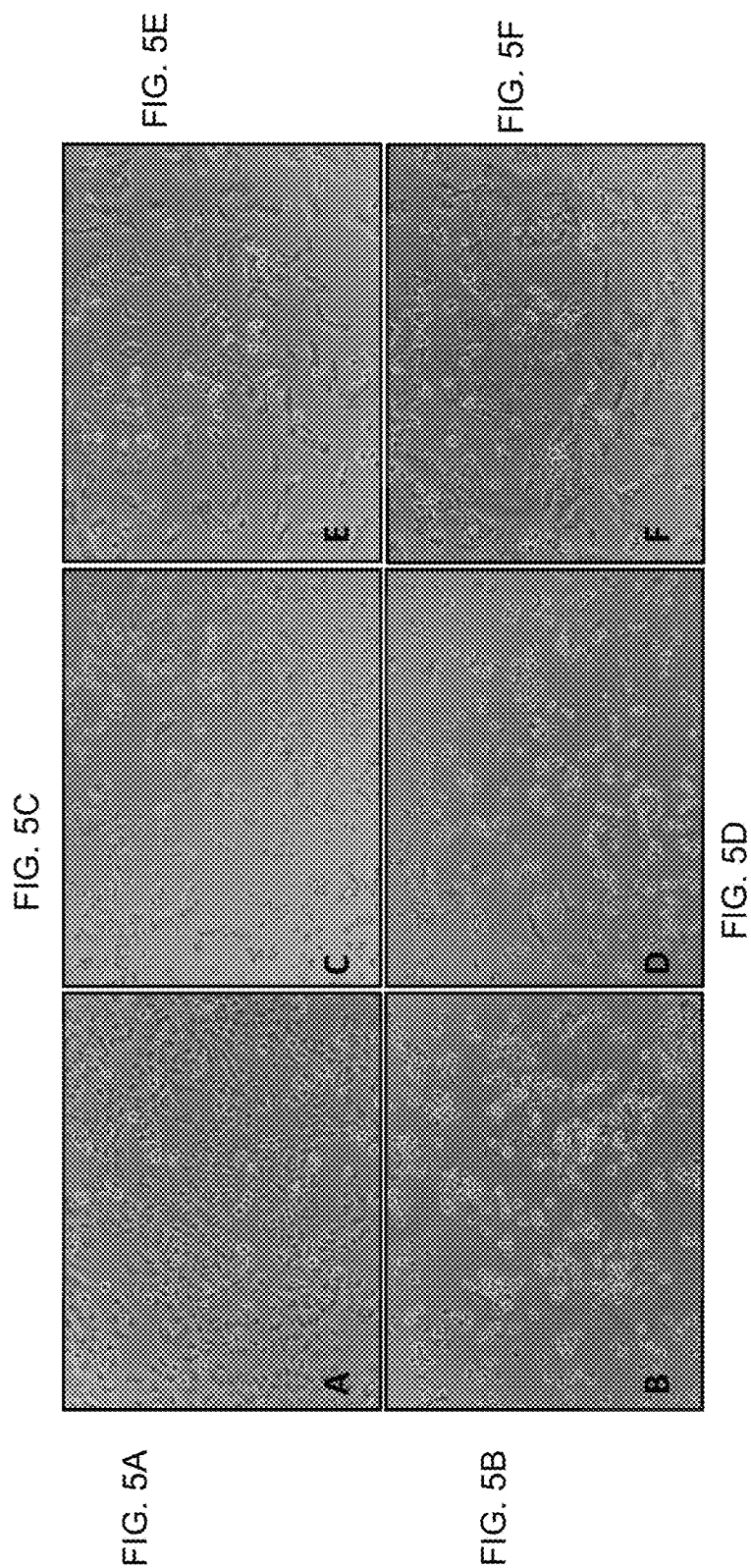

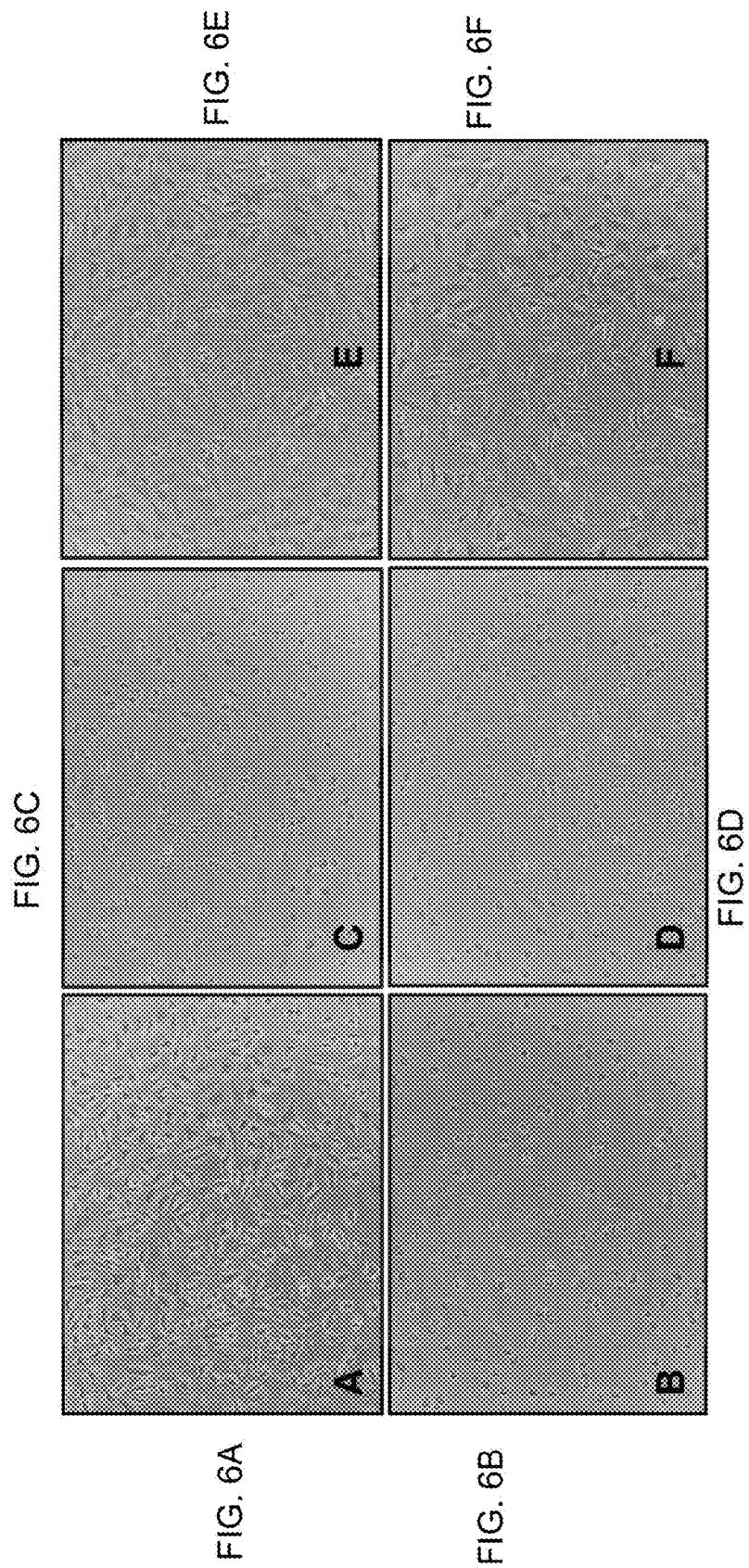

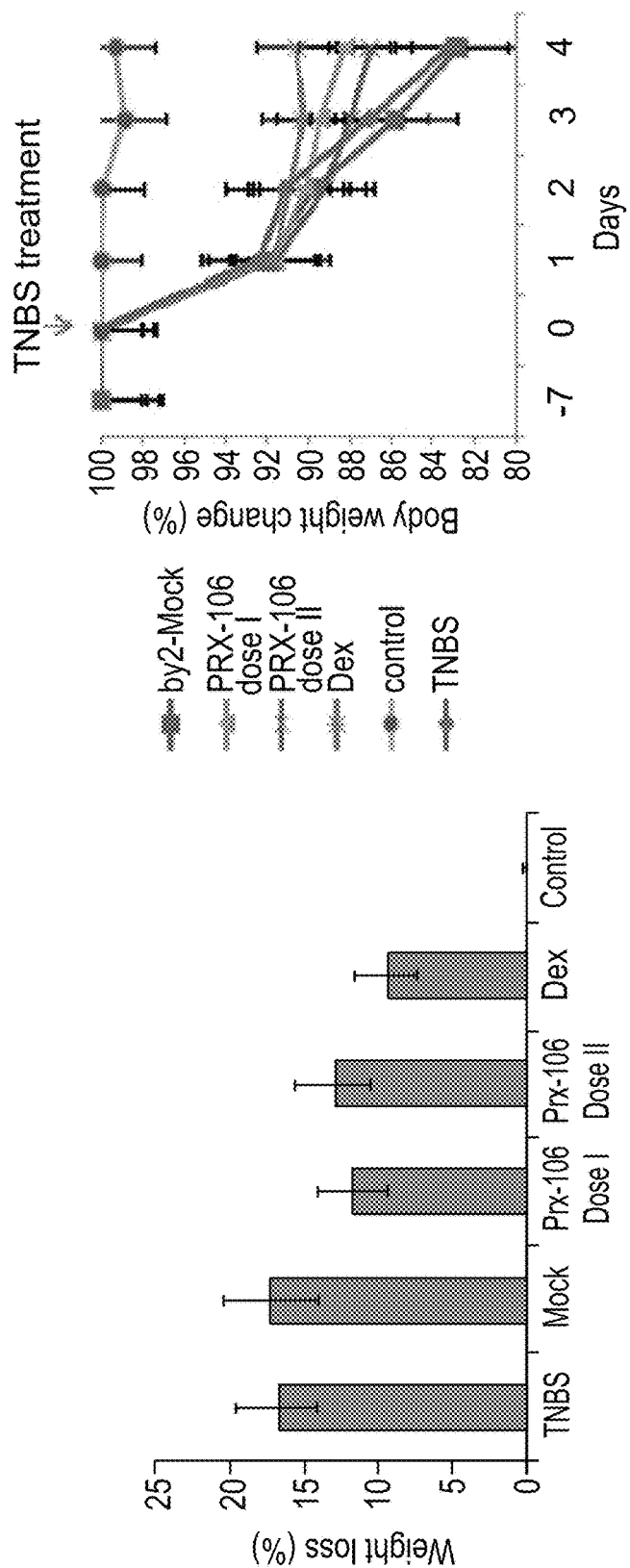

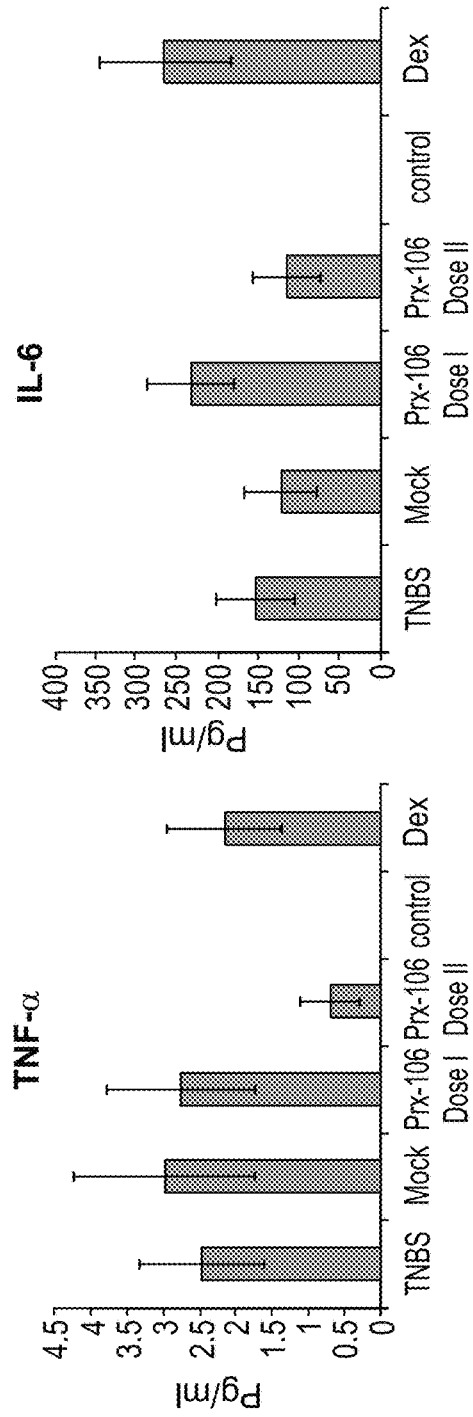
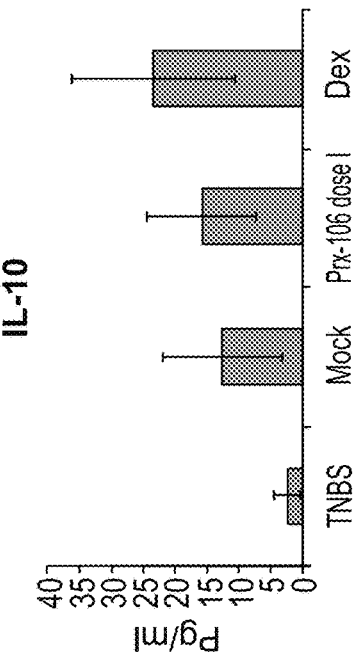
FIG. 10A
FIG. 10B
FIG. 10C

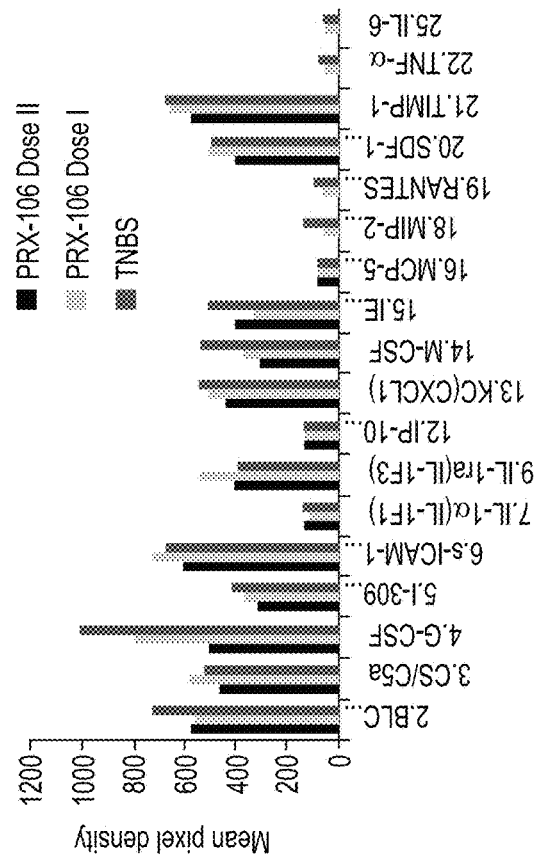
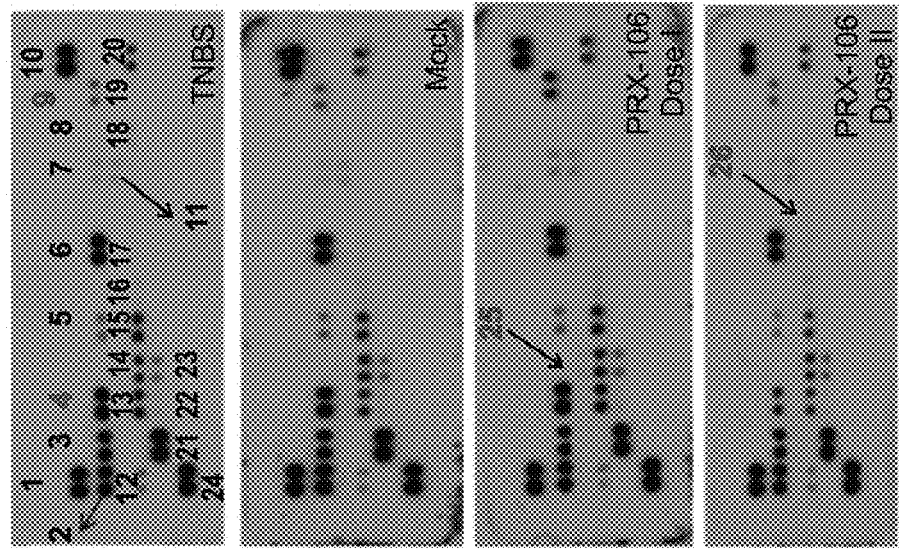

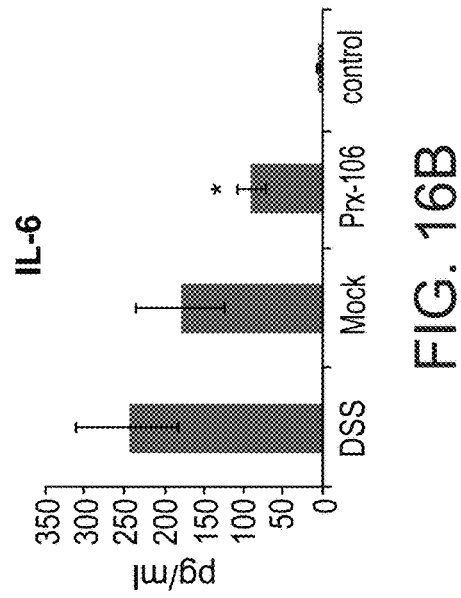
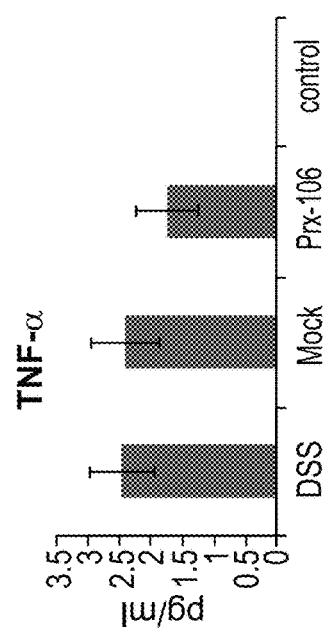
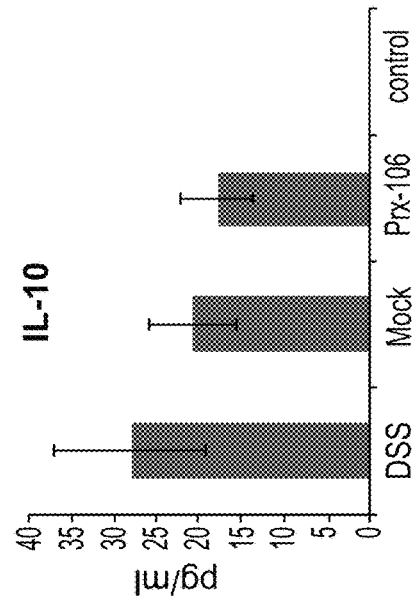
FIG. 16A
FIG. 16B
FIG. 16C

C   Carbamidomethyl (C)
D   Deamidated (Q,N)
O   Oxidation (M)

```
         1         11         21         31         41         51         61         71         81         91        101
         C    DD   CC         C          C     DCC       C  D       C   C  D    C  CC          C    D       C C C  D
MATQRRANPS SLHLITVFSL LVAVVSALPA QVAFTPYAPE PGSTCRLREY YDQTAQMCCS KCSPQGHAKV FCTKTSDVYC DSCEDSTYTQ LWNWYPECLS CGSRCSSBDQY

111      D    D     C     C                 C           C          D      C       C         O
ETQACTREQN RICTCRPGQW CHLSKQEGCR ICAPLRKCRP GTGVARPGTE TSDVVCKPCA PGTFSNITSS TDICRPHQIC NVVAIPGNAS MDAVCTSTSP TRSMAPGAVH

221   D  D     D     C       O         C          C        C              O         C        C   DD       C        DD DD
LPQPVSTRSQ HTQPTPEPST APTSFELLPM GPSPPAEGST GBEPKSQDKT HTCPPCPAPE LLGGPSVFLF PPKPKDTLMI SRTPEVTCVV VDVSHEDPEV KFNWYVDGVE

331           DD               D  C D         D              D               O  DD      C                      DD DD
VHNAKTKPRE EQYNSTYRVV SVLTVLHQDW LNGKEYKCKV SNKALPAPIE KTISKAKGQP REPQVYTLPP SREEMTKNQV SLTCLVKGFY PSDIAVEWES NGQPENNYKT

441              DD   C O    D
TPPVLDSDGS FFLYSKLTVD KSRWQQGNVF SSSVMHEALH NHYTQKSLS. SPGKSEKDEL
```

FIG. 20

CHIMERIC POLYPEPTIDES, POLYNUCLEOTIDES ENCODING SAME, CELLS EXPRESSING SAME AND METHODS OF PRODUCING SAME

RELATED APPLICATION

This application claims the benefit of priority under 35 USC § 119(e) of U.S. Provisional Patent Application No. 62/048,932 filed on Sep. 11, 2014, the contents of which are incorporated herein by reference in their entirety.

SEQUENCE LISTING STATEMENT

The ASCII file, entitled 63425SequenceListing.txt, created on Sep. 10, 2015, comprising 86,864 bytes, submitted concurrently with the filing of this application is incorporated herein by reference.

FIELD AND BACKGROUND OF THE INVENTION

The present invention, in some embodiments thereof, relates to chimeric polypeptides, polynucleotides encoding same, cells expressing same and methods of producing same.

Tumor necrosis factor alpha (TNFα) is an important, pro-inflammatory cytokine mediating the regulation of diverse inflammatory, infectious and immune-related processes and diseases, TNFα being considered the most important mediator responsible for inflammatory pathology.

TNF-alpha is a 17 kD molecular weight protein, initially synthesized as a transmembrane protein arranged in stable trimers, then cleaved by metalloprotease-TNF alpha converting enzyme (TACE) to form the homotrimeric soluble TNF (sTNF) which engages to its cognate receptors (TNFRI, p55 and TNFRII, p75), expressed ubiquitously. The ubiquitous TNF receptors provide the basis for the wide variety of TNF-alpha mediated cellular responses.

TNF-alpha induces a wide variety of cellular responses, many of which result in deleterious consequences, such as cachexia (loss of fat and whole body protein depletion, leading to anorexia, common in cancer and AIDS patients) and septic shock. Elevated secretion of TNF-alpha has been implicated in a variety of human diseases including diabetes, allograft rejection, sepsis, inflammatory bowel diseases, osteoporosis, in many autoimmune diseases such as multiple sclerosis, rheumatoid arthritis, psoriasis, psoriatic arthritis, hypersensitivity, immune complex diseases, and even in malaria, cancer and lung fibrosis.

The biological effect of TNFα is mediated by the two distinct receptors. TNF-alpha receptors, when shed from mononuclear cells, lower the TNF-alpha levels by "mopping up" and acting as natural inhibitors Neutralization of TNFα by specific antibodies and decoy receptors has become a common strategy for regulation of TNFα mediated toxicity.

To date, five protein-based TNFα antagonists have been approved by the US FDA for clinical use: Cimzia (Certolizumab pegol), a TNFmAb Fab' fragment-PEG conjugate; Remicade (Infliximab), a TNF rmAB; Humira (Adalimumab), a TNF rmAB, Simponi™ (Golimumab), aTNF human monoclonal antibody and etanercept, a fusion protein of soluble 75 kDa TNFα receptors fused to the Fc fragment of human IgG (registered as Enbrel™).

Etanercept is indicated for rheumatoid arthritis (RA) and other arthritic indications such as juvenile idiopathic arthritis (JIA), psoriasis and Ankylosing Spondylitis (AS). Rheumatoid arthritis (RA) is a chronic disease that affects approximately five million people World Wide. Nearly 500,000 patients worldwide across indications are treated with Enbrel. Enbrel sales in 2010 were 7.8 billion dollars and the total anti-TNF market amounted to 24.04 Billion dollars. Clinical trials of Enbrel therapy, current or completed, include such diverse indications as adult respiratory distress syndrome, pemphigus, Alzheimer's disease, Behcet's syndrome, HIV, myocardial infarct, knee joint synovitis, lupus nephritis, lichen planus, systemic amyloidosis, sciatica, vitiligo, chronic fatigue syndrome, anorexia, TMJ, asthma, bronchitis, diabetes, myelodysplastic disease and others.

Enbrel is currently produced in mammalian cells. The safety of biopharmaceuticals has recently come to the forefront for both patients and health care providers due to outbreaks of emerging pathogens, most notably HIV, HCV, Cruezfeld-Jacob's Disease, West Nile Virus and SARS, in multiple regions of the world, emphasizing the risk of pathogen transmission through the use of human- or animal-derived raw materials, such as blood-derived products (serum, plasma cell medium components, etc) in the manufacture of biopharmaceuticals. For example, approximately half (!) of the hemophilia population contracted HIV until identification and screening for the virus became widespread.

Screening and testing have improved recently, reducing the threat of pathogen transmission, but risks still remain from plasma-derived additives during recombinant manufacturing processes. In particular, the risk from unknown pathogens is significant, as these agents may appear in the blood supply in the future and could have a significant impact on safety of mammalian-cell-based biopharmaceuticals. Of particular concern are biopharmaceutical drugs which require repeated, regular administrations, specifically via injection, increasing the cumulative risk to the patient.

However, eliminating animal-derived components from media can significantly alter culture performance as well as post-translational protein modifications. The glycosylation pattern of an antibody molecule can affect its structural integrity, thus influencing its biological function, physicochemical properties and pharmacokinetics, altering both efficacy and safety, particularly immunogenicity. Although no major outbreaks have occurred in recent years, it is still critical to reduce dependence on blood and plasma components in the manufacture of biopharmaceuticals. Conversely, recombinant protein production in mammalian cell culture is unsafe due to xeno contaminations. In 2009 Genzyme was forced to temporarily close its main factory because of viral contamination. It did not restore full supplies of the drugs until 2011. Due to the shortage in the only approved drug for Fabry patients in the US, some people with Fabry disease have suffered heart or kidney problems and one or more may have even died because of the shortage.

Biopharmaceuticals, including modified human proteins, can be produced in transgenic plants in order to address problems of safety, viral infections, immune reactions, production yield and cost. U.S. Pat. No. 6,391,638 and PCT WO2008/135991 teach bioreactor devices for commercial-scale production of recombinant polypeptides from plant cell culture. U.S. Pat. No. 7,951,557, U.S. patent application Ser. Nos. 10/554,387 and 11/790,991 teach construction and expression of nucleic acid vectors for recombinant expression of human proteins in plant cells. PCT WO2007/010533 teaches the expression of recombinant human polypeptides in plant cells, for enteral administration.

Additional background art includes: U.S. Pat. No. 7,915,225 to Finck et al, U.S. patent application Ser. Nos. 13/021,545 and 10/853,479 to Finck et al, U.S. patent application Ser. No. 11/906,600 to Li et al, U.S. patent application Ser. No. 10/115,625 to Warren et al and U.S. patent application Ser. No. 11/784,538 to Gombotz et al.

SUMMARY OF THE INVENTION

According to an aspect of some embodiments of the present invention there is provided a plant produced chimeric polypeptide comprising:
(i) a first domain which comprises a TNFα binding domain of a TNF receptor, and
(ii) a second domain which comprises an Fc domain of an immunoglobulin, wherein the first domain and the second domain are N-terminally to C-terminally respectively sequentially translationally fused and wherein the chimeric polypeptide specifically binds TNFα.

According to an aspect of some embodiments of the present invention there is provided a chimeric polypeptide comprising:
(i) a first domain which comprises a TNFα binding domain of a TNF receptor;
(ii) a second domain which comprises an Fc domain of an immunoglobulin; and
(iii) a third domain comprising an endoplasmic reticulum retention signal;
wherein the first domain, second domain and third domain are N-terminally to C-terminally respectively sequentially translationally fused and wherein the chimeric polypeptide specifically binds TNFα.

According to some embodiments of the invention, the polypeptide comprises an additional domain encoding an endoplasmic reticulum signal peptide translationally fused N-terminally to the first domain.

According to some embodiments of the invention, the signal peptide is a plant signal peptide.

According to some embodiments of the invention, the plant signal peptide is as set forth in SEQ ID NO: 4.

According to some embodiments of the invention, the first domain is 200-250 amino acids long.

According to some embodiments of the invention, the first domain comprises the amino acid sequence LCAP (SEQ ID NO: 11) and VFCT (SEQ ID NO: 12).

According to some embodiments of the invention, the first domain further comprises the amino acid sequence LPAQVAFXPYAPEPGSTC (SEQ ID NO: 13) or LPAQVAFTPYAPEPGSTC (SEQ ID NO: 17).

According to some embodiments of the invention, the first domain is as set forth in SEQ ID NO: 2.

According to some embodiments of the invention, the immunoglobulin is IgG$_1$.

According to some embodiments of the invention, the second domain is as set forth in SEQ ID NO: 9.

According to some embodiments of the invention, the polypeptide is as set forth in SEQ ID NO: 6.

According to some embodiments of the invention, the polypeptide is as set forth in SEQ ID NO: 7, 204 or 205.

According to some embodiments of the invention, the polypeptide is purified to at least 98% homogeneity.

According to some embodiments of the invention, the polypeptide is capable of inhibiting TNFα-induced apoptosis.

According to some embodiments of the invention, the polypeptide comprises a plant-specific glycan.

According to some embodiments of the invention, the plant-specific glycan is selected from the group consisting of a core xylose and a core α-(1,3) fucose.

According to an aspect of some embodiments of the present invention there is provided an isolated polynucleotide comprising a nucleic acid sequence encoding the polypeptide.

According to an aspect of some embodiments of the present invention there is provided a codon usage of the nucleic acid sequence is optimized for Nicotinia tabaccum.

According to an aspect of some embodiments of the present invention there is provided the isolated polynucleotide as set forth in SEQ ID NO: 5.

According to an aspect of some embodiments of the present invention there is provided a nucleic acid expression construct comprising a nucleic acid sequence encoding the polynucleotide and a cis-acting regulatory element active in a plant cell.

According to an aspect of some embodiments of the present invention there is provided the cis-acting regulatory element is a promoter.

According to an aspect of some embodiments of the present invention there is provided a plant cell comprising the nucleic acid construct.

According to an aspect of some embodiments of the present invention there is provided the plant cell is a Nicotiana tabacum plant cell.

According to an aspect of some embodiments of the present invention there is provided the Nicotiana tabacum L. cv plant cell is a Bright Yellow (BY-2) cell.

According to an aspect of some embodiments of the present invention there is provided the plant cell is lyophilized.

According to an aspect of some embodiments of the present invention there is provided a plant cell suspension culture comprising the plant cell.

According to an aspect of some embodiments of the present invention there is provided a pharmaceutical composition comprising as an active ingredient the polypeptide and a pharmaceutically acceptable carrier.

According to an aspect of some embodiments of the present invention there is provided a pharmaceutical composition comprising as an active ingredient the plant cell and a pharmaceutically acceptable carrier.

According to an aspect of some embodiments of the present invention there is provided a method of treating a TNFα-associated medical condition in a subject in need thereof, the method comprising administering to the subject a therapeutically effective amount of the polypeptide, thereby treating the TNFα-associated medical condition in the subject.

According to an aspect of some embodiments of the present invention there is provided a method of treating a TNFα-associated medical condition in a subject in need thereof, the method comprising administering to the subject a therapeutically effective amount of the plant cells, thereby treating the TNFα-associated medical condition in the subject.

According to an aspect of some embodiments of the present invention there is provided the polypeptide for use in treating a TNFα-associated medical condition in a subject.

According to some embodiments of the invention, the plant cells are for use in treating a TNFα-associated medical condition in a subject.

According to an aspect of some embodiments of the present invention there is provided a use of the polypeptide in treating a TNFα-associated medical condition in a subject.

According to an aspect of some embodiments of the present invention there is provided a use of the plant cells in treating a TNFα-associated medical condition in a subject.

According to some embodiments of the invention, the medical condition is an inflammatory disease.

According to some embodiments of the invention, the medical condition is an autoimmune disease.

According to some embodiments of the invention, the medical condition is selected from the group consisting of rheumatoid arthritis, ankylosing spondyloarthritis, plaque psoriasis and juvenile idiopathic arthritis.

According to some embodiments of the invention, the medical condition is selected from the group consisting of rheumatoid arthritis, inflammatory bowel disease, short bowel syndrome, sepsis, endotoxic shock, AIDS, endometriosis, psoriasis, cardiovascular disease, cancer, vitiligo, arthritis, rheumatoid polyarthritis, psoriatic rheumatism, ankylosing spondyloarthritis, plaque psoriasis, juvenile idiopathic arthritis, polyarticular juvenile idiopathic arthritis, psoriasis arthritis, Wegener's disease (granulomatosis), Crohn's disease, short bowel syndrome, ulcerative cholitis, chronic obstructive pulmonary disease (COPD), Hepatitis C, asthma, cachexia, atopic dermatitis. Alzheimer's disease, hepatic encephalopathy, ADHD, chronic fatigue syndrome dermatitis herpetiformis (Duhring's disease), contact dermatitis, urticaria (including chronic idiopathic urticaria), autoimmune blistering diseases, including pemphigus vulgaris, bullous pemphigoid, myesthenia gravis, sarcoidosis, including pulmonary sarcoidosis, scleroderma, reactive arthritis, hyper IgE syndrome, multiple sclerosis and idiopathic hypereosinophil syndrome, and allergy.

According to some embodiments of the invention, the medical condition is an inflammatory bowel disease.

According to some embodiments of the invention, the inflammatory bowel disease is ulcerative colitis or Crohn's disease.

According to some embodiments of the invention, the plant cells are formulated for oral administration.

According to some embodiments of the invention, the polypeptide is formulated for parenteral administration.

According to some embodiments of the invention, the plant cells are formulated for enteral administration and wherein the medical condition is not an obesity, metabolic syndrome, diabetes and a liver disease or disorder.

According to an aspect of some embodiments of the present invention there is provided a method of producing the polypeptide, comprising:
 providing a cell as described herein; and
 culturing the cell so as to produce the polypeptide.

According to some embodiments of the invention, the method further comprises isolating the polypeptide from the cell.

According to some embodiments of the invention, the cell is an isolated cell cultured in a plant cell culture medium.

According to some embodiments of the invention, the culturing is performed in a disposable bioreactor.

According to an aspect of some embodiments of the present invention there is provided a method of treating a TNFα-associated medical condition in a subject in need thereof, the method comprising orally administering to the subject a therapeutically effective amount of the plant cells of claim 23, wherein the therapeutically effective amount of the polypeptide in the plant cells comprises 0.02-0.27 mg/kg, thereby treating the TNFα-associated medical condition in the subject.

According to an aspect of some embodiments of the present invention there is provided use of the plant cells of claim 23 in the manufacture of a medicament identified for the treatment of a TNFα-associated medical condition, wherein a therapeutically effective amount of the polypeptide in the plant cells is 0.02-0.27 mg/kg, wherein the plant cells are formulated for oral administration.

According to some embodiments of the invention, the therapeutically effective amount comprises 0.02-0.12 mg polypeptide/kg.

According to some embodiments of the invention, the therapeutically effective amount comprises 0.12-0.27 mg polypeptide/kg.

According to an aspect of some embodiments of the present invention there is provided an oral dosage form comprising the plant cells of claim 23 comprising 1-20 mg of the polypeptide.

According to some embodiments of the invention, the oral dosage form comprises 1-10 mg of the polypeptide.

According to some embodiments of the invention, the oral dosage form comprises 10-20 mg of the polypeptide.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
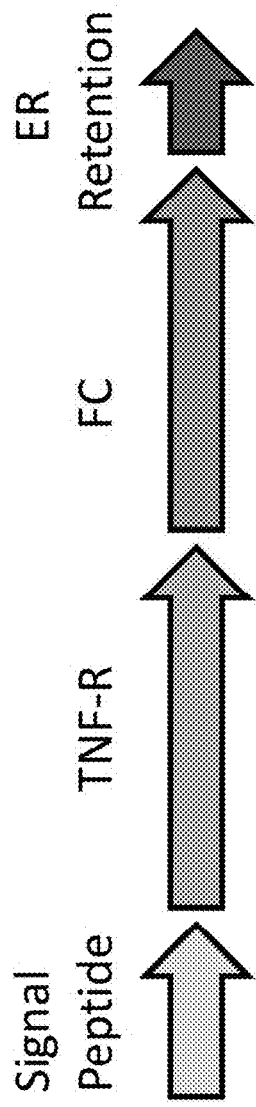

FIG. 1 is a schematic illustration of the amino acid sequence of plant recombinant human (prh) TNFR2:Fc (also termed herein PRX-106, SEQ ID NO:6). prh TNFR2:Fc cDNA for expression in BY2 cells was assembled with a signal peptide for targeting the fusion polypeptide composed of the TNF-binding moiety of the TNF receptor and FC protein to the secretory pathway. Colour code for the amino acids sequence: the signal peptide is coloured in yellow; the TNF receptor portion is coloured in black (green); the Fc portion of IgG1 is in blue; ER retention signal in red.

Figure 2:
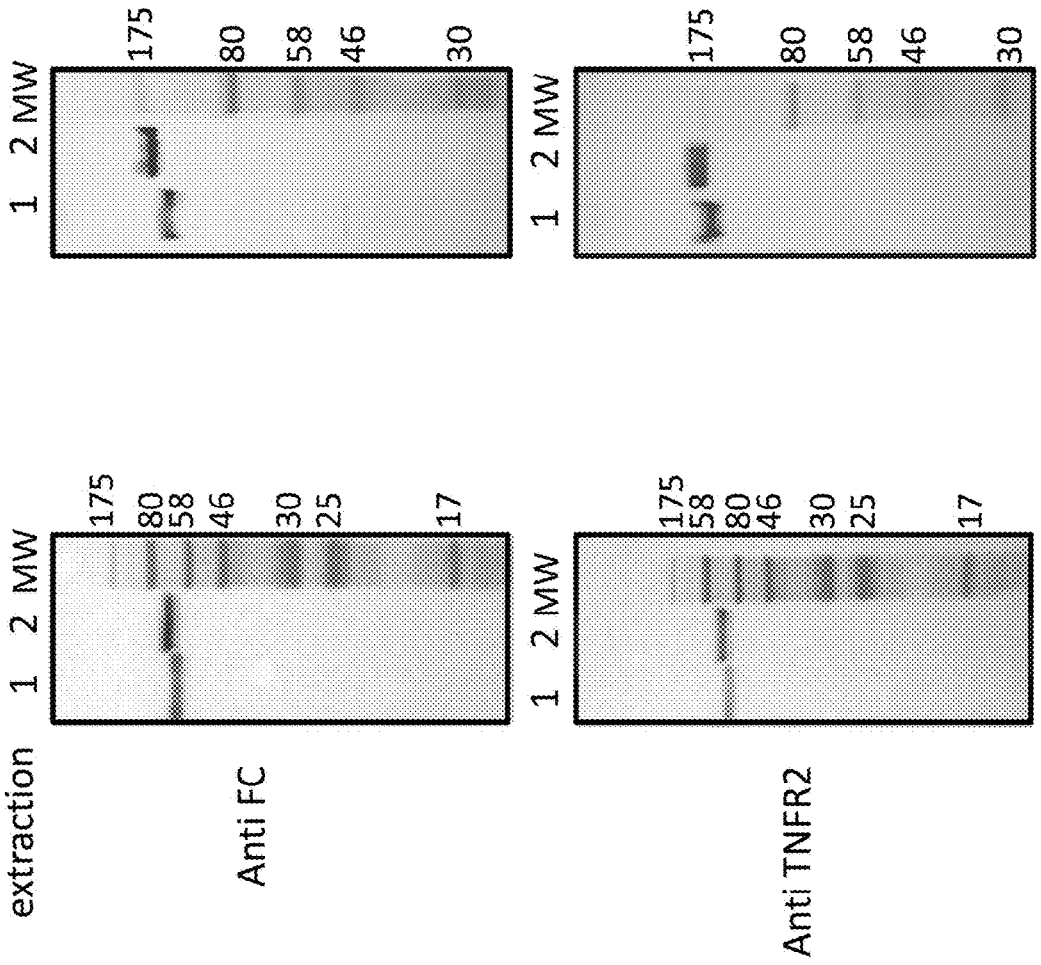

FIGS. 2A-B show comparison of PRH TNFR2:FC and Commercial Enbrel by Western-blot. prh TNFR2:Fc (lane 1) and commercial Enbrel (lane 2) were analyzed under reducing conditions (panel A) and non-reducing conditions (panel B) by 12% and 8% Tris-Glycine SDS-PAGE, respectively. Membranes were blotted with an anti FC antibody (upper panel) and with an anti TNFR2 antibody (lower panel). Molecular weight marker is shown in right lanes. Lane 1: prh TNFR2:FC; Lane 2:commercial Enbrel.

Figure 3:
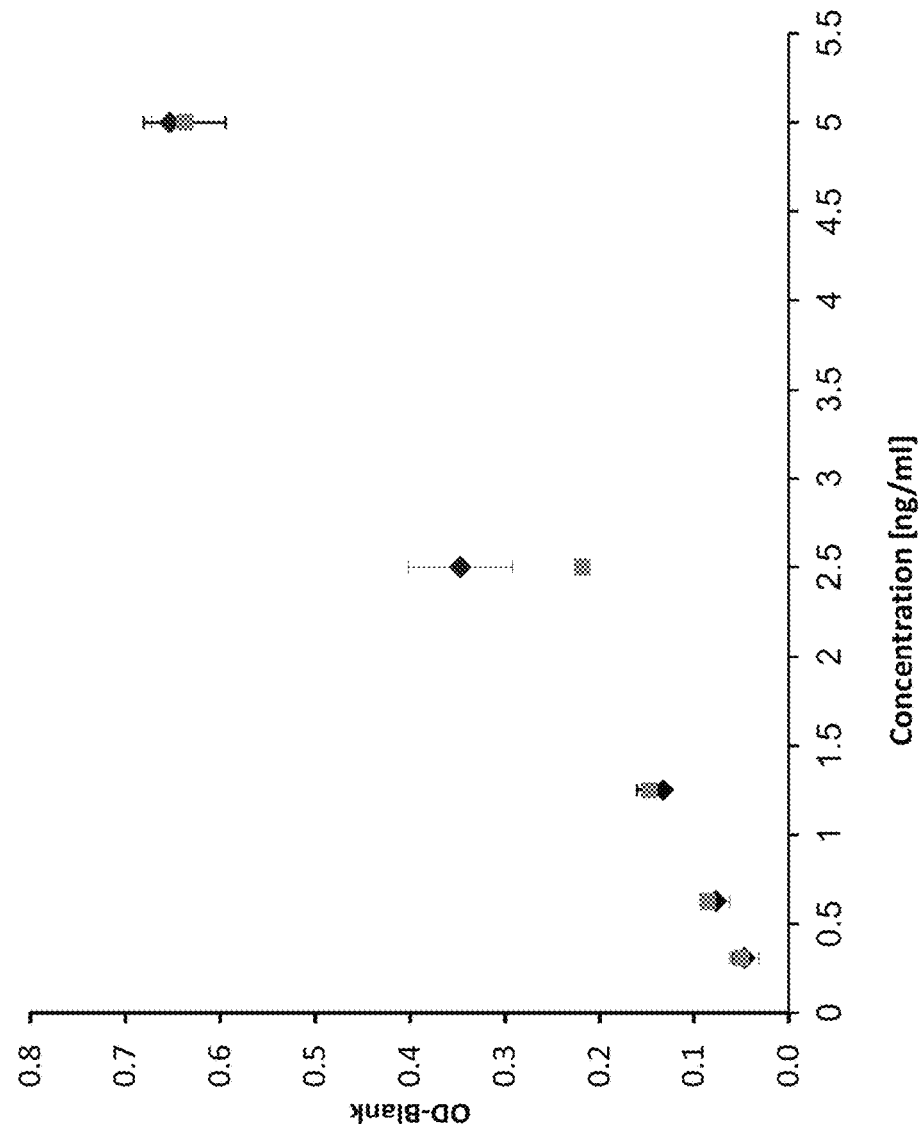

FIG. 3 is a graph showing TNFα binding by prh TNFR2:Fc and commercial Enbrel by quantitative non radioactive assay for prh TNFR2:Fc binding activity and molecular integrity. An ELISA plate pre-coated with antibodies against TNFα, was incubated with TNFα followed by exposure to commercial Enbrel and supernatant from BY2 cells expressing prh TNFR2:Fc. Serial dilutions of both tested items are shown in the X axis. Fc portion of the molecule was detected with Goat anti human IgG Fc HRP.

Figure 4:
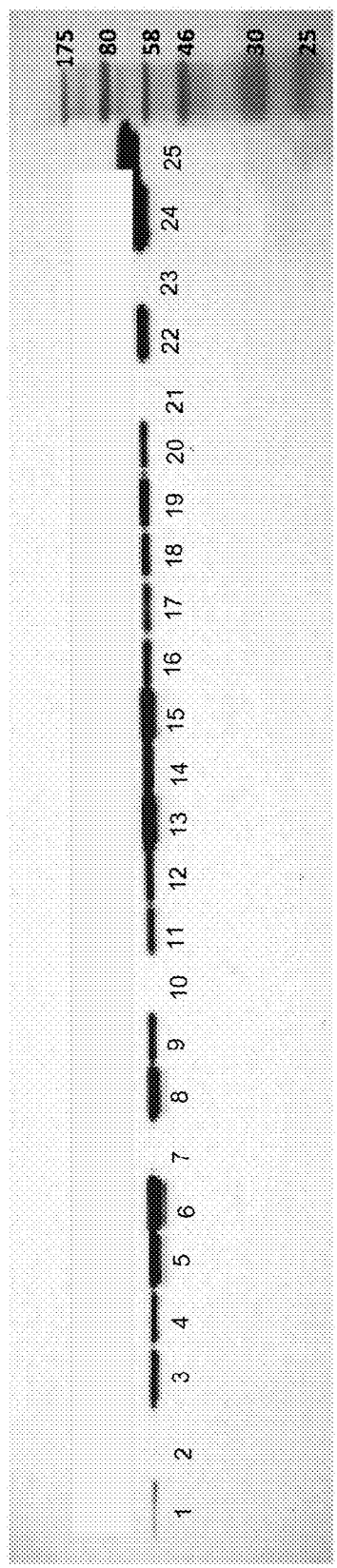

FIG. 4 is an image showing screening of individual cell lines for expression of prh TNFR2:Fc by Western blot analysis.

FIGS. 5A-F are images showing TNFα cytotoxicity in A375 cells in the presence of prh TNFR2:Fc or commercial Enbrel by MTT viability assay. FIG. 5A-untreated Cultured A375 cells; FIG. 5B-treated with TNFα; FIG. 5C—TNFα exposed cells treated with prh TNFR2:Fc (3.125 ng/ml); FIG. 5D—TNFα exposed cells treated with commercial Enbrel (3.125 ng/ml); FIG. 5E—TNFα exposed cells treated with prh TNFR2:Fc (100 ng/ml); FIG. 5F—TNFα exposed cells treated with commercial Enbrel (100 ng/ml).

Figure 5G:
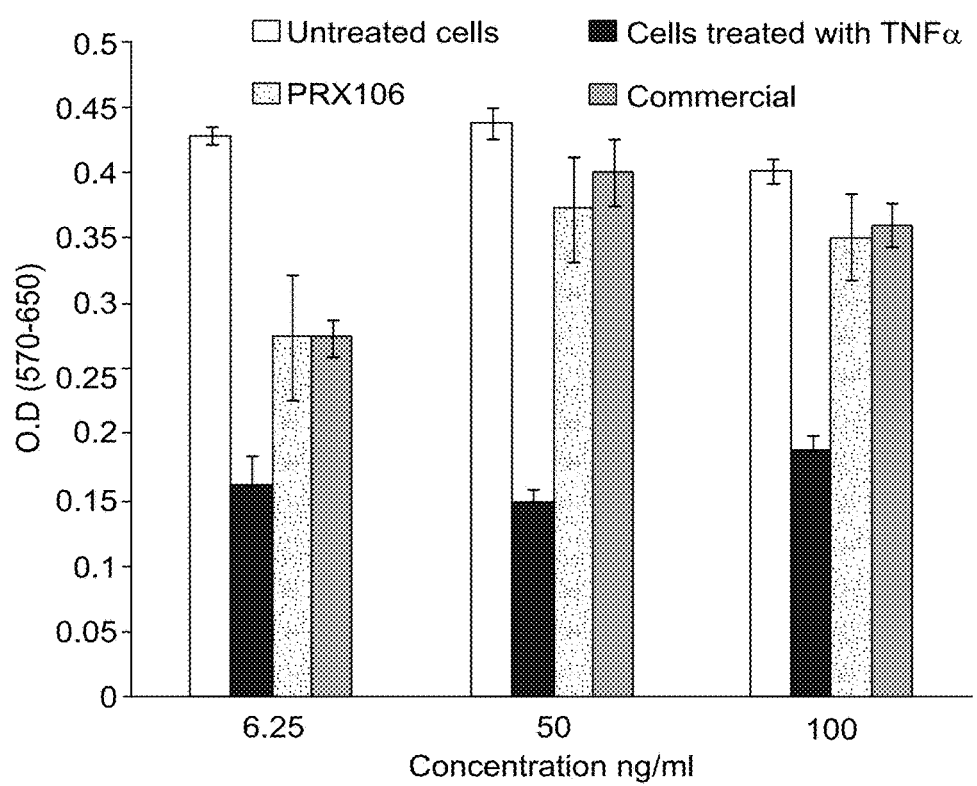

FIG. 5G is a bar graph showing TNFα cytotoxicity in A375 cells in the presence of prh TNFR2:Fc or commercial Enbrel by MTT viability assay.

FIGS. 6A-F are images showing TNFα cytotoxicity in L929 cells in the presence of prh TNFR2:Fc or commercial Enbrel by MTT viability assay. FIG. 6A-untreated Cultured L929 cells; FIG. 6B-treated with TNFα; FIG. 6C—TNFα exposed cells treated with prh TNFR2:Fc (3.125 ng/ml); FIG. 6D—TNFα exposed cells treated with commercial Enbrel (3.125 ng/ml); FIG. 6E—TNFα exposed cells treated with prh TNFR2:Fc (100 ng/ml); FIG. 6F—TNFα exposed cells treated with commercial Enbrel (100 ng/ml).

Figure 6G:
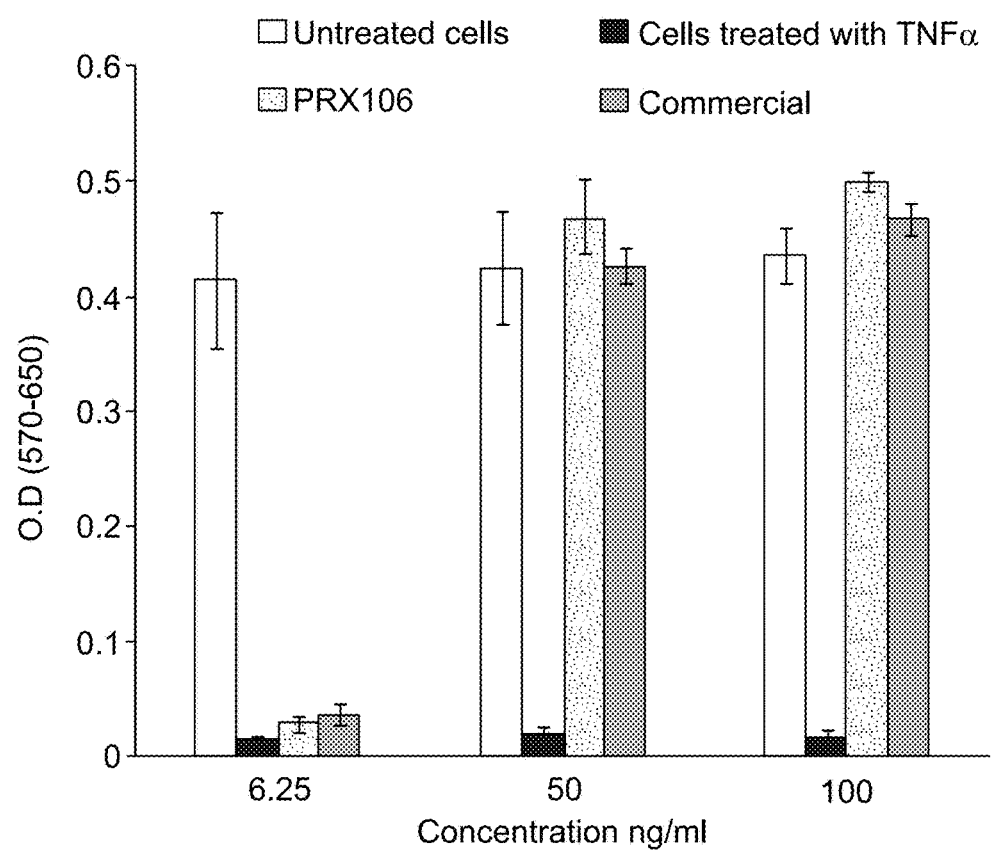

FIG. 6G is a bar graph showing TNFα cytotoxicity in L929 cells in the presence of prh TNFR2:Fc or commercial Enbrel by MTT viability assay.

FIGS. 7A-B are graphs showing body weight changes following TNBS challenge. Mice were orally administered with prh TNFR2:Fc 6 hours after TNBS induction. For four consecutive days body weights were determined daily (means±SE). FIG. 7A—Average weight loss at day four following treatment with TNBS, presented in % loss from original weight. column 1-saline control (n=15); column 2—Mock-host plant control cells (BY2-; n=15); column 3-PRX-106—plant cells expressing recombinant TNFR2:Fc (doseI) (n=15); column 4-PRX-106—plant cells expressing recombinant TNFR2:Fc (dose II) (n=7); column 5—Dexametason treated mice (n=10); column 6-control mice (n=5). FIG. 7B—Average weight loss during four days following treatment with TNBS, presented in % loss from original weight. Note oral treatment with plant cells expressing recombinant TNFR2:Fc attenuated body weight reduction.

Figure 8:
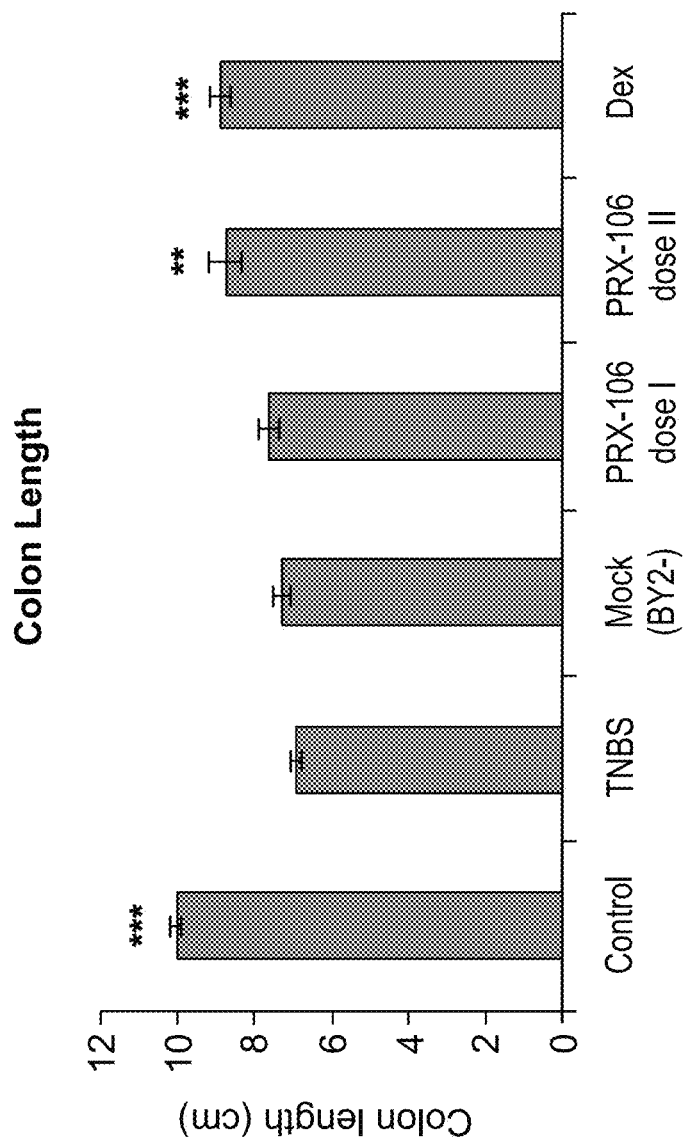

FIG. 8 is a bar graph showing that oral administration of plant cells expressing TNFR2:Fc inhibits TNBS-induced colonic shorting. The mice with colitis were orally administered with plant cells expressing TNFR2:Fc for four consecutive days after TNBS induction and the colon lengths were determined at day 4 (means±SE). From left to right: Column 1—control mice (n=5); column 2—saline control (n=15); column 3—Mock-host plant control cells (BY2-; n=15); column 4—PRX-106—plant cells expressing recombinant TNFR2:Fc (doseI) (n=15); column 5—PRX-106—plant cells expressing recombinant TNFR2:Fc (dose II) (n=7); column 6—Dexametason treated mice (n=10).

Figure 9:
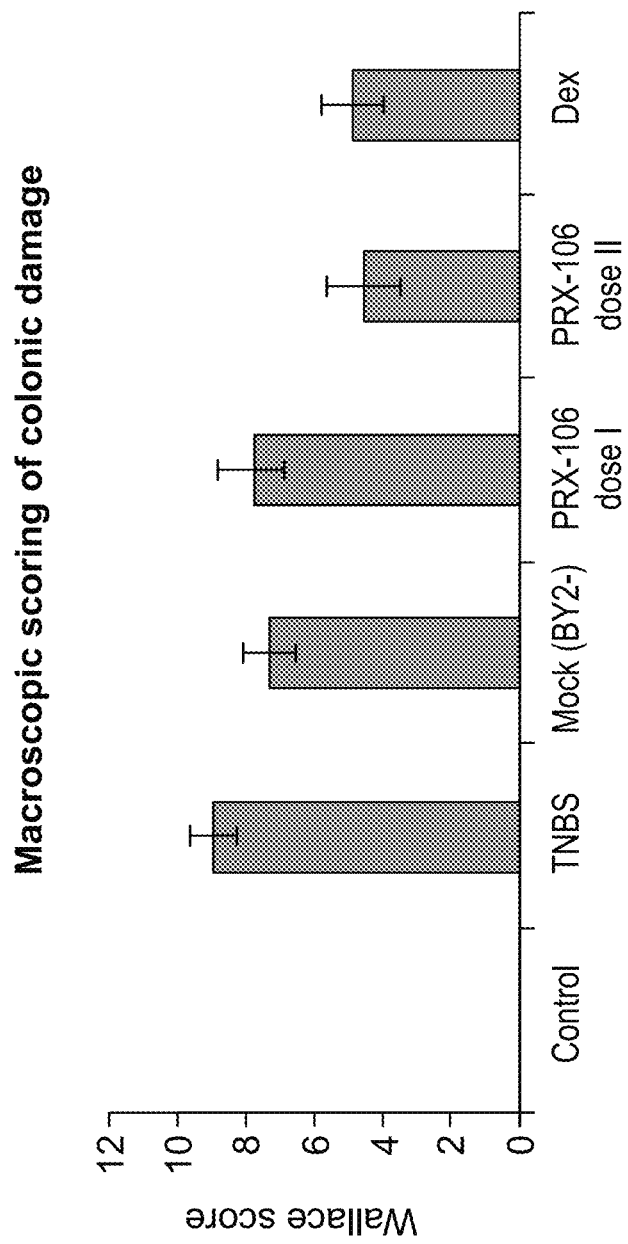

FIG. 9 is a bar graph showing that oral administration of plant cells expressing TNFR2:Fc improved the macroscopic futures of TNBS-induced colitis. Total macroscopic inflammation scores (Wallace score) in control and treated rats at the end-point of the experiment (means±SE). Column 1—control mice (n=5); column 2—saline control (n=15); column 3—Mock-host plant control cells (BY2-; n=15); column 4—PRX-106—plant cells expressing recombinant TNFR2:Fc (doseI) (n=15); column 5—PRX-106—plant cells expressing recombinant TNFR2:Fc (dose II) (n=7); column 6—Dexametason treated mice (n=10).

FIGS. 10A-C are bar graphs showing serum cytokine content in mice treated by oral administration of plant cells expressing TNFR2:Fc as measured by a cytokine antibody array. Sera from groups treated with Mock-host plant control cells (BY2-) (n=15) and Plant cells expressing recombinant TNFR2:Fc protein dose I (n=15), and dose II (n=7) were collected and subjected to cytokine magnetic Luminex assay. TNB—saline control (n=15); Mock-host plant control cells (BY2-; n=15); PRX-106—plant cells expressing recombinant TNFR2:Fc (doseI) (n=15); PRX-106—plant cells expressing recombinant TNFR2:Fc (dose II) (n=7); Dexametason treated mice (n=10); control mice (n=5).

FIGS. 11A-B show serum cytokine content by cytokine Antibody array. FIG. 11A—Sera from groups treated with Mock-host plant control cells (BY2-) (n=15) and plant cells expressing recombinant TNFR2:Fc protein dose I (n=15), and dose II (n=7) were pooled, collected and subjected to cytokine antibody array analysis. FIG. 11B—Cytokine quantification of array. Results indicate that treatment with PRX-106 reduced level of inflammatory mediators like granulocyte colony-stimulating factor G-CSF, macrophage colony-stimulating factor (M-CSF), potentially indicating reduced systemic inflammation by lowering systemic recruitment of bone marrow derived cells from the bloodstream.

Figure 12:
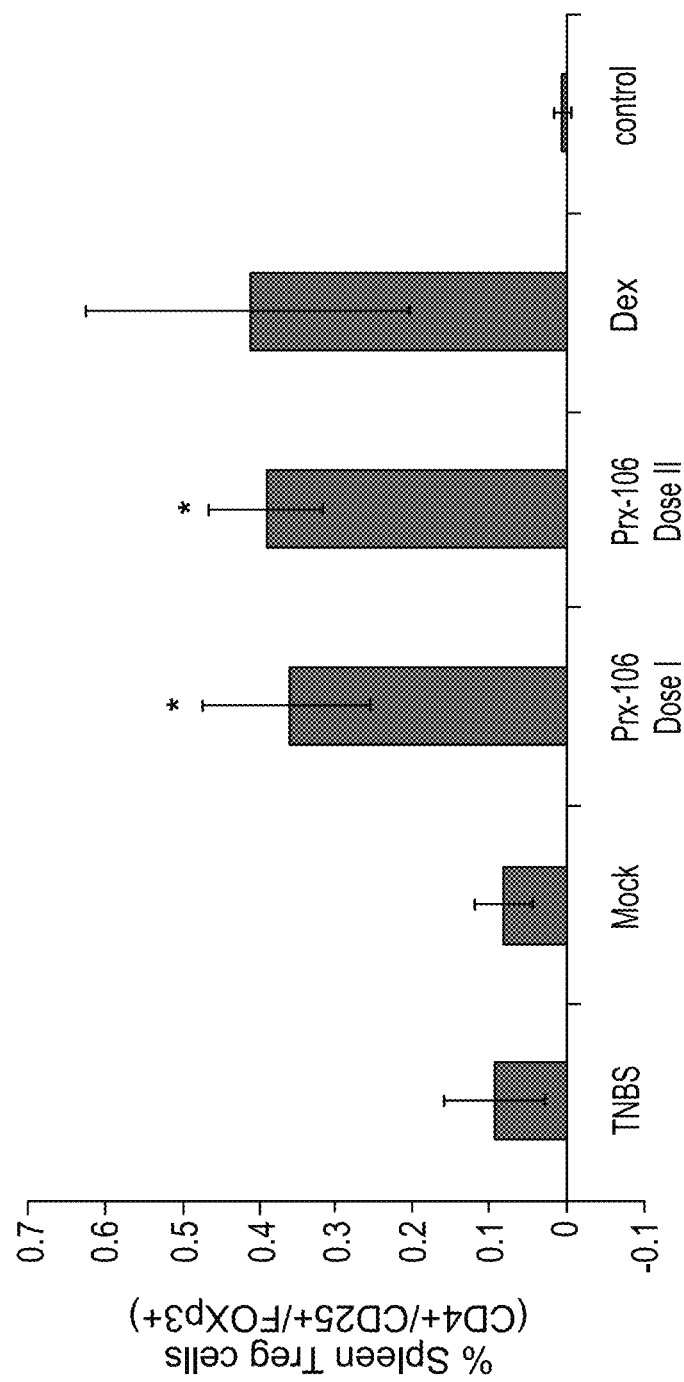

FIG. 12 is a bar graph showing expansion of splenic Treg population in animals treated with plant cells expressing recombinant TNFR2:Fc. Spleen of Balb/c mice, treated with PRX-106 during TNBS induced colitis were analyzed for the percentages of CD4+CD25+Foxp3+, bars indicate SE. Column 1-saline control (n=15); column 2—Mock-host plant control cells (BY2-; n=15); column 3—PRX-106—plant cells expressing recombinant TNFR2:Fc (doseI) (n=15); column 4—PRX-106—plant cells expressing recombinant TNFR2:Fc (dose II) (n=7); column 5—Dexametason treated mice (n=10); column 6-control mice (n=5).

Figures 13A, 13B:
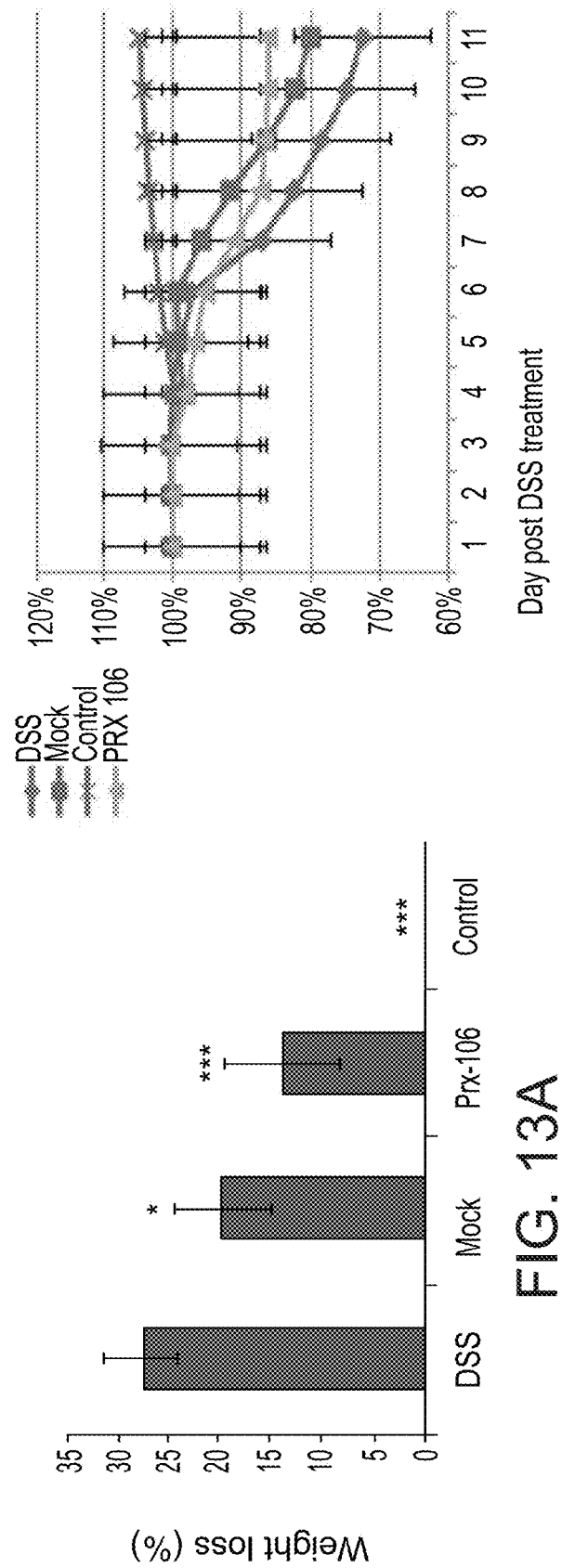

FIGS. 13A-B are graphs showing body weight changes following DSS challenge. The mice with colitis were orally administered with plant cells expressing TNFR2:Fc for seven consecutive days 24 hours after DSS induction and the body weights of mice were determined (means±SE). FIG. 13A—Average weight loss at day ten following treatment with DSS, presented in % loss from original weight. column 1—saline control (n=10); column 2—Mock-host plant control cells (BY2-; n=10); column 3—oral administration of plant cells expressing recombinant TNFR2:Fc (n=10); column 4—control mice (n=5). FIG. 13B—Average weight loss during ten days following treatment with DSS, presented in % loss from original weight. Note oral treatment with PRX-106—plant cells expressing recombinant TNFR2:Fc attenuated body weight reduction. *P<0.05, P<0.01, *P<0.001.

Figure 14B:
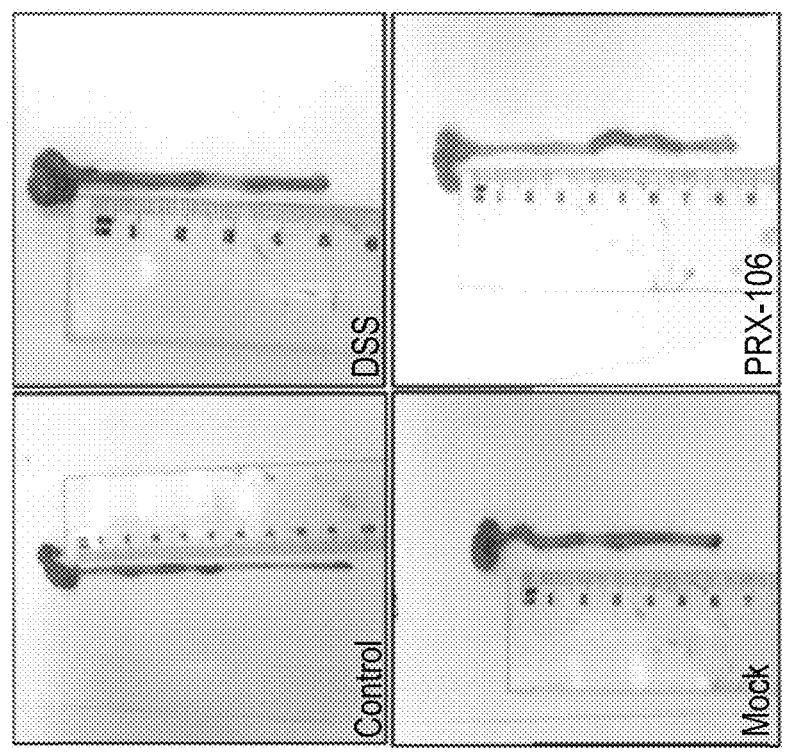
Figure 14A:
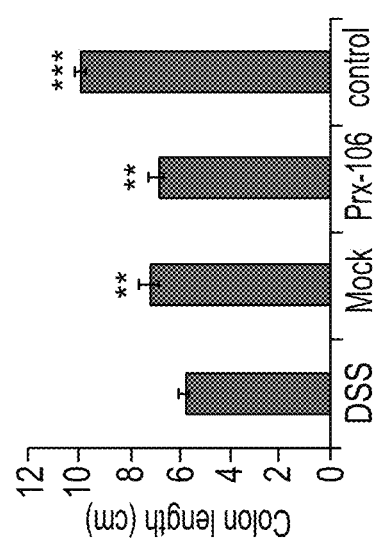

FIGS. 14A-B show that oral administration of TNFR2:Fc inhibited DSS-induced colonic shorting. The mice with colitis were orally administered with plant cells expressing recombinant TNFR2:Fc for 7 consecutive days after DSS induction and the colon lengths were determined at day 10 (means±SE). FIG. 14A—Column 1—saline control (n=10); column 2—Mock-host plant control cells (BY2-; n=10);

column 3—plant cells expressing recombinant TNFR2:Fc (n=10); column 4—control mice (n=5). FIG. 14B—Representative photograph of colons, ten days after the induction of DSS colitis.

Figure 15A:
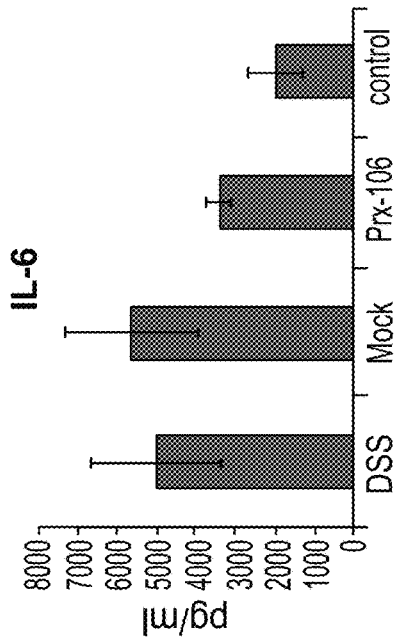
Figure 15B:
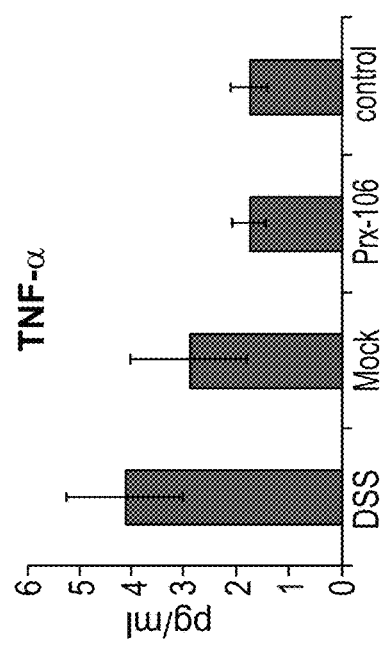
Figure 15C:
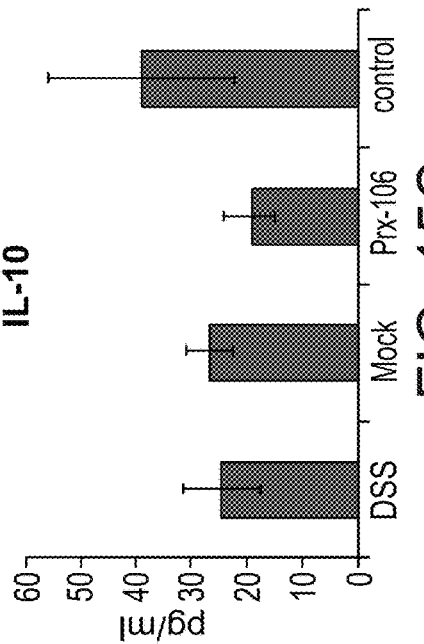

FIGS. 15A-C are graphic presentations of cytokine profile in colons obtained from treated mice. Cytokine secretion by ex vivo-cultured punch biopsies harvested from the colon of Column 1-DSS treated mice receiving saline control (n=10); column 2—DSS treated mice receiving Mock-host plant control cells (BY2-; n=10); column 3-DSS treated mice receiving plant cells expressing 30 μg recombinant TNFR2:Fc (n=10); column 4-control untreated mice (n=5).

FIGS. 16A-C are graphic presentations of serum cytokine content assayed by cytokine Antibody array. Sera from mice treated with Mock-host plant control cells (BY2-) n=15) and Plant cells expressing recombinant TNFR2:Fc protein (n=10), were collected and subjected to cytokine magnetic Luminexas say. Column 1-saline control (n=10); column 2—Mock-host plant control cells (BY2-; n=10); column 3-oral administration of plant cells expressing recombinant TNFR2:Fc (n=10); column 4-control mice (n=5). *P<0.05.

Figure 17B:
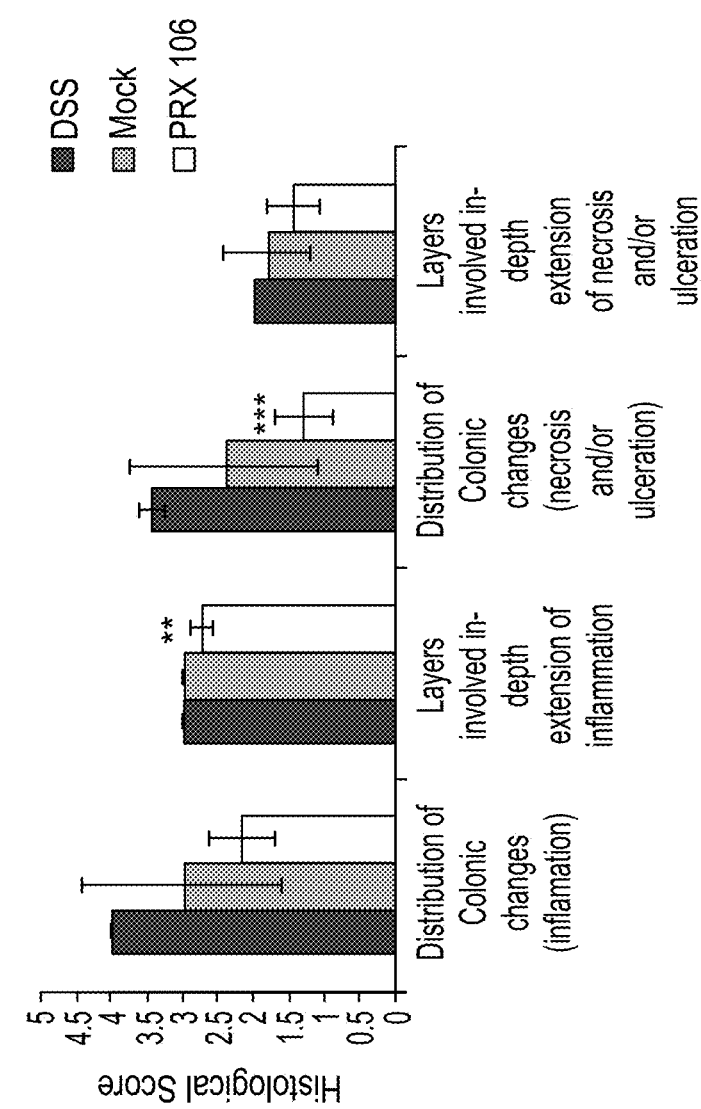
Figure 17A:
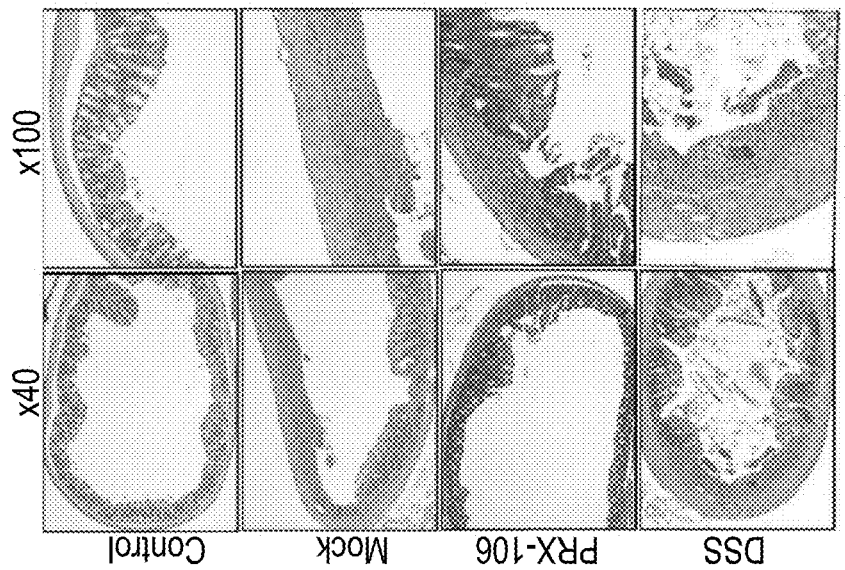

FIGS. 17A-B show that therapeutic treatment with orally administered plant cells expressing recombinant TNFR2:Fc reduces the severity of DSS-induced colitis. FIG. 17A—Representative histological sections were examined microscopically after H&E staining with magnification ×40 and ×100. The images are representative of at least seven mice per group. FIG. 17B—The effect of orally administered plant cells expressing recombinant TNFR2:FC on histological colitis score was determined. White square—plant cells expressing recombinant TNFR2:Fc (n=7), Gray square—Mock-host plant control cells (BY2–; n=10), Black square-saline control (n=8). P<0.01, * P<0.001.

Figure 18:
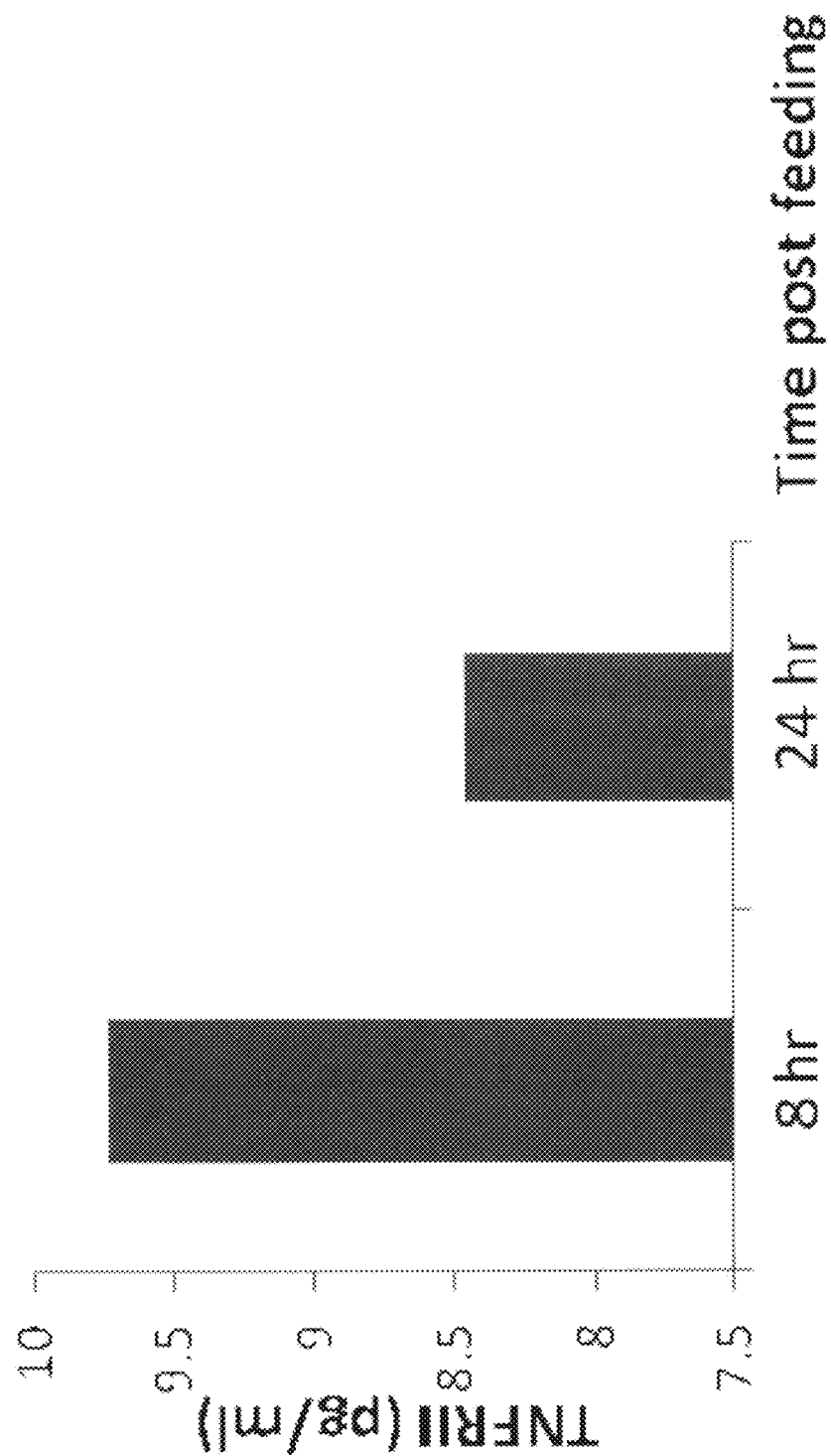

FIG. 18 is a bar graph showing pharmacokinetics of TNFR2:Fc in rat sera. Oral administration of plant cells expressing recombinant TNFR2:Fc was initiated by free feeding. Rats (n=6) received plant cells expressing recombinant TNFR2:Fc. Negative controls received the same volumes of host BY2(–) plant.

Figure 19:
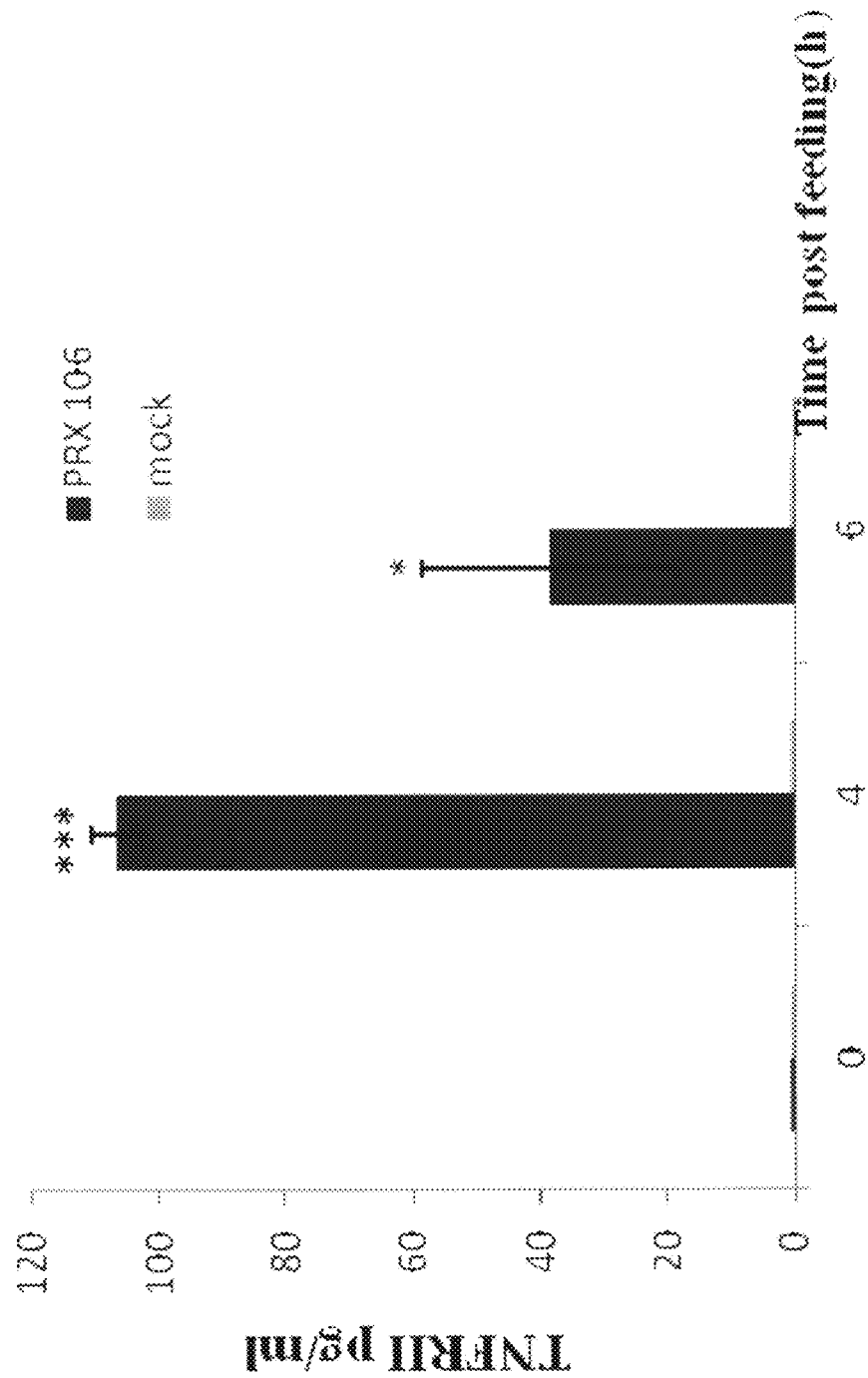

FIG. 19 is a bar graph showing pharmacokinetics of TNFR2:Fc in rat sera following oral administration of plant cells expressing recombinant TNFR2:Fc by gavage. Rats (n=6) received plant cells expressing recombinant TNFR2:Fc. Negative controls received the same volumes of host BY2(–) plant.

FIG. 20 shows the PRX-106 sequence (SEQ ID NO: 6) elucidated by mass-spec (green shown 84.8% coverage).

DESCRIPTION OF SPECIFIC EMBODIMENTS OF THE INVENTION

The present invention, in some embodiments thereof, relates to chimeric polypeptides, polynucleotides encoding same, cells expressing same and methods of producing same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Etanercept is a tumor necrosis factor (TNF) blocker indicated for a number of inflammatory conditions such as rheumatoid arthritis, polyarticular juvenile idiopathic arthritis, plaque psoriasis, psoriatic arthritis and ankylosing spondylitis. Etanercept is produced by recombinant DNA technology in Chinese hamster ovary mammalian cell expression system. The production of recombinant proteins in mammalian cell systems is hampered by cellular fragility and the complex nutritional requirements of cells and the possible contamination of the final product with virus or prions.

Whilst reducing the present invention to practice, the present inventors have constructed an expression vector for recombinant expression of Enteracept (hereinafter, prh TNFR2:Fc) in plant cells, transformed tobacco cells with the vector, and have isolated catalytically active protein from the cell cultures. The expressed recombinant protein retains its TNFα binding activity and has shown favorable catalytic activity as evidenced by its apoptosis regulatory activity.

In-vivo studies in animal models for inflammation e.g., inflammatory bowel disease, support the efficacy of the protein and specifically an oral formulation thereof in treatment of said indications.

Specifically, the effect of oral administration of prh TNFR2:Fc in plant cells on colitis was examined in two chemically-induced mouse models for IBD: (i) induced by intra-rectal administration of the covalently reactive reagents TNBS/oxazolone; and (ii) induced by injections of dextran sodium sulfate. The results shown in Examples 3A-B, below, illustrate that oral administration of plant cells expressing prh TNFR2:Fc ameliorated weight loss, significantly increased colon length, reduced colon damage (as determined histopathologically), reduced the level of secreted pro-inflammatory cytokines in-situ and in sera, and elicited splenic Treg expansion. Oral administration of plant cells expressing the chimeric polypeptide shifted the T cells population profile following treatment. Accordingly, there is a shift in the relative number of regulatory T cell and NKT cell populations upon administration of plants cells expressing the chimeric polypeptide as shown using various FACS analysis markers e.g, CD4$^+$CD25$^+$CD8$^+$CD25$^+$. CD4$^+$ CD25$^+$Foxp3$^+$ and CD3$^+$CD56$^+$ in the treated subjects.

These results conclusively show that prh TNFR2 is biologically active as an anti-inflammatory agent. The present results further support a role for orally administered plant cells expressing recombinant TNFR2:Fc as an anti-inflammatory agent with the capacity to ameliorate IBD.

The present inventors have further performed a toxicology study in animals. The results presented in Example 4 below, show that oral administration of plant cells expressing prh TNFR2:Fc is safe and well tolerated.

Thus, according to an aspect of the present invention, there is provided a plant produced chimeric polypeptide comprising:

(i) a first domain which comprises a TNFα binding domain of a TNF receptor; and (ii) a second domain which comprises an Fc domain of an immunoglobulin, wherein the first domain and the second domain are N-terminally to C-terminally respectively sequentially translationally fused and wherein the chimeric polypeptide specifically binds TNFα.

As used herein the term "plant produced" refers to the chemical signature associated with plant expression, including, but not limited to, host cell impurities in the preparation which comprises the chimeric polypeptide and glycosylation patterns on the chimeric polypeptide per se.

As used herein the term "chimeric polypeptide" refers to a protein created through the joining of two or more individual coding sequences which originally code for separate proteins. Translation of the synthetic (non-naturally occurring) nucleic acid sequence results in a single chimeric polypeptide with functional properties derived from each of the original proteins. Such recombinant fusion proteins are created artificially by recombinant DNA technology.

As used the term "TNFα" refers to Tumor necrosis factor-alpha (TNF, cachexin, or cachectin) that is a cytokine involved in systemic inflammation and a member of a group of cytokines that stimulate the acute phase reaction. TNFα is produced primarily by activated macrophages (M1), although it can be produced by many other cell types as CD4+ lymphocytes, NK cells and neurons. The protein is encoded by TNFA gene and has the Ref_seq number: NP_000585. The protein is known to stimulate an inflammatory response (pro-inflammatory cytokine).

As used herein the term "TNF receptor" or "TNFR" refers to a polypeptide which is capable of binding TNFα in a specific manner e.g., Kd below $10^{-5}$ M. According to a specific embodiment, the TNFR is membrane bound.

The first domain is thus composed of at least the TNF binding domain of a TNF receptor (TNFR). The first domain is a soluble protein. Thus according to a specific embodiment, the first domain and even the entire chimeric polypeptide are soluble proteins which are not membrane anchored.

Soluble forms of TNFRs may include monomers, fusion proteins (also called "chimeric proteins), dimers, trimers or higher order multimers. In certain embodiments of the invention, the soluble TNFR derivative is one that mimics the 75 kDa TNFR or the 55 kDa TNFR and that binds to TNFα. in vivo. The soluble TNFR mimics of the present invention may be derived from TNFRs p55 or p75 or fragments thereof. TNFRs other than p55 and p75 also are useful for deriving soluble TNFR for treating the various medical disorders described herein, such for example the TNFR that is described in WO 99/04001. Soluble TNFR molecules used to construct TNFR mimics include, for example, analogs or fragments of native TNFRs having at least 20 amino acids, that lack the transmembrane region of the native TNFR, and that are capable of binding TNFα. Such soluble forms of TNFR compete for TNFα with the receptors on the cell surface, thus inhibiting TNFα from binding to cells, thereby preventing it from manifesting its biological activities. Binding of soluble TNFRs to TNFα can be assayed using ELISA or any other convenient assay.

According to a specific embodiment, the first domain is derived from TNFR2. (e.g., AAA36755).

According to an embodiment of the invention, the first domain is 200-250 amino acids long.

According to a specific embodiment, the first domain comprises the amino acid sequence LCAP (SEQ ID NO: 11) and VFCT (SEQ ID NO: 12).

According to a specific embodiment, the first domain comprises the amino acid sequence LPAQVAFXPYAPEPG-STC (SEQ ID NO: 13), or LPAQVAFTPYAPEPGSTC (SEQ ID NO: 17).

According to a specific embodiment, the first domain is as set forth in SEQ ID NO: 2 (encoded by SEQ ID NO: 1).

As used herein "an Fc domain of an immunoglobulin" refers to a region of a heavy chain of an antibody, typically comprising at least 2 constant domains (e.g., CH2 and CH3 domains, as these terms are defined in the art) of the heavy chain. The Fc domain may be obtained, for example, in the form of a dimer, by digestion of an antibody by papain. A dimer of Fc domain polypeptides, connected by disulfide bonds, forms the "tail" region of an antibody. As is known in the art, Fc domains of some classes of antibodies may be in the form of multimers. Thus, the Fc domain is optionally monomeric, optionally dimeric and optionally multimeric. Optionally, the polypeptide described herein is in the form of a dimer, the polypeptide comprising an Fc dimer, or in the form of a multimer, the polypeptide comprising an Fc multimer.

The Fc domain may encompass modified forms of a native Fc domain (i.e., a domain which occurs naturally in an antibody), for example, polypeptides having at least 90% homology, optionally at least 95% homology, and optionally at least 98% homology, to a native Fc domain. Modified Fc domains are described, for example, in International Patent Applications WO 97/34631 and WO 96/32478.

Optionally, a native Fc is modified so as to remove sites which provide structural features or biological activity that are not required for embodiments of the present invention. Examples of such sites include residues that affect or are involved in disulfide bond formation, incompatibility with a selected host cell, N-terminal heterogeneity upon expression in a selected host cell, glycosylation, interaction with complement, binding to an Fc receptor (other than a neonatal Fc receptor), and/or antibody-dependent cellular cytotoxicity.

The polypeptide according to embodiments of the present invention may also comprise a fragment of an Fc domain. Optionally, the fragment comprises at least 20%, optionally at least 50%, and optionally at least 80% of an Fc domain, as defined hereinabove.

The Fc domain or fragment thereof optionally includes a binding site for a neonatal Fc receptor (FcRn). This is of particular significance when administering the chimeric polypeptide via an enteral route.

According to one embodiment, attachment of an Fc domain or a fragment thereof to the first domain results in a polypeptide having a longer half-life in vivo than the first domain per se. This may be due to the long serum half-life of the Fc domain (which may be due to salvage of the Fc via binding to FcRn) and/or due to the greater size of the polypeptide in comparison to the first domain per se, which reduces clearance from the bloodstream by glomerular filtration. According to another embodiment, the resulting polypeptides have reduced immunogenicity as compared to the first domain per se.

According to optional embodiments, the Fc domain or fragment thereof is a human Fc domain (e.g., derived from a human antibody) or fragment thereof.

According to exemplary embodiments, the Fc domain (or fragment thereof) is an IgG (e.g., IgG1) Fc domain (or fragment thereof).

According to a specific embodiment, the second domain is as set forth in SEQ ID NO: 9 (encoded by SEQ ID NO: 8).

Thus, the second domain of the chimeric polypeptide comprises at least a portion of a constant immunoglobulin domain, e.g. a constant heavy immunoglobulin domain or a constant light immunoglobulin domain. Preferably, the second domain comprises at least a portion of a constant heavy immunoglobulin domain. The constant heavy immunoglobulin domain is preferably an Fc fragment comprising the CH2 and CH3 domain and, optionally, at least a part of the hinge region. The immunoglobulin domain may be an IgG, IgM, IgD or IgE immunoglobulin domain or a modified immunoglobulin domain derived, therefrom. Preferably, the second domain comprises at least a portion of a constant IgG immunoglobulin domain. The IgG immunoglobulin domain may be selected from IgG1, IgG2, IgG3 of IgG4 domains or from modified domains such as are described in U.S. Pat. No. 5,925,734. The immunoglobulin domain may exhibit effector functions. In some embodiments, however, modified immunoglobulin domains having modified, e.g. at least partially deleted, effector functions may be used. Thus for example, the receptor.

According to an embodiment of the invention the chimeric fusion of the first domain and the second domain forms Etanercept (Immunex) having SEQ ID NO: 10.

It will be appreciated that the species origin of the first domain and the second domain is selected according to the treated subject. Thus, according to a specific embodiment, the first domain and the second domain are of human origin or modified such that they don't incur immunogenic reaction when administered to human subjects.

As used herein "Etanercept" and "Enbrel™" are interchangeably used to designate the commercially available TNFR2:Fc by Immunex Corporation. Etanercept is a dimeric fusion polypeptide consisting of the extracellular ligand-binding portion of the human 75 kilodalton (p75) tumor necrosis factor receptor (TNFR) linked to the Fc portion of human IgG1. The Fc component of etanercept contains the constant heavy 2 (CH2) domain, the constant heavy 3 (CH3) domain and hinge region, but not the constant heavy 1 (CH1) domain of human IgG1.

According to another embodiment of the invention there is provided a chimeric polypeptide comprising:
(i) a first domain which comprises a TNFα binding domain of a TNF receptor;
(ii) a second domain which comprises an Fc domain of an immunoglobulin; and
(iii) a third domain comprising an endoplasmic reticulum retention signal;
wherein the first domain, second domain and third domain are N-terminally to C-terminally respectively sequentially translationally fused and wherein the chimeric polypeptide specifically binds TNFα.

Thus, according to this aspect of the invention, the chimeric protein is expressed such that it is retained in the endoplasmic reticulum (ER). According to a specific embodiment, at least a portion (e.g., 20% or more) of the TNFR2:Fc molecules in the cell are retained in the ER.

As used herein, the term "endoplasmic reticulum retention signal peptide" refers to a peptide sequence which, when present at the N- or C-terminus of a polypeptide, causes the polypeptide to be retrieved from the Golgi apparatus, and retained in the endoplasmic reticulum (see Rayon et al. Journal of Experimental Botany, Vol. 49, No. 326, pp. 1463-1472, 1998; and Neumann, et al Annals of Botany, 2003; 92:167-180). In one embodiment, the endoplasmic reticulum retention signal peptide is HDEL (SEQ ID NO: 14), KDEL (SEQ ID NO: 15) or SEKDEL (SEQ ID NO: 16).

As mentioned, the first domain and second domain (and third domain when present) are N-terminally to C-terminally respectively sequentially translationally fused. This means that the first domain is located N-terminally to the second domain (the carboxy terminus of the first domain is translationally fused to the N-terminus of the second domain), and the second domain is located N-terminally of the third domain (the carboxy terminus of the second domain is translationally fused to the N-terminus of the third domain). Thus, the second domain is practically sandwiched by the first domain at the N-terminus and the third domain at the C-terminus. Schematic presentation is as follows: first domain>second domain (>third domain) are orderly oriented from the N-terminus to the C-terminus (see FIG. 1). The linkage between the domains may be direct or indirect by the use of linkers such as peptide linkers.

The molecule may further comprise an additional domain which encodes for an endoplasmic reticulum signal sequence which is oriented upstream (N-terminally) of the first domain and translationally fused thereto.

As used herein "an endoplasmic reticulum (ER) signal peptide" refers to a signal sequence, leader sequence or leader peptide that is a short (e.g., 5-30 amino acids long) peptide present at the N-terminus of the majority of newly synthesized proteins that are destined towards the secretory pathway.

According to a specific embodiment, the ER signal peptide is derived (taken) from a plant protein.

According to a specific embodiment, the endoplasmic reticulum signal peptide is from *N. plumbaginifolia* Calreticulin protein.

According to a further specific embodiment, the signal peptide from *N. plumbaginifolia* Calreticulin protein is as set forth in SEQ ID NO: 4 and encoded by the nucleic acid sequence of SEQ ID NO: 3.

As used herein the term "translationally fused at the N-terminal" or "translationally fused at the C-terminal" refers to covalent attachment of the indicated peptide via a peptide bond to the N-terminal or C-terminal amino acid of the respective domain typically as a result of recombinant expression.

According to a specific embodiment, the chimeric polypeptide is as set forth in SEQ ID NO: 6.

According to a specific embodiment, the chimeric polypeptide is as set forth in SEQ ID NO: 7, 204 or 205.

As mentioned the recombinant chimeric proteins of the invention are produced in plant cells.

In order to express the polypeptide, an isolated polynucleotide comprising a nucleic acid sequence encoding the chimeric polypeptide as described herein is ligated into a "plant nucleic acid expression construct".

As used herein the term "plant nucleic acid expression construct" refers to a nucleic acid construct which includes the nucleic acid of some embodiments of the invention and at least one promoter for directing transcription of nucleic acid in a host plant cell. Further details of suitable transformation approaches are provided hereinbelow.

According to some embodiments of the invention, there is provided a nucleic acid expression construct comprising the nucleic acid sequence of the invention, and a promoter for directing transcription of the nucleic acid sequence in a plant host cell.

As used herein the term "nucleic acid sequence" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

According to some embodiments of the present invention, the nucleic acid sequences encoding the polypeptides of the present invention are optimized for expression in plants. Examples of such sequence modifications include, but are not limited to, an altered G/C content to more closely approach that typically found in the plant species of interest, and the removal of codons atypically found in the plant species commonly referred to as codon optimization. In one embodiment, the codon usage of the nucleic acid sequence encoding the chimeric polypeptide is optimized for *Nicotiana tabacuum* or *Nicotiana benthamiana*.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1N [(Xn−Yn)/Yn]2/N, where Xn refers to the frequency of usage of codon n in highly expressed plant genes, where Yn to the frequency of usage of codon n in the gene of interest and N refers to the total number of codons in the gene of interest. A table of codon usage from highly expressed genes of dicotyledonous plants has been compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiological Sciences) DNA bank in Japan (Hypertext Transfer Protocol://World Wide Web (dot) kazusa (dot) or (dot) jp/codon/). The Codon Usage Database contains codon usage tables for a number of different species, with each codon usage table having been statistically determined based on the data present in Genbank.

By using such codon optimization tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively affect mRNA stability or expression.

The desired encoding nucleotide sequence may already, in advance of any modification, contain a number of codons that correspond to a statistically-favored codon in a particular plant species. Therefore, codon optimization of the native nucleotide sequence may comprise determining which codons, within the desired nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

Thus according to a specific embodiment, there is provided a *Nicotinia tobaccum* optimized sequence as set forth in SEQ ID NO: 5.

According to some embodiments of the invention, the nucleic acid sequence coding for the cimeric polypeptide is operably linked to a cis-acting regulatory sequence active in plant cells, such as a plant promoter sequence.

A coding nucleic acid sequence is "operably linked" to a regulatory sequence (e.g., promoter) if the regulatory sequence is capable of exerting a regulatory effect on (e.g. effect on the expression of) the coding sequence linked thereto.

Any suitable promoter sequence can be used by the nucleic acid construct of the present invention. Preferably the promoter is a constitutive promoter, a tissue-specific, or an inducible promoter.

As used herein the phrase "plant-expressible" refers to a promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. Such a promoter can be constitutive, i.e., capable of directing high level of gene expression in a plurality of tissues, tissue specific, i.e., capable of directing gene expression in a particular tissue or tissues, inducible, i.e., capable of directing gene expression under a stimulus, or chimeric, i.e., formed of portions of at least two different promoters.

Examples of preferred promoters useful for the methods of some embodiments of the invention are presented in Table I, II, III and IV.

TABLE I

Exemplary constitutive promoters for use in the performance of some embodiments of the invention

| Gene Source | Expression Pattern | Reference |
|---|---|---|
| Actin | constitutive | McElroy et al, *Plant Cell*, 2: 163-171, 1990 |
| CAMV 35S | constitutive | Odell et al, *Nature*, 313: 810-812, 1985 |
| CaMV 19S | constitutive | Nilsson et al., *Physiol. Plant* 100: 456-462, 1997 |
| GOS2 | constitutive | de Pater et al, *Plant J* Nov; 2(6): 837-44, 1992 |
| ubiquitin | constitutive | Christensen et al, *Plant Mol. Biol.* 18: 675-689, 1992 |

TABLE I-continued

Exemplary constitutive promoters for use in the performance of some embodiments of the invention

| Gene Source | Expression Pattern | Reference |
|---|---|---|
| Rice cyclophilin | constitutive | Bucholz et al, *Plant Mol Biol.* 25(5): 837-43, 1994 |
| Maize H3 histone | constitutive | Lepetit et al, *Mol. Gen. Genet.* 231: 276-285, 1992 |
| Actin 2 | constitutive | An et al, *Plant J.* 10(1); 107-121, 1996 |

TABLE II

Exemplary seed-preferred promoters for use in the performance of some embodiments of the invention

| Gene Source | Expression Pattern | Reference |
|---|---|---|
| Seed specific genes | seed | Simon, et al., *Plant Mol. Biol.* 5.191, 1985; Scofield, et al., *J. Biol. Chem.* 262: 12202, 1987.; Baszczynski, et al., *Plant Mol. Biol.* 14: 633, 1990. |
| Brazil Nut albumin | seed | Pearson' et al., *Plant Mol. Biol.* 18: 235-245, 1992. |
| legumin | seed | Ellis, et al. *Plant Mol. Biol.* 10: 203-214, 1988 |
| Glutelin (rice) | seed | Takaiwa, et al., *Mol. Gen. Genet.* 208: 15-22, 1986; Takaiwa, et al., *FEBS Letts.* 221: 43-47, 1987 |
| Zein | seed | Matzke et al *Plant Mol Biol,* 143).323-32 1990 |
| napA | seed | Stalberg, et al, *Planta* 199: 515-519, 1996 |
| wheat LMW and HMW, glutenin-1 | endosperm | *Mol Gen Genet* 216: 81-90, 1989; *NAR* 17: 461-2, |
| Wheat SPA | seed | Albani et al, *Plant Cell,* 9: 171-184, 1997 |
| wheat a, b and g gliadins | endosperm | *EMBO3*: 1409-15, 1984 |
| Barley ltr1 promoter | endosperm | |
| barley B1, C, D hordein | endosperm | *Theor Appl Gen* 98: 1253-62, 1999; *Plant J* 4: 343-55, 1993; *Mol Gen Genet* 250: 750-60, 1996 |
| Barley DOF | endosperm | Mena et al, *The Plant Journal,* 116(1): 53-62, 1998 |
| Biz2 | endosperm | EP99106056.7 |
| Synthetic promoter | endosperm | Vicente-Carbajosa et al., *Plant J.* 13: 629-640, 1998 |
| rice prolamin NRP33 | endosperm | Wu et al, *Plant Cell Physiology* 39(8) 885-889, 1998 |
| rice-globulin Glb-1 | endosperm | Wu et al, *Plant Cell Physiology* 398) 885-889, 1998 |
| rice OSH1 | embryo | Sato et al, *Proc. Nati. Acad. Sci. USA,* 93: 8117-8122 |
| rice alpha-globulin REB/OHP-1 | endosperm | Nakase et al. *Plant Mol. Biol.* 33: 513-S22, 1997 |
| rice ADP-glucose PP | endosperm | *Trans Res* 6: 157-68, 1997 |
| maize ESR gene family | endosperm | *Plant J* 12: 235-46, 1997 |
| sorghum gamma-kafirin | endosperm | *PMB* 32: 1029-35, 1996 |
| KNOX | embryo | Postma-Haarsma ef al, *Plant Mol. Biol.* 39: 257-71, 1999 |
| rice oleosin | Embryo and aleuton | Wu et at, *J. Biochem.,* 123: 386, 1998 |
| sunflower oleosin | Seed (embryo and dry seed) | Cummins, et al., *Plant Mol. Biol.* 19: 873-876, 1992 |

TABLE III

Exemplary flower-specific promoters for use in the performance of the invention

| Gene Source | Expression Pattern | Reference |
|---|---|---|
| AtPRP4 | flowers | wwwdotsalusdotmediumdotedu/mmg/tierney/html |
| chalene synthase (chsA) | flowers | Van der Meer, et al., *Plant Mol. Biol.* 15, 95-109, 1990. |
| LAT52 | anther | Twell et al *Mol. Gen Genet.* 217: 240-245 (1989) |
| apetala-3 | flowers | |

TABLE IV

Alternative rice promoters for use in the performance of the invention

| PRO # | gene | expression |
|---|---|---|
| PR00001 | Metallothionein Mte | transfer layer of embryo + calli |
| PR00005 | putative beta-amylase | transfer layer of embryo |
| PR00009 | Putative cellulose synthase | Weak in roots |
| PR00012 | lipase (putative) | |
| PR00014 | Transferase (putative) | |
| PR00016 | peptidyl prolyl cis-trans isomerase (putative) | |
| PR00019 | unknown | |
| PR00020 | prp protein (putative) | |
| PR00029 | noduline (putative) | |
| PR00058 | Proteinase inhibitor Rgpi9 | seed |
| PR00061 | beta expansine EXPB9 | Weak in young flowers |
| PR00063 | Structural protein | young tissues + calli + embryo |
| PR00069 | xylosidase (putative) | |
| PR00075 | Prolamine 10 Kda | strong in endosperm |
| PR00076 | allergen RA2 | strong in endosperm |
| PR00077 | prolamine RP7 | strong in endosperm |
| PR00078 | CBP80 | |
| PR00079 | starch branching enzyme I | |
| PR00080 | Metallothioneine-like ML2 | transfer layer of embryo + calli |
| PR00081 | putative caffeoyl-CoA 3-0 methyltransferase | shoot |
| PR00087 | prolamine RM9 | strong in endosperm |
| PR00090 | prolamine RP6 | strong in endosperm |
| PR00091 | prolamine RP5 | strong in endosperm |
| PR00092 | allergen RA5 | |
| PR00095 | Putative methionine aminopeptidase | embryo |
| PR00098 | ras-related GTP binding protein | |
| PR00104 | beta expansine EXPB1 | |
| PR00105 | Glycine rich protein | |
| PR00108 | metallothionein like protein (putative) | |
| PR00110 | RCc3 | strong root |
| PR00111 | uclacyanin 3-like protein | weak discrimination center/ shoot meristem |
| PR00116 | 26S proteasome regulatory particle non-ATPase subunit 11 | very weak meristem specific |
| PR00117 | putative 40S ribosomal protein | weak in endosperm |
| PR00122 | chlorophyll a/lo-binding protein precursor (Cab27) | very weak in shoot |
| PR00123 | putative protochlorophyllide reductase | Strong leaves |
| PR00126 | metallothionein RiCMT | strong discrimination center shoot meristem |
| PR00129 | GOS2 | Strong constitutive |
| PR00131 | GOS9 | |
| PR00133 | chitinase Cht-3 | very weak meristem specific |
| PR00135 | alpha-globulin | Strong in endosperm |
| PR00136 | alanine aminotransferase | Weak in endosperm |
| PR00138 | Cyclin A2 | |
| PR00139 | Cyclin D2 | |

TABLE IV-continued

Alternative rice promoters for use in the performance of the invention

| PRO # | gene | expression |
|---|---|---|
| PR00140 | Cyclin D3 | |
| PR00141 | Cyclophyllin 2 | Shoot and seed |
| PR00146 | sucrose synthase SS1 (barley) | medium constitutive |
| PR00147 | trypsin inhibitor ITR1 (barley) | weak in endosperm |
| PR00149 | ubiquitine 2 with intron | strong constitutive |
| PR00151 | WSI18 | Embryo and stress |
| PR00156 | HVA22 homologue (putative) | |
| PR00157 | EL2 | |
| PR00169 | aquaporine | medium constitutive in young plants |
| PR00170 | High mobility group protein | Strong constitutive |
| PR00171 | reversibly glycosylated protein RGP1 | weak constitutive |
| PR00173 | cytosolic MDH | shoot |
| PR00175 | RAB21 | Embryo and stress |
| PR00176 | CDPK7 | |
| PR00177 | Cdc2-1 | very weak in meristem |
| PR00197 | sucrose synthase 3 | |
| PR00198 | OsVP1 | |
| PR00200 | OSH1 | very weak in young plant meristem |
| PR00208 | putative chlorophyllase | |
| PR00210 | OsNRT1 | |
| PR00211 | EXP3 | |
| PR00216 | phosphate transporter OjPT1 | |
| PR00218 | oleosin 18 kd | aleurone + embryo |
| PR00219 | ubiquitine 2 without intron | |
| PR00220 | RFL | |
| PR00221 | maize UBI delta intron | not detected |
| PR00223 | glutelin-1 | |
| PR00224 | fragment of prolamin RP6 promoter | |
| PR00225 | 4xABRE | |
| PR00226 | glutelin OSGLUA3 | |
| PR00227 | BLZ-2_short (barley) | |
| PR00228 | BLZ-2_long (barley) | |

The nucleic acid construct of some embodiments of the invention can further include an appropriate selectable marker and/or an origin of replication. According to some embodiments of the invention, the nucleic acid construct utilized is a shuttle vector, which can propagate both in *E. coli* (wherein the construct comprises an appropriate selectable marker and origin of replication) and be compatible with propagation in cells. The construct according to the present invention can be, for example, a plasmid, a bacmid, a phagemid, a cosmid, a phage, a virus or an artificial chromosome.

The nucleic acid construct of some embodiments of the invention can be utilized to stably or transiently transform plant cells. In stable transformation, the nucleic acid is integrated into the plant genome and as such it represents a stable and inherited trait. In transient transformation, the exogenous polynucleotide is expressed by the cell transformed but it is not integrated into the genome and as such it represents a transient trait.

Thus, according to some aspects of the present invention, there is provided an isolated cell comprising the nucleic acid construct of the invention.

As used herein, the term "isolated cell" refers to a cell at least partially separated from the natural environment e.g., from a plant. In some embodiments, the isolated cell is a plant cell of a whole plant. In some embodiments, the isolated cell is a plant cell, for example, a plant cell in culture.

The term "plant" as used herein encompasses whole plants, ancestors and progeny of the plants and plant parts, including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalypfus* spp., *Euclea schimperi*, *Eulalia vi/losa*, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativam*, *Podocarpus totara*, *Pogonarthria fleckii*, *Pogonaffhria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barley, rye, oat, peanut, pea, lentil and alfalfa, cotton, rapeseed, canola, pepper, sunflower, tobacco, eggplant, *eucalyptus*, a tree, an ornamental plant, a perennial grass and a forage crop. Alternatively algae and other non-Viridiplantae can be used for the methods of the present invention.

According to some embodiments of the invention, the plant or plant cell is a duckweed plant, cell or nodule. Duckweed (members of the monocotyledonous family Lemnaceae, or *Lemna*) plant or duckweed nodule cultures can be efficiently transformed with an expression cassette containing a nucleotide sequence of interest by any one of a number of methods including *Agrobacterium*-mediated gene transfer, ballistic bombardment, or electroporation. Methods for molecular engineering of duckweed cells and detailed description of duckweed expression systems useful for commercial production of polypeptides are known in the art (see, for example, U.S. Pat. Nos. 6,040,498 and 6,815,184 to Stomp, et al, and 8,022,270 to Dickey et al, all of which are incorporated fully by reference herein).

According to some embodiments of the invention, the plant or plant cell used by the method of the invention is a crop plant or cell of a crop plant such as rice, maize, wheat, barley, peanut, potato, sesame, olive tree, palm oil, banana, soybean, sunflower, canola, sugarcane, alfalfa, millet, leguminosae (bean, pea), flax, *lupinus*, rapeseed, tobacco, poplar and cotton.

According to further embodiments the plant cells includes tobacco cells, *Agrobacterium rhizogenes* transformed root cell, celery cell, ginger cell, horseradish cell and carrot cells. In one embodiment the tobacco cells are from a tobacco cell line, such as, but not limited to *Nicotiana tabacum* L. cv Bright Yellow (BY-2) cells. The plant cells may be grown according to any type of suitable culturing method, including but not limited to, culture on a solid surface (such as a plastic culturing vessel or plate for example) or in suspension. It will be noted that some cells, such as the BY-2 and carrot cells can be cultured and grown in suspension. Suitable devices and methods for culturing plant cells in suspension are known in the art, for example, as described in International Patent Application PCT IL2008/000614. In yet another embodiment the cells are cells of whole tobacco plants or plant tissues, including, but not limited to *Nicotiana benthamiana*.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

According to some embodiments of the invention, the transgenic plants are generated by transient transformation of leaf cells, meristematic cells or the whole plant.

Transient transformation can be effected by any of the direct DNA transfer methods described above or by viral infection using modified plant viruses.

Viruses that have been shown to be useful for the transformation of plant hosts include CaMV, Tobacco mosaic virus (TMV), brome mosaic virus (BMV) and Bean Common Mosaic Virus (BV or BCMV). Transformation of plants using plant viruses is described in U.S. Pat. No. 4,855,237 (bean golden mosaic virus; BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants are described in WO 87/06261.

According to some embodiments of the invention, the virus used for transient transformations is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols: From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; Takamatsu et al. FEBS Letters (1990) 269:73-76; and U.S. Pat. No. 5,316,931.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984;

Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the nucleic acid sequence includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

According to some embodiments of the invention, the method further comprises growing the plant cell expressing the nucleic acid. The plant cells can be any plant cells desired. The plant cells can be cultured cells, cells in cultured tissue or cultured organs, or cells in a plant. In some embodiments, the plant cells are cultured cells, or cells in cultured tissue or cultured organs. In yet further embodiments, the plant cells are any type of plant that is used in gene transference. The plant cell can be grown as part of a whole plant, or, alternatively, in plant cell culture.

According to some aspects of the invention, the plant cells are grown in a plant cell suspension culture. As used herein, the term "suspension culture" refers to the growth of cells separate from the organism. Suspension culture can be facilitated via use of a liquid medium (a "suspension medium"). Suspension culture can refer to the growth of cells in liquid nutrient media. Methods and devices suitable for growing plant cells of the invention in plant cell suspension culture are described in detail in, for example, PCT WO2008/135991, U.S. Pat. No. 6,391,683, U.S. patent application Ser. No. 10/784,295; International Patent Publications PCT Nos. WO2004/091475, WO2005/080544 and WO 2006/040761, all of which are hereby incorporated by reference as if fully set forth herein.

Thus, the invention encompasses plants or plant cultures expressing the nucleic acid sequences, so as to produce the recombinant chimeric polypeptide of the invention. Once expressed within the plant cell or the entire plant, the level of the chimeric polypeptide encoded by the nucleic acid sequence can be determined by methods well known in the art such as, activity assays, Western blots using antibodies capable of specifically binding the chimeric polypeptide (anti TNFR2, and anti Fc, See Examples section which follows), Enzyme-Linked Immuno Sorbent Assay (ELISA), radio-immuno-assays (RIA), immunohistochemistry, immunocytochemistry, immunofluorescence and the like.

Methods of determining the level in the plant of the RNA transcribed from the nucleic acid sequence are well known in the art and include, for example, Northern blot analysis, reverse transcription polymerase chain reaction (RT-PCR) analysis (including quantitative, semi-quantitative or real-time RT-PCR) and RNA-in situ hybridization.

According to some embodiments of the invention, the expressed recombinant chimeric polypeptide of the present invention is glycosylated in the plant cell, resulting in a chimeric polypeptide having one, or two or three or more glycan structures having plant specific glycan residues. Thus, according to some embodiments of the invention, the cells expressing the expression vector of the invention produce a chimeric polypeptide having various amounts of glycan structures arranged in one, two, three or more antennae. All structures may contain a core structure of two GlcNAcs and one mannose, and variations of different amounts of mannose, in addition to core alpha (1,3) fucose, beta (1,2) xylose, and/or GlcNAc residues. Structures can be of the high mannose type, having at least one, optionally at least two, optionally at least three or optionally at least four or more mannose residues in addition to the core structure; or complex type having both mannose and other glycan types on each glycan, or of the hybrid type having both high mannose and complex antennae.

In other embodiments the cells expressing the expression vector of the invention produce a chimeric polypeptide having at least one, optionally at least two, optionally at least three or optionally at least four or more core xylose residues. In yet other embodiments the cells expressing the expression vector of the invention produce a chimeric polypeptide having at least one, optionally at least two, optionally at least three or optionally at least four or more core $\alpha$-(1,3) fucose residues. In one embodiment the cells expressing the expression vector of the invention produce a chimeric polypeptide protein having at least one exposed mannose residue, at least one core xylose residue and at least one $\alpha$-(1,3) fucose residue. In yet further embodiments, the cells expressing the expression vector of the invention produce a chimeric polypeptide having at least one, at least two, at least 3 or more terminal N-acetyl glucosamine substitutions on the outer mannose sugars.

According to a specific embodiment the chimeric polypeptide lacks sialic acid residues. Yet further according to a specific embodiment, the chimeric polypeptide comprises at least 40%, 45%, 50%, 55%, 60%, 65%, 70% or more complex glycans. According to a specific embodiment, the chimeric polypeptide comprises 40-70% complex glycans.

Purification of the secreted plant cell-expressed human chimeric polypeptide from the cell yields a highly purified composition comprising the prhTNFR2:Fc (also referred to herein as TNFR2:Fc or PRX-106). Thus, in some embodiments the chimeric polypeptide protein is purified to a homogeneity of at least 98%. Thus the purified preparation is characterized by a purity of at least 85%, at least 87%, at least 90%, at least 91%, at least 91.5%, at least 92%, at least 92.5%, at least 93%, at least 93.1%, at least 93.2%, at least 93.3%, at least 93.4%, at least 93.5%, at least 93.6%, at least 93.7%, at least 93.8%, at least 93.9%, at least 94%, at least 94.5%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, in a range of at least 95.0-99.8% or 100% purity. In some embodiments, purity of the chimeric polypeptide is measured by HPLC.

In some embodiments the plant-expressed chimeric polypeptide preparation comprises impurities derived from the plant host cell, such as, but not limited to nucleic acids and polynucleotides, amino acids, oligopeptides and polypeptides, glycans and other carbohydrates, lipids and the like. In some embodiments the host-cell derived impurities comprise biologically active molecules, such as enzymes. In other embodiments, the plant-expressed chimeric polypeptide composition comprises plant beta-N-acetylhexosaminidase. Where the host cell is a tobacco cell, or tobacco cell line cell, the plant beta-N-acetylhexosaminidase is a tobacco beta-N-acetylhexosaminidase.

In further embodiments the plant beta-N-acetylhexosaminidase is inactivated plant beta-N-acetylhexosaminidase. Inactivation of plant beta-N-acetylhexosaminidase can be effected by physical means, chemical means or biochemical means. Physical inactivation can be performed by heating, freezing, desiccation, etc. Chemical inactivation can be performed by extremes of pH, chemical denaturation, addition or removal of side chains, glycans, amino acids, etc. Biochemical inactivation includes, but is not limited to inhibition by reversible or irreversible inhibitors. Exemplary beta-N-acetylhexosaminidase inhibitors include end-product inhibitors such as N-acetyl-D-glucosamine and beta-methyl-N-acetyl glucosamine, and selective inhibitors such as the compounds disclosed in US Patent Applications US2010016386, US20110237631, US20100087477 and US20120046337. It will be appreciated that preferred methods for inhibition and/or inactivation of the plant beta-N-acetylhexosaminidase are those which also effectively preserve the structural and functional integrity of the plant-expressed chimeric polypeptide.

In some embodiments the plant beta-N-acetylhexosaminidase is inactivated by heating the composition comprising the chimeric polypeptide. Suitable temperatures for plant beta-N-acetylhexosaminidase inhibition and/or activation include heating within a range of 37-60° C. for a period of 2 to 5, 10, 20, 30, 40, 50, 60 or more minutes. It will be appreciated that effective inhibition and/or inactivation of the plant beta-N-acetylhexosaminidase is achieved more rapidly at higher temperatures and more slowly at lower temperatures of the range. In some embodiments, the plant-expressed chimeric polypeptide composition is heated in the range of 45-55° C. for 2-10 minutes. In some embodiments, the inhibition/inactivation results in 20, 30, 40, 50, 60, 70, 80% or greater inactivation of the plant beta-N-acetylhexosaminidase.

The chimeric polypeptide of the invention is utilized for the treatment of TNFα-associated medical conditions.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein "a TNFα-associated medical condition" refers to a medical condition in which TNFα activity is associated with onset, progression of the medical conditions and/or related symptoms in a subject.

Thus, TNFα-associated medical condition disease, in a cell, tissue, organ, animal, or subject in need thereof including, but not limited to, at least one of obesity, an immune related disease, a cardiovascular disease, an infectious disease, a malignant disease or a neurologic disease (see WO0212502).

Specific examples of a TNFα-associated medical condition include, but are not limited to, rheumatoid arthritis, psoriatic arthritis, ankylosing spondylitis, Wegener's disease (granulomatosis), Crohn's disease, inflammatory bowel disease, short bowel syndrome, cholitis, ulcerative cholitis, chronic obstructive pulmonary disease (COPD), Hepatitis C, endometriosis, asthma, cachexia, psoriasis, and atopic dermatitis. Additional diseases or disorders that can be treated with the chimeric polypeptide of the invention include those described in WO 00/62790, WO 01/62272 and U.S. Patent Application No. 2001/0021380, U.S. Pat. No. 7,648,702, the relevant portions of which are incorporated herein by reference.

Other examples of TNFα-associated medical conditions include, but are not limited to those disclosed in Kuek et al. *Postgrad. Med. J.* 2007; 83; 251-260, which is herein incorporated by reference in its entirety.

Thus, exemplary indications include, Sjorgen's syndrome, polymyositis, dermatomyositis, Wegener's vasculitis, Bechet's, giant cell arteritis (GCA), Polymyalgia rheumatic, Takayasu's arteritis, Polyarteritis *nodosa*, Sarcoidosis, adult onset Still's disease, Kawasaki disease, Cryoglobulinemic vasculitis, relapsing polychondritis, Hidradenitis suppurativa, Coeliac disease, myelodysplastic syndromes, Pyoderma gangrenosum, Erythema nodosum, SAPHO syndrome, graft versus host disease, chronic hepatitis B/C, thrombic/idiopathic thrombocytopenic purpura, refractory asthma, lupus, amyloidosis, Multicentric reticulohistiocytosis, pemphigus, Grave's disease, antiphospholipid syndrome, idiopathic membranous glomerulonephritis, Hep C associated glomerulonephritis, myasthenia gravis and multiple sclerosis.

According to a specific embodiment, TNFα-associated medical condition is an inflammatory bowel disease. According to a specific embodiment, the polypeptide is administered enterally, e.g., orally, such as comprised in the plant cells.

According to a specific embodiment, the inflammatory bowel disease is ulcerative colitis or Crohn's disease. According to a specific embodiment, the polypeptide is administered enterally, e.g., orally, such as comprised in the plant cells.

Additional examples of TNFα-associated medical condition include, but are not limited to, immune related disease, such as rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, short bowel syndrome, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions-, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g, including but not limited toasthenia, anemia, cachexia, and the like), chronic salicylate intoxication, and the like. See, e.g, the Merck Manual, 12th-17th Editions, Merck & Company, Rahway, N.J. (1972, 1977, 1982, 1987, 1992, 1999), Pharmacotherapy Handbook, Wells et al, eds. Second Edition, Appleton and Lange, Stamford, Conn. (1998, 2000), each entirely incorporated by reference. The present invention also provides a method for treating at least one cardiovascular disease in a cell, tissue, organ, animal, or patient, including, but not limited to, at least one of cardiac stun syndrome, myocardial infarction, congestive heart failure, stroke, ischemic stroke, hemorrhage, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occulsion of the abdominal aorta and its branches, peripheral vascular disorders, occulsive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like.

Additional examples of a TNFα-associated medical condition include, but are not limited to, infectious diseases, such as acute or chronic bacterial infection, acute and chronic parasitic or infectious processes, including bacterial, viral and fungal infections, HIV infection/HIV neuropathy, meningitis, hepatitis (A,B or C, or the like), septic arthritis, peritonitis, pneumonia, epiglottitis, *e. coli* 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium intracellulare, pneumocystis carinii* pneumonia, pelvic inflammatory disease, orchitis/epidydimitis, *legionella*, lyme disease, influenza a, epstein-barr virus, vital-associated hemaphagocytic syndrome, vital encephalitis/aseptic meningitis, and the like.

Additional examples of a TNFα-associated medical condition include, but are not limited to, malignant diseases such as leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), hairy cell leukemia, myelodyplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain, and the like.

Additional examples of a TNFα-associated medical condition include, but are not limited to, neurologic diseases, such as neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multisystem disorder); demyelinating core disorders, such as multiple sclerosis, acute transverse myelitis; and disorders of the motor unit, such as neurogenic muscular atrophies (anterior horn cell degeneration, such as amyofrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like.

As used herein, the term "subject" includes mammals, e.g., human beings at any age which suffer from the pathology. According to a specific embodiment, this term encompasses individuals who are at risk to develop the pathology.

It has been shown that plant cells expressing biologically active human recombinant polypeptides can be used as an effective systemic delivery system, when provided for enteral administration to the subject (see WO2007/010533). Thus, in some embodiments, the chimeric polypeptide can be formulated in a pharmaceutical composition for oral or enteral delivery comprising transformed plant cell expressing the chimeric polypeptide and a pharmaceutically acceptable carrier. In some embodiments, the transformed plant cells of the pharmaceutical composition are lyophilized plant cells.

As used herein the phrase "enteral administration" refers to administration through any part of the gastro-intestinal tract, such as rectal administration, colonic administration, intestinal administration (proximal or distal) and gastric administration. In some embodiments, enteral administration refers to oral administration.

It will be appreciated that the present teachings are also directed at mucosal administration of plant cells expressing the chimeric polypeptide of the invention.

The cells may be formulated as a solid, formulated as a liquid or formulated as a powder. In some embodiments, the cells are resuspended, lyophilized cells.

Thus, in some embodiments, the chimeric polypeptide can be formulated in a pharmaceutical composition for oral or enteral delivery comprising transformed plant cell expressing the chimeric polypeptide and a pharmaceutically acceptable carrier. In some embodiments, the transformed plant cells of the pharmaceutical composition are lyophilized plant cells, although the use of fresh (non-lyophilized cells), plant tissues, plant parts or whole plants is also contemplated herein.

Prior to lyophilization the cells may be washed to remove any cell debris that may be present in the growth medium.

As the cells are being prepared for lyophilization, it is sometimes desirable to incubate the cells in a maintenance medium to reduce the metabolic processes of the cells.

Pretreatment (although not necessary) can be performed at room temperature or at temperatures in which the plant cells are typically cultured. Pretreatment is performed at about room temperature (20° C.) for ease of handling and as most plant cells are fairly stable at room temperature. Stabilizers can be added directly to the medium and replenished as necessary during the pretreatment process.

Pretreatments may also involve incubating cells in the presence of one or more osmotic agents. Examples of useful osmotic agents include sugars such as saccharides and saccharide derivatives, amino or imino acids such as proline and proline derivatives, or combinations of these agents. Some of the more useful sugars and sugar derivatives are fructose, glucose, maltose, mannitol, sorbitol, sucrose and trehalose. Osmotic agents are utilized at a concentration that prepares cells for subsequent lyophilization.

Lyophilization is directed at reducing the water content of the cells by vacuum evaporation. Vacuum evaporation involves placing the cells in an environment with reduced air pressure. Depending on the rate of water removal desired, the reduced ambient pressure operating at temperatures of between about −30° C. to −50° C. may be at 100 torr, 1 torr, 0.01 torr or less. According to a specific embodiment, the cells are lyophilized by freezing to −40° C. and then applying a vacuum to a pressure of 0.1 mbar. The cells are then heated to −10° C. so all the ice content will be sublimated and evaporated. Under conditions of reduced pressure, the rate of water evaporation is increased such that up to 60-95% of the water in a cell can be removed.

According to a specific embodiment, lyophilization removes over 60%, 70%, 80% or specifically over 90%, 91%, 92%, 93%, 94%, 95% or 98% of the water from the cells. According to a specific embodiment, the final water content is about 5-10%, 5-8% or 6-7%.

Thus, the oral dosage form may be provided as an oral nutritional form (e.g., as long as the protein is not exposed to denaturing conditions which include heating above 37° C. and compression), as a complete meal, as a powder for dissolution, e.g. health drinks, as a solution, as a ready-made drink, optionally low calorie, such as a soft drink, including juices, milk-shake, yoghurt drink, smoothie or soy-based drink, in a bar, or dispersed in foods of any sort, such as baked products, cereal bars, dairy bars, snack-foods, breakfast cereals, muesli, candies, tabs, cookies, biscuits, crackers (such as a rice crackers), chocolate, and dairy products.

Of note is the use of plant cells expressing the chimeric polypeptide in the treatment of inflammatory bowel disease. The plant's cell wall is expected to protect the chimeric polypeptide while moving through the stomach and small intestine. In the colon, where the polysaccharides are digested, the plant cell is expected to release its content and hence prh TNRF:Fc is available to bind its cytokine ligand. Moreover, prh TNRF2:Fc is a chimeric protein carries an Fc segment of human IgG1. In the epithelial monolayer lining the mucosal barrier, the FcRn receptor transcytoses IgG molecules across by binding to their Fc. Therefore, prh TNRF:Fc can also cross the epithelial barrier to bind its cytokine ligand on the serosal side of the epithelia.

It will be appreciated that the present teachings exclude the use of plant cells expressing the chimeric polypeptide by enteral administration for the treatment of medical conditions directly associated with obesity, metabolic syndrome, diabetes and a liver disease or disorder.

The metabolic syndrome is a constellation of interrelated risk factors of metabolic origin—metabolic risk factors—that appear to directly promote the development of atherosclerotic cardiovascular disease (ASCVD). Patients with the metabolic syndrome also are at increased risk for developing type 2 diabetes mellitus. The multiple components and criteria that define the metabolic syndrome have varied somewhat in specific elements, but in general they include a combination of both underlying and metabolic risk factors. The most widely recognized of the metabolic risk factors are atherogenic dyslipidemia, elevated blood pressure, and elevated plasma glucose. Individuals with these characteristics commonly manifest a prothrombotic state and a proinflammatory state as well. Atherogenic dyslipidemia consists of an aggregation of lipoprotein abnormalities including elevated serum triglyceride and apolipoprotein B (apoB), increased small LDL particles, and a reduced level of HDL cholesterol (HDL-C). Available data suggest that it truly is a syndrome, i.e., a grouping of ASCVD risk factors, but one that probably has more than one cause.

According to a specific embodiment, the liver disease or disorder is selected from the group consisting of hepatitis, liver cirrhosis, liver cancer, hepatotoxicity, chronic liver disease, fatty liver disease and non-alcoholic steatohepatitis (NASH).

According to a specific embodiment, when the TNFR2:Fc is administered enterally (e.g., orally) in plant cells, the medical condition is not an obesity, metabolic syndrome, diabetes and a liver disease or disorder.

According to a specific embodiment, the hepatotoxicity is induced by a chemical agent selected from the group consisting of acetaminophen, NSAIDS, glucocorticoid, isoniazid, arsenic, chemotherapy, carbon tetrachloride and vinyl chloride.

According to a specific embodiment, the diabetes is selected from the group consisting of type I diabetes, type II diabetes and LADA disease.

Alternatively or additionally, the chimeric polypeptide of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the chimeric polypeptide or cells expressing same accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

The pharmaceutical compositions of this invention are particularly useful for parenteral administration, i.e., subcutaneously, intramuscularly, intravenously, intraperitoneal, intracerebrospinal, intra-articular, intrasynovial, and/or intrathecal. Parenteral administration can be by bolus injection or continuous infusion. Pharmaceutical compositions for injection may be presented in unit dosage form, e.g., in ampoules or in multi-dose containers, with an added preservative. In addition, a number of recent drug delivery approaches have been developed and the pharmaceutical compositions of the present invention are suitable for administration using these new methods, e.g., Inject-Ease™, Genject™, injector pens such as GenPen™, and needleless devices such as MediJector™ and BioJector™.

The pharmaceutical composition can also be formulated as a depot preparation. Such long acting formulations may be administered by implantation (for example subcutaneously or intramuscularly) or by intramuscular injection. Thus, for example, the formulations may be modified with suitable polymeric or hydrophobic materials (for example as an emulsion in an acceptable oil) or ion exchange resins, or as sparingly soluble derivatives, for example, as a sparingly soluble salt.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (chimeric polypeptide) effective to prevent, alleviate or ameliorate symptoms of a disorder or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide the chimeric polypeptide (the target tissue) levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

In one embodiment, the effective chimeric polypeptide amount per adult dose ranges from about 1-500 mg/m$^2$, or from about 1-200 mg/m$^2$, or from about 1-40 mg/m$^2$ or about 5-25 mg/m$^2$. Alternatively, a flat dose may be administered, whose amount may range from 2-500 mg/dose, 2-100 mg/dose or from about 10-80 mg/dose.

In one embodiment, the effective chimeric polypeptide amount per adult dose is about 1-500 mg/m$^2$, or about 1-200 mg/m$^2$, or about 1-40 m g/m$^2$ or about 5-25 mg/m$^2$. Alternatively, a flat dose may be administered, whose amount may range about 2-500 mg/dose, 2-100 mg/dose or from about 10-80 mg/dose.

In another embodiment the effective chimeric polypeptide amount per adult dose range is about 0.0002 mg/kg to 2 mg/kg, about 0.002-2 mg/kg, about 0.02-2 mg/kg, about 0.2-2 mg/kg, about 0.002-0.2 mg/kg, about 0.0002-1 mg/kg, about 0.002-0.1 mg/kg, about 0.002-0.02 mg/kg, about 0.002-0.01 mg/kg, about 0.002-0.008 mg/kg, about 0.02-0.1 mg/kg, about 0.001-0.05 mg/kg, about 0.001-0.01 mg/kg, about 0.01-1 mg/kg, about 0.01-15 mg/kg, about 0.005-1 mg/kg, about 0.01-5 mg/kg, about 0.005-0.01 mg/kg or about 0.05-0.1 mg/kg. According to a further specific embodiment, the effective chimeric polypeptide amount per adult dose range is about 0.02-0.3 mg/kg, 0.02-0.7 mg/kg, 0.02-0.247 mg/kg, 0.02-0.12 mg/kg, 0.12-0.24 mg/kg, 0.02-0.1 mg/kg or 0.15-0.247 mg/kg.

According to a specific embodiment, these dose ranges are used for oral administration such as of plant cells expressing the chimeric protein.

According to a specific embodiment, the effective chimeric polypeptide amount per adult dose ranges about 0.002-0.2 mg/kg or 0.02-0.3 mg/kg. According to a specific embodiment the effective chimeric polypeptide amount per adult dose ranges about 0.02-0.3 mg/kg, 0.02-0.27 mg/kg or 0.02-0.247 mg/kg. According to a specific embodiment, this dose range is used for oral administration such as of plant cells expressing the chimeric protein.

Alternatively, a flat dose may be administered, whose amount may range about 2-500 mg/dose, 2-100 mg/dose or from 10-80 mg/dose. According to a specific embodiment, this dose range is used for oral administration such as of plant cells expressing the chimeric protein.

According to a specific embodiment, a flat dose of 0.01-100 mg, 0.1-100 mg, 0.1-50 mg, 1-20 mg, 1-10 mg, 10-20 mg, 15-20 mg, 0.1-20 mg, 0.1-10 mg, 0.1-5 mg is administered. According to a specific embodiment, this dose range is used for oral administration such as of plant cells expressing the chimeric protein.

Any of these doses can be packed in a unit dosage form which comprises plant cells expressing (per batch and not per cell) the polypeptide in an amount of 1-20 mg, 1-10 mg, 10-20 mg or 15-20 mg.

According to a specific embodiment the flat dose is about 0.1-10 mg. According to a specific embodiment, this dose range is used for oral administration such as of plant cells expressing the chimeric protein.

According to a specific embodiment, the oral dose is administered daily. The dose may be divided for a number of administrations during the day (say 2-4 times a day). The dose can also be administered every two days, two times a week, three times a week, biweekly, weekly doses, or separated by several weeks (for example 2 to 8).

According to a specific embodiment, if the dose is to be administered more than one time per week, an exemplary dose range is the same as the foregoing described dose ranges or lower and administered two or more times per week (e.g., 25-100 mg/dose). In another embodiment, an acceptable dose for administration by injection contains 80-100 mg/dose, or alternatively, containing 80 mg per dose.

The dose may be modified for children and infants.

The dose can be administered at biweekly, weekly doses, or separated by several weeks (for example 2 to 8). According to a specific embodiment the chimeric polypeptide is generally administered at 25 mg by a single subcutaneous (SC) injection.

In many instances, an improvement in a patient's condition will be obtained by a dose of up to about 100 mg of the pharmaceutical composition one to three times per week over a period of at least three weeks, though treatment for longer periods may be necessary to induce the desired degree of improvement. For incurable chronic conditions the regimen may be continued indefinitely. For pediatric patients (ages 4-17), a suitable regimen involves a dose of 0.4 mg/kg to 5 mg/kg of the chimeric polypeptides of the invention by injection, administered one or more times per week.

In another embodiment, it is contemplated that the pharmaceutical formulation of the invention is prepared in a bulk formulation and as such, the components of the pharmaceutical composition are adjusted so that it is higher than would be required for administration and diluted appropriately prior to administration.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above. The concentration of the polypeptide in the aqueous pharmaceutical composition can vary over a wide range, but is generally within the range of from about 0.05 to about 20,000 micrograms per milliliter µ/ml) of aqueous formulation.

Of note dosage forms which comprise the plant cells may include additives such as one or more of calcium, magnesium, iron, zinc, phosphorus, vitamin D and vitamin K. A suitable daily amount is 0.1 mg to 3.6 g calcium, preferably 320 to 530 mg. In general, the daily dosage of vitamins and minerals in the nutritional formulation or medicament of the invention is 25-100% by weight of the dosages recommended by the health authorities. Dietary fiber may also be a component of the compositions of the invention. Further components of the supplement may include any bioactive compounds or extracts which are known to have health benefits, especially for improving physical performance.

Generally the unit dosage form may further comprise an antioxidant (exemplary embodiments are provided above. In another embodiment, the antioxidant is a pharmaceutically acceptable antioxidant. In another embodiment, the antioxidant is selected from the group consisting of vitamin E, superoxide dismutase (SOD), omega-3, and beta-carotene.

In another embodiment, the unit dosage form further comprises an enhancer of the biologically active protein or peptide. In another embodiment, the unit dosage form further comprises a cofactor of the biologically active protein or peptide.

In another embodiment, a unit dosage form of the present invention further comprises pharmaceutical-grade surfactant. Surfactants are well known in the art, and are described, inter alia, in the Handbook of Pharmaceutical Excipients (eds. Raymond C Rowe, Paul J Sheskey, and Sian C Owen, copyright Pharmaceutical Press, 2005). In another embodiment, the surfactant is any other surfactant known in the art.

In another embodiment, a unit dosage form of the present invention further comprises pharmaceutical-grade emulsifier or emulgator (emollient). Emulsifiers and emulgators are well known in the art, and are described, inter alia, in the Handbook of Pharmaceutical Excipients (ibid). Non-limiting examples of emulsifiers and emulgators are eumulgin, Eumulgin B1 PH, Eumulgin B2 PH, hydrogenated castor oil cetostearyl alcohol, and cetyl alcohol. In another embodiment, the emulsifier or emulgator is any other emulsifier or emulgator known in the art.

In another embodiment, a unit dosage form of the present invention further comprises pharmaceutical-grade stabilizer. Stabilizers are well known in the art, and are described, inter alia, in the Handbook of Pharmaceutical Excipients (ibid). In another embodiment, the stabilizer is any other stabilizer known in the art.

In another embodiment, a unit dosage form of the present invention further comprises an amino acid selected from the group consisting of arginine, lysine, aspartate, glutamate, and histidine. In another embodiment, analogues and modified versions of arginine, lysine, aspartate, glutamate and histidine are included in the terms "arginine," "lysine," "aspartate", "glutamate" and "histidine," respectively. In another embodiment, the amino acid provides additional protection of ribonuclease or other active molecules. In another embodiment, the amino acid promotes interaction of biologically active protein or peptide with a target cell. In another embodiment, the amino acid is contained in an oil component of the unit dosage form.

In another embodiment, a unit dosage form of the present invention further comprises one or more pharmaceutically acceptable excipients, into which the matrix carrier unit dosage form is mixed. In another embodiment, the excipients include one or more additional polysaccharides. In another embodiment, the excipients include one or more waxes. In another embodiment, the excipients provide a desired taste to the unit dosage form. In another embodiment, the excipients influence the drug consistency, and the final dosage form such as a gel capsule or a hard gelatin capsule.

Non limiting examples of excipients include: Antifoaming agents (dimethicone, simethicone); Antimicrobial preservatives (benzalkonium chloride, benzelthonium chloride, butylparaben, cetylpyridinium chloride, chlorobutanol, chlorocresol, cresol, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Chelating agents (edetate disodium, ethylenediaminetetraacetic acid and salts, edetic acid); Coating agents (sodium carboxymethyl-cellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolmaide, oxyquinoline sulfate); Desiccants (calcium chloride, calcium sulfate, silicon dioxide); Emulsifying and/or solubilizing agents (*acacia*, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Humectants (glycerin, hexylene glycol, propylene glycol, sorbitol); Polymers (e.g., cellulose acetate, alkyl celluloses, hydroxyalkylcelluloses, acrylic polymers and copolymers); Suspending and/or viscosity-increasing agents (*acacia*, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup). This list is not meant to be exclusive, but instead merely representative of the classes of excipients and the particular excipients which may be used in oral dosage unit dosage forms of the present invention.

Conventional additives may be included in the compositions of the invention, including any of those selected from preservatives, chelating agents, effervescing agents, natural or artificial sweeteners, flavoring agents, coloring agents, taste masking agents, acidulants, emulsifiers, thickening agents, suspending agents, dispersing or wetting agents, antioxidants, and the like. Flavoring agents can be added to the compositions of the invention to aid in compliance with a dosing regimen. Typical flavoring agents include, but are not limited to natural or synthetic essences, oils and/or extracts of pineapple, orange, lemon, mint, berry, chocolate, vanilla and melon.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Experimental Procedures

Expression Constructs and Expression cDNA encoding prh TNFR2:Fc was optimized and synthesized by GENEART AG (Regensburg, Germany). The codon usage was adapted to the codon bias of Nicotiana tabacum genes. The IgG1 portion was cloned from Fc IgG1 heavy chain constant region [Homo sapiens] ACCESSION AEV43323.

During the optimization process the following cis-acting sequence motifs were avoided: Internal TATA-boxes, chi-sites and ribosomal entry sites, AT-rich or GC-rich sequence stretches, RNA instability elements ("Killer motifs"), Repeat sequences and RNA secondary structures, splice donor (cryptic) and acceptor sites, branch points. In addition, regions of very high (>80%) or very low (<30%) GC content were avoided. The resultant DNA sequence is as set forth in SEQ ID NO: 1. The encoded polypeptide is as set forth in SEQ ID NO: 2. To the native cDNA sequence, a signal peptide (e.g. endoplasmic reticulum target signal peptide) from N. plumbaginifolia Calreticulin protein was added to the N' terminus of the gene, allowing efficient targeting of prh TNFR2:Fc to the secretory pathway and is then cleaved from the polypeptide, by signal peptidase, once the protein has been translocated into the endoplasmic reticulum (SEQ ID NO: 3, SEQ ID NO: 4, representing the DNA and peptide sequences of the ER signal peptide, respectively). Additionally, an ER retention signal SEKDEL was added to the C' terminus of the gene. This signal allows protein retrieval from the Golgi apparatus to the ER, and localization in the ER. The entire coding sequence (signal peptide-prh TNFR2:Fc-SEKDEL) is as set forth in SEQ ID NO: 5 and the encoded polypeptide is as set forth in SEQ ID NO: 6. The resultant protein following cleavage is as set forth in SEQ ID NO: 7, 204 or 205 (prh TNFR2:Fc-SEKDEL).

Stable Expression in N. tabacum BY2 Cells

Agrobacterium mediated transformation is widely used to introduce foreign genes into a plant cell genome. Using this approach, a T-DNA molecule consisting of a foreign gene and its regulatory elements is randomly introduced into the plant genome. Since the site of integration, as well as the copy number of the gene insertions cannot be controlled, the transformation process results in a highly heterogeneous transgenic 'pool' composed of cells with various levels of transgene expression. The transgenic 'pool' is subsequently used for clone isolation. The transformation process, results in establishment of numerous single cell lines, each representing an individual transformation event, from which the clone with the highest expression level of the foreign gene is selected. For prh TNFR2:Fc, the transformation was conducted with a plasmid carrying the prh TNFR2:Fc cassette (FIG. 1 SEQ ID NOs: 7 and 8). As a result, the recombinant protein is targeted to the Endoplasmic reticulum (ER) of the cells. The transformations of the BY2 cells with the prh TNFR2:FC-ER expression vector were performed by the Agrobacterium tumefaciens mediated plant transformation procedure as follow: BY2 (Bright Yellow 2) suspension culture was co-cultivated, for 48 hours, with the Agrobacterium tumefactiens strain carrying the vector harboring the prhTNFR2:FC-gene and the neomycin phosphotransferase (NPTII) selection gene. Subsequently, cells were kept in media supplemented with 50 mg/L of Kanamaycin and 250 mg/L Cefotaxime. The NPTII gene confers resistance to Kanamycin, thus only NPTII positive BY2 cells survive in this selection media. The Cefotaxime was used to selectively kill the *agrobacterium*, the plant cells being resistant to this antibiotic.

Screening for the Optimal Expressing Clone

In order to select individual cell lines, aliquots of highly diluted cell suspension were spread on solid BY-2 medium (Toshiyuki Nagata & Fumi Kumagai *Methods in Cell Science* 21: 123-127, 1999). The cells were then grown until small calli developed. Each callus was then re-suspended in liquid culture. Cells were then sampled and evaluated for prh TNFR2:FC. About 500 cell lines were screened by Western blot under denaturing conditions (FIG. 4). The lines with high expression levels were further re-analyzed by the same method to select the highest expressing clone of prh TNFR2:FC producing clone.

Gel Electrophoresis:

Sodium Dodecyl Sulfate-Polyacrylamide Gel Electrophoresis (SDS-PAGE) separates proteins on an electrical field according to their size. Proteins in the presence of the detergent SDS migrate as a linear function of the logarithm of their molecular weight. Migration pattern and identification of prh TNFR2:FC on SDS-PAGE was compared to commercial molecular weight standard proteins (New England BioLabs; cat No. P7708S) and to the commercially available, mammalian-cell derived Enbrel expressed in CHO cells (Entanercept; Wyeth). prh TNFR2:FC was extracted from cells either by reducing sample buffer containing β-mercaptoethanol or by native extraction buffer. The native extraction supernatant was mixed with non-reducing sample buffer prior to analysis. Electrophoresis was performed using Criterion™ cell vertical electrophoresis apparatus (Bio-Rad Lab.) with premixed electrophoresis Tris-Glycine-SDS running buffer (Bio-Rad Laboratories). Following electrophoresis, the proteins were transferred from the Polyacrylamide gel to a protein binding nitrocellulose membrane (iBlot™). Membranes were blocked for 1 hr at RT with 5% milk buffer containing 0.1% Tween 20. For identification of the Fc portion of the molecule, Goat anti human IgG conjugated to HRP (cat #109-035-098, Jackson.) was used. For TNFR2 detection, a Rabbit Anti-TNFRII (ID: ab109853, Abcam) followed by Goat anti Rabbit HRP (cat #111-035-003, Jackson) were employed. Detection was carried out with ECL detection kit (Pierce). The immunoreactivity of prh TNFR2:FC was compared to that of commercial Enbrel (Entanercept; Wyeth). Bands were detected using the Molecular Imager Gel Doc XR System (Bio-Rad Laboratories).

Amino Acid Sequencing by Mass-Spectrometry prhTNFR2:FC is sent for sequencing analysis at the Smoler Proteomics Center at the Technion—Israel Institute of Technology (Haifa, Israel). The protein is extracted from the gel, reduced with 2.8 mM DTT (60° C. for 30 min), modified with 8.8 mM iodoacetamide in 100 mM ammonium bicarbonate (in the dark, room temperature for 30 min) and digested in 10% ACN and 10 mM ammonium bicarbonate with modified Trypsin (Promega) or with ChymoTrypsin overnight at 37° C. in a 1:50 enzyme-to-substrate ratio. 3% of the resulting peptides are resolved by reverse-phase chromatography on 0.075×200-mm fused silica capillaries (J&W) packed with Reprosil reversed phase material (Dr Maisch GmbH, Germany). The peptides are eluted with linear 60 minutes gradients of 5 to 45% and 15 minutes at 95% acetonitrile with 0.1% formic acid in water at flow rates of 0.25 µl/min. On line mass spectrometry is performed by an ion-trap mass spectrometer (Orbitrap, Thermo) in a positive mode using repetitively full MS scan followed by collision induces dissociation (CID) of the 7 most dominant ion selected from the first MS scan.

The mass spectrometry data is analyzed using the Sequest 3.31 software (J. Eng and J. Yates, University of Washington and Finnigan, San Jose) vs a specific sequence.

Glycosylation Analysis

The major difference between glycoproteins produced in Chinese Hamster Ovary (CHO) cell and plant cell systems is the glycosylation profile and glycan structure. Preliminary analysis has been performed to characterize the various N-linked glycan structures attached to the protein. These results are compared to results of the N-glycosylation profile found in commercial Enbrel. The presence of O-linked glycans, and glycan site analysis is determined.

Samples of prh TNFR2:FC and commercial Enbrel are reduced, alkylated and separated on SDS-PAGE. The protein bands at ~75 KDa (a total of about 200 µg protein) are taken for glycan analysis using Trypsin digestion followed by either PNGase A or PNGase F digestion (~80% and ~20% of the total protein, respectively) for prh TNFR2:FC and PNGase F digestion only for commercial Enbrel. Digestion with Trypsin, followed by PNGase A releases all the N-linked glycans and digestion with PNGase F releases all glycans except those containing alpha 1-3 core fucose (found in plants). The released glycans are extracted, cleaned and then labeled with the fluorescent reagent anthranilamide (2-aminobenzamide, 2AB) followed by removal of excess 2AB. The analytical method includes separation of the glycans on a Waters HPLC system with a normal phase amide-based column (Tosoh TSK Amide-80 column), coupled with a fluorescence detector (330 nm excitation, 420 nm emission). Sequencing of the labeled glycan pool is achieved by sequential digestion with various exoglycosidases followed by additional HPLC analysis. Using sequential digestion with various exoglycosidases provides additional information on the profile of the glycans structures and their relative amounts. The exoglycosidase digestions that are carried out for the glycans released from prh TNFR2:FC are with JBH (Jack bean beta-N-Acetylhexosaminidase) that removes beta 1-2, 3, 4 and 6 N-acetylglucosamine (GlcNAc), with JBM (Jack bean mannosidase) that removes mannose alpha 1-2, 6>3 mannose and with BKF (Bovine testis fucosidase) that removes alpha 1-6 and alpha 1-3 core fucose. The fluorescence labeling enables a semi-quantitative analysis of the distribution of the various glycan structures in the total digested glycan pool. The glycans are then separated according to unique glycan linkages and in order of increasing size using a gradient solvent flow consisting of ammonium formate and acetonitrile. Retention time of individual glycans is compared to the retention times of a standard mix of partially hydrolysed dextran fragments, giving a ladder of glucose units (GU). The glycans are assigned to peaks according to their GU values, based on standards and a comparison to an external data base (www(dot)glycobase(dot)nibrt(dot)ie:8080/database/show_glycobase(dot)action). The final assignment and relative peak areas are calculated from the chromatogram of the PNGase A digestion.

Enzyme-Linked Immunosorbent Assay (ELISA)

Binding ELISA:

TNFα binding ELISA is a combination of a commercial TNFα detection ELISA kit (Human TNF-α; Hycult Biotech Inc.#HK307) and a commercial anti human IgG antibody (Goat anti human IgG FC specific HRP; Sigma). The assay is a quantitative non radioactive assay for prhTNFR2:FC binding activity. This binding ELISA enables to detect functional (capable of binding TNFα) molecules comprising both the TNFR and IgG domains.

An ELISA plate pre-coated with antibodies against TNFα was incubated with TNFα (60 ng/ml, Sigma) for 1 hour at room temperature. Between each ELISA step the plate was washed three times with commercial wash buffer. Commercial Enbrel and supernatant from BY2 cells expressing prh TNFR2:FC (serial dilutions) were incubated on ELISA plate for 2 hr at RT. Goat anti human IgG Fc HRP was diluted 1:10,000 and incubated on plate for 1 hr at RT. TMB was used as substrate for HRP. The colorimetric reaction was stopped with 10% HCL and absorbance determined at 450 nm.

Prevention of TNF α Induced Apoptosis in A375 Cells

A375 cells (human melanoma cells) were grown in suspension in culture medium (ATCC, #30-2002, supplemented with 10% FBS). $10^4$/well cells were plated in 96-well assay plates and incubated overnight in assay medium (ATCC, #30-2002, supplemented with 5% FBS). Recombinant TNFα (2 ng/ml, ProSpec, Rehovot, Israel) was incubated for 2 hr at 37° C. in the presence of different concentrations (1.562-100 ng/ml) of prhTNFR2:FC or commercial Enbrel (Entanercept; Wyeth). Following incubation, the mixed solution was added to A375 cells in the presence of actinomycin-D (0.8 µg/ml), incubated for further 24 hr at 37° C., 5% $CO_2$ in a humidified incubator and quantification of apoptosis was determined by MTT assay (Sigma Cat. No. M5655). The plate was read at 570-650 nm and the inhibition of TNF-α induced cytotoxicity (%) was calculated.

Example 2

Protein Analysis prhTNFR2:FC was analyzed under reducing (FIG. 2A) and non-reducing conditions (native extraction in the FIG. 2B). prhTNFR2:FC (Lane 1) and commercial Enbrel (lane 2) were detected using anti Fc antibody (upper panel) and anti TNFR2 antibody (lower panel). The two proteins demonstrate a slight difference in migration characteristics, presumably due to differences in glycosylation patterns between the plant and mammalian cell-expressed enzymes.

TNFα binding by both commercial Enbrel and prh TNFR2:FC was examined by comparing serial dilutions of lysates of BY2 cells expressing prh TNFR2:Fc (PRX-106) to commercial Enbrel. prh TNFR2:FC serial dilutions demonstrate a dose response binding pattern similar to the commercial protein (see FIG. 3). The selection of transgenic cell lines according to protein expression was done by Western blotting. Thus, to allow for the selection of individual cell lines, aliquots of highly diluted cell suspension were spread on solid BY-2 medium. The cells were then grown until small calli developed. Each callus was then re-suspended in liquid culture. Cells were then sampled and evaluated for prh TNFR2:Fc expression levels by extraction under reducing conditions followed by Western Blot identification (anti FC antibody) of the produced target protein (FIG. 4). The functionality of the expressed protein was established by its ability to prevent TNFα induced apoptosis. Specifically, TNFα activity can be measured by its ability to induce cell death of certain cell lines in the presence of the transcriptional inhibitor, actinomycin D. Pre-incubation with a neutralizing protein of TNFα prevents binding to the receptors (TNF-R1 and TNF-R2), thereby inhibiting the cytokine effect and preventing TNFα induced cell death. Quantification of cell viability by MTT assay provides an in-cell activity assay for TNFα cytotoxicity. The results are shown in FIGS. 5A-G on melanoma cells A375 and in FIGS. 6A-G on L929 fibroblasts.

Example 3

Prh TNFR2:FC Suppresses Inflammatory Bowel Disease (IBD)

Inflammatory bowel disease (IBD) is a chronic intestinal inflammatory condition that is medicated by genetic, immune, and environmental factors. About 0.2-0.3% of the population are diagnosed with IBD annually. IBD is characterized by a tendency for chronic or relapsing immune activation and inflammation within the Gastro-intestinal Tract (GIT). It has two presentations: Crohn's disease (CD), a chronic inflammation potentially involving any location of the GIT from mouth to anus, and Ulcerative colitis (UC), an inflammatory disorder that affects the rectum and extends proximally to affect variable extent of the colon. CD is regulated more by the TH1 immune cell response, overproducing the cytokines IL-12, IFN-gamma and TNFα lpha among others. UC, on the other hand, is mainly regulated by the TH2 immune cell response.

PRX106 is a soluble receptor for a cytokine overproduced in inflammation involving among others, the TH1 immune cell response. PRX106 was shown to be very effective when injected IV in other models of inflammation (Rheumatoid Arthritis). PRX106 is overexpressed in Protalix's ProCellEx™ system, in BY2 plant cells. Being a plant cell, BY2 has a cell wall that can help protect PRX106 while moving through the stomach and small intestine. In the colon, where the polysaccharides are digested, the plant cell releases its content and hence PRX106 is free to bind its cytokine ligand. Moreover, PRX106 is a chimeric protein carrying an Fc segment of human IgG1. In the epithelial monolayer lining the mucosal barrier, the FcRn receptor transcytoses IgG molecules across by binding to their Fc. Therefore, PRX106 can also cross the epithelial barrier to bind its cytokine ligand on the serosal side of the epithelia.

IBD models are classified into five major groups: chemically induced model, cell-transfer model, spontaneous model, congenital (spontaneous gene mutation) model, and genetically engineered model. In the most widely used chemically induced models, colitis is induced by intrarectal administration of the covalently reactive reagents TNBS/oxazolone, which are believed to induce a T-cell-mediated response against hapten-modified autologous proteins/luminal antigens. In the DSS model, mice are subjected several days to drinking water supplemented with DSS (dextran sodium sulfate), which seems to be directly toxic to colonic epithelial cells of the basal crypts. The disease severity is evaluated by scoring 3 major clinical signs (weight loss, diarrhea, and rectal bleeding). The mouse models TNBS (Example 3A) and DSS (Example 3B) are used to determine the therapeutic efficacy of the plant cells expressing the chimeric polypeptide in vivo.

Example 3A

PRX106-Expressing Cells are Effective in Alleviating Symptoms of IBD as Evidenced in an In Vivo Trinitrobenzene-Sulphonic Acid (TNBS) Model Materials and Methods
Ethics Statement—

All procedures were strictly performed in accordance with the Guide for the Care and Use of Laboratory Animals.

Animals

Male Balb/c mice, 8-9 weeks old were used in all experiments. Each experimental group included 5 to 10 mice. The mice were purchased from Harlan Laboratories, Israel. All mice were moved to SPF-free room (natural bacterial flora) several days before starting the experiment.

TNBS Induction

TNBS was induced in mice by rectal installation of TNBS [M. F. Neurath, I. Fuss et al: j exp. Med 182' 1281-1290 (1995)]. Mice were sensitized by painting 100 μL of 1% TNBS in ethanol onto the shaved skin of their abdomens 7 days before challenge. On the day of challenge, the mice were given 120 μL of 1% TNBS (Sigma Aldrich) slowly injected into the lumen of the colon via a catheter. Following TNBS treatment, mice were treated per os (PO) daily from day 0 to day 4 with BY-2 cells expressing PRX-106, equivalent to 5 μg protein (Dose I) and 30 μg protein (Dose II); BY-2(–) control cells in the same orally administered volumes of the PRX-106 expressing cells; and saline. TNBS control mice received PBS alone. The animals were monitored once daily for weight. Weight loss was calculated by subtracting the weight on each day from the weight on day 0. After the experiment, the animals were sacrificed and dissected. On day 5, blood samples were collected by cardiac puncture, and were left to clot and then centrifuged to obtain serum for determination of serum cytokine levels. (Cury et al. Cell Immunol. 2013, 282 (1); 66-70. Experiments were performed on 5-15 mice per group in three separate experiments; results followed the same pattern in all experiments.

Oral Administration of Recombinant Plant Cells

Oral administration of plant cells expressing recombinant TNFR2:Fc was initiated 6 hours after administration of TNBS. Mice received plant cells expressing recombinant TNFR2:Fc, resuspended in 350-500 μL. Negative controls received the same orally administered volumes of host Mock plant cells, instead of the plant cells expressing recombinant TNFR2:Fc. Oral administration was performed by gavage. Two more controls were untreated mice and TNBS treated mice that received saline.

Analysis of Cytokine Profiles

Serum levels of cytokines TNF-α, and IL-10 were determined using ELISA kits following the manufacturer's instructions (R&D Systems, Minneapolis, Minn., USA).

Antibody Array

Serum qualitative measurement of cytokine content was performed using the Mouse Cytokine Antibody Array (R&D Systems, Minneapolis, Minn., USA), according to the manufacturer's manual.

Immunohistochemistry

Paraffin-embedded colonic tissue sections (5 μm) were deparaffinized, rehydrated, washed and incubated in 3% $H_2O_2$ and blocked (Bar Sela et al 2006). Slides were incubated with In-alpha pSer32/Ser36 antibodies (Abcam) Color was developed using the DAB substrate kit (Thermo Scientific) or Zymed AEC substrate kit (Zymed Laboratories), followed by counterstaining with Mayer's hematoxylin. Controls without addition of primary antibody showed low or no background staining in all cases. Blocking was performed according to Bar-Sela et al. Histopathology. 2006; 49:188-193.

Flow Cytometry

Spleens were harvested from mice in RPMI 1640 medium. Cell suspensions were prepared by dicing spleens with a razor blade, followed by passage through a 40 μM Nylon filter (BD Falcon). Splenocytes were incubated with anti-mouse CD4 (R&D Systems, Minneapolis, Minn., USA) and anti-mouse CD25 (R&D Systems, Minneapolis, Minn., USA). Cells were then fixed and permeabilized for 20 min at 4° C. and then incubated with anti-mouse Foxp3 (Mouse Regulatory T cell 3-Color Flow kit, R&D Systems, Minneapolis, Minn., USA) diluted in permeabilization buffer for 30 min. Ten thousand CD4$^+$ cells were analyzed by FACS.

Macroscopic Colon Damage

Macroscopic appearance of the colon was assessed using the Wallace macroscopic scoring system [W. Vermeulen, J. G. de Man, S. Nullens, P. A. Pelckmans, B. Y. de Winter, and T. G. Moreels, "The use of colonoscopy to follow the inflammatory time course of TNBS colitis in rats," Acta Gastro-Enterologica Belgica, vol. 74, no. 2, pp. 304-311, 2011]. In this scoring system, the inflammation is assessed on the following scale from 0 to 10 based on ulceration, inflammation, and extent of disease: 0=normal aspect of the mucosa, 1=localized hyperemia without ulcerations, 2=ulceration, 3=ulceration with thickening of bowel wall at one site, 4=two or more sites of ulceration and thickening of the bowel wall, 5=major sites of damage extending <2 cm along the length of the colon, and 6-10=damage extending >2 cm (with the score increasing by 1 for each centimeter of damaged tissue).

Results

Oral administration of plant cells expressing recombinant TNFR2:Fc improved TNBS-Induced body weight loss as monitored 4 days after initiation of TNBS administration (FIGS. 7A-B).

Colon lengths were measured as morphological indicators of colon inflammation in TNBS-treated mice; short colon indicating an inflammatory state. As shown in FIG. 8, the colon length of mice treated with TNBS was significantly shortened compared to the control mice. The length of colon of the treated group (oral administration of cells expressing prTNFR2:Fc) was significantly longer than that in the TNBS-treated group.

Oral administration of plant cells expressing recombinant TNFR2:Fc also improved the macroscopic features of TNBS-induced colitis. Macroscopic examination of colons, showed reduced colon damage severity compared with the non treated colons (FIG. 9).

Oral administration of plant cells expressing recombinant TNFR2:Fc reduced the expression of proinflammatory cytokines in mice with TNBS-induced colitis (FIGS. 10A-C). The effect of the treatment on the serum levels of proinflammatory cytokines linked to TNBS colitis and anti-inflammatory cytokines was evaluated. Note that in most of the TNFR2:Fc treated groups the expression levels of proinflammatory cytokines IL-6 and TNF-α were reduced, and the expression levels of anti-inflammatory cytokine IL-10 were elevated.

FIGS. 11A-B showed that treatment with oral administration of plant cells expressing recombinant TNFR2:Fc reduced level of inflammatory mediators like granulocyte colony-stimulating factor G-CSF, macrophage colony-stimulating factor (M-CSF), potentially indicating reduced systemic inflammation by lowering systemic recruitment of bone marrow derived cells from the bloodstream.

Recently, imbalance of the development and function of IL-17-producing Th17 cells and CD4$^+$CD25$^+$FOXP3$^+$ Treg cells has been demonstrated to play an important role in autoimmune diseases, including IBD. Treg cells, also known as CD4$^+$CD25$^+$, FOXP3$^+$, are involved in the maintenance of peripheral tolerance and in controlling the immune response by initiating suppressive effects on activated immune cells. The present analysis shows that oral administration of plant cells expressing TNFR2:Fc expands population of functional regulatory T (T reg) cells in the spleen (FIG. 12).

To conclude the above-results demonstrate that oral administration of plant cells expressing recombinant TNFR2:Fc is an anti-inflammatory agent that ameliorates TNBS-induced colitis.

Example 3B

PRX106-Expressing Cells are Effective in Alleviating Symptoms of IBD as Evidenced in an In Vivo Dextran Sulfate Sodium-Induced (DSS-Induced) Model The Dextran Sulfate Sodium-induced (DSS-induced) mouse model of IBD is used for compounds for efficacy in Inflammatory Bowel Disease. This is an experimental acute Ulcerative Colitis model with symptoms similar to those observed in human UC, such as diarrhea, bloody feces, body weight loss, mucosal ulceration and shortening of the large intestine.

Ethics Statement

All procedures were strictly performed in accordance with the Guide for the Care and Use of Laboratory Animals.

Animals

Male C67/B1 mice, 8-9 weeks old were used in all experiments. Each experimental group included 10 mice. The mice were purchased from Harlan Laboratories, Israel. All mice were moved to SPF-free room (natural bacterial flora) several days before starting the experiment.

Induction and Evaluation of Colitis in Mice Treated with DSS and Following Oral Administration of Plant Cells Expressing Recombinant TNFR2:Fc Colitis was induced by administration of 1.5% (wt/vol) DSS (reagent-grade DSS salt; molecular mass=36-50 kD; MP Biomedicals) in normal drinking water for 5 days, followed by 5 days of normal water consumption. Daily treatment with orally administered plant cells expressing recombinant TNFR2:Fc; Mock cells comprising vector alone or control treatment (saline) began 24 hours following DSS induction, for a period of 7 days. Colonic inflammation was assessed 5 days after DSS treatment by punch biopsies and histological score. The animals were monitored once daily for weight, weight loss was calculated by subtracting the daily weight from the weight on day 0. After the experiment, the animals were sacrificed and dissected; colon shortening was assessed by colon length measurements in comparison to untreated colon; Blood samples were collected by cardiac puncture, and were left to clot and then centrifuged to obtain serum for determination of serum cytokine levels.

Oral Administration of Recombinant Plant Cells:

Oral administration of plant cells expressing recombinant TNFR2:Fc was initiated 24 hours following DSS administration. Mice received plant cells expressing recombinant TNFR2:Fc (comprising 30 µg of protein), suspended in 500 µl saline. Negative controls received the equivalent volumes of host Mock plant cells, to the plant cells expressing recombinant TNFR:Fc. Two more control groups were DSS treated mice administered with saline and untreated mice. Oral administration was performed by gavage.

Analysis of Colon Inflammation.

Paraffin-embedded colon tissue sections were stained with hematoxylin and eosin for light microscopic examination to assess colon injury and inflammation. Samples from entire colon were analyzed pathologically by a pathologist blinded to treatment conditions. A scoring system including degree of inflammation, crypt damage, percentage of area involved by inflammation and depth of inflammation was used.

Punch Biopsies.

Mouse colons were flushed 3 times with PBS containing antibiotics and opened along a longitudinal axis. Thereafter, 4-mm$^2$ punch biopsies were obtained and incubated for 24 hours in RPMI-1640 medium supplemented with antibiotics. Supernatants were collected and kept in –20° C. until assessed for cytokine expression. Qualitative measurement of cytokine content in medium conditioned by colonic explants was performed using the Magnetic Luminex Screening Assay according to the manufacturer's manual R&D Systems, Minneapolis, Minn., USA).

Analysis of Cytokine Profiles

Serum levels of cytokines TNF-α, IL-6 and IL-10 were determined using Magnetic Luminex Screening Assay following the manufacturer's instructions (R&D Systems, Minneapolis, Minn., USA).

Results

1. Oral Administration of Plant Cells Expressing Recombinant TNFR2:Fc Improved DSS-Induced Body Weight Loss Body weight was monitored each day following DSS administration (FIGS. 13A-B). As can be seen, treatment of mice orally with plant cells expressing recombinant TNFR2:Fc attenuated the weight loss induced by DSS.

2. Oral Administration of Plant Cells Expressing Recombinant TNFR2:Fc Suppressed DSS-Induced Colitis in Mice Colon lengths were measured as it is well established that a short colon can be used as a morphological indicator of colon inflammation in DSS-treated mice. As shown in FIGS. 14A-B, the colon length of mice treated with DSS was significantly shortened compared with the control mice. The length of colon in the oral administration of plant cells expressing recombinant TNFR2:Fc group was significantly longer than that in the DSS-treated group.

3. Effect of Oral Administration of Plant Cells Expressing Recombinant TNFR2:Fc on Gut Inflammatory Cytokines Following DSS Colitis FIGS. 15A-C show a statistically significant decrease in gut proinflammatory cytokines following oral treatment with plant cells expressing recombinant TNFR2:Fc.

4. Oral Administration of Plant Cells Expressing Recombinant TNFR2:Fc Reduced the Expression of Proinflammatory Cytokines in Mice with DSS-Induced Colitis The effect of Oral administration of plant cells expressing recombinant TNFR2:Fc on the production of proinflammatory cytokines linked to DSS colitis was evaluated. As shown in FIGS. 16A-C, DSS induced protein expression of proinflammatory cytokines, such as IL-6 and TNF-α, in sera, whereas Oral administration of plant cells expressing recombinant TNFR2:Fc suppressed the host protein secretion of proinflammatory cytokines. These results pointed out that oral administration of plant cells expressing recombinant TNFR2:Fc inhibited the production of proinflammatory cytokine in the DSS-induced colitis model.

5. Histopathological Examination as an Indication for Colon Inflammation

The severity of colon inflammation was further evaluated by histological examinations (FIGS. 17A-B). Following DSS administration, colons exhibited transmural inflammation and intense infiltration of inflammatory cells. This cell influx associated with ulceration, loss of goblet cells and marked disruption in the crypts throughout the colon. On note, oral treatment with plant cells expressing TNFR2:Fc markedly improved the hisological features of DSS-induced colitis. Histological examination of colons, showed reduced colon damage severity in colons of orally administered plant cells expressing recombinant TNFR2:Fc treated mice, compared with the DSS and Mock treated colons.

In conclusion, the present study supports a role for orally administered plant cells expressing recombinant TNFR2:Fc as an anti-inflammatory agent with the capacity to ameliorate IBD.

Example 4

Evaluating the Recombinant TNFR2:Fc Protein Pharmacokinetic Profile in Rat Plasma at Various Time Points Post Feeding of Plant Cells Expressing Recombinant TNFR2:Fc Materials and Methods Animals Rats (SD, females/9-10 weeks/n=6) were subject to a 20 hours fast and then fed (free feeding) with cells expressing recombinant TNFR2:Fc (PRX-106) and host BY2(−). Following two hours from feeding, food consumption was measured. Young suckling rats (SD, males and females/16 days/n=6) were 3 hours fasted and fed (by gavage) with cells expressing recombinant TNFR2: Fc (PRX-106) and host BY2(−) cells.

Analysis of TNFR2 Profiles

Blood samples were collected in the each time point (e.g., 0, 1 h, 2 h, 4 h, 6 h, 8 h, and 24 h), left to clot and then centrifuged to obtain serum. Serum levels of human TNFRII were determined using ELISA kits following the manufacturer's instructions (R&D Systems, Minneapolis, Minn., USA).

Results

TNFR2:Fc level in serum is shown in FIG. 18. Results demonstrate the elevation of TNFR2:Fc level in plasma following oral administration of plant cells expressing the protein. TNFR2:Fc level in serum was detected at 8 h, and was still detectable at 24 hours. TNFR2:Fc level in rat's serum fed with host BY2(−) was not detectable.

The experiment was then followed by analysis of recombinant TNFR2:Fc protein pharmacokinetic profile in the suckling rat plasma various time points post feeding of plant cells expressing TNFR2:Fc. TNFR2:Fc level in serum is shown in FIG. 19. Results demonstrate the significant elevation of TNFR2:Fc level in plasma following oral administration of TNFR2:Fc. TNFR2:Fc level in plasma peaked at 4 h. Probably, increased level of TNFR2:Fc in serum of suckling rats relative to adult rat was due to expression of FcNR in intestine of suckling rats. TNFR2:Fc level in rat's serum fed with host BY2(−) was not detectable.

Example 5

Toxicology Studies in Mice

Methods

Animals

Male and female SD Rats (Harlan Laboratories, Israel) 8 weeks at study initiation were housed under standard laboratory conditions. Mean weight at study initiation was approximately 6.8 gr for males and 6.3 gr for females. Animals were fed with commercial rodent diet (Teklad Certified Global 18% Protein Diet cat #: 2018SC) and had free access to autoclaved and acidified drinking water (pH between 2.5 and 3.5).

Study Design

Four groups, 3 dosing groups comprising 12 rats per group (6 males and 6 females) and a control group comprising 6 rats per group (3 males and 3 females), were assigned. In each gender, the control group received dilution buffer (0.2 M mannitol) and three treated groups received cells expressing TNFR2:Fc at dose levels of 0.1, 0.5 and 1 mg TNFR2:Fc/Kg body weight. Cells were aliquoted in accordance with requested expressed protein amount. Each aliquot was mixed with 30 grams powder of commercial rodent diet and dilution buffer, to create a pellet. The control pellet was made with dilution buffer and commercial rodent diet powder alone. All animals were daily orally fed with the pellets for 14 days. During the study, mortality and general clinical observation were performed, bodyweight was monitored daily. At study termination (Day 15) after light anesthesia with carbon dioxide inhalation, three blood samples were drawn from all animals from the retro orbital sinus gross, after which, animals were sacrificed, pathology was executed and selected organs were harvested.

Results

No adverse clinical symptoms were recorded throughout the 14-day safety study. All blood parameters were within the normal range with no significant deviations. Body weight gain was persistent and normal with no significant difference between the groups (treated or Control). Cells expressing were found to be safe and well tolerated with no adverse effects. No effect on biochemical parameters or clinical symptoms was found. Gross necropsy observation did not reveal pathological findings. No animal was found in a moribund state or under severe distress conditions. There were no observations of animals presenting severe pain or decreased body weight.

Example 6

Sequencing of PRX-106

N Terminus Sequencing by Edman Degradation

Analysis was performed at Alphalyse (Denmark) uainf, an ABI Procise 494 sequencer. The procedure determines the N-terminal amino acid sequence of proteins and peptides by the Edman degradation chemistry. The Edman degradation is a cyclic procedure where amino acid residues are cleaved off one at a time and identified by chromatography. Here are 3 steps in the cyclic procedure. In step 1, the PITC reagent is coupled to the N-terminal amino group under alkaline conditions. In step 2, the N-terminal residue is cleaved in acidic media. In step 3, the PITC coupled residue is transferred to a flask, converted to a PTH-residue and identified by HPLC chromatography. The next cycle is then started for identification of the next N-terminal residue.

Results:

The sequence was determined to be LPAQV (SEQ ID NO: 18).

Amino Acid Sequence Verification by Reverse Phase HPLC Coupled to a Mass Spectrometry Detector.

Sequencing was performed at the Smoler Proteomics Center (Technion-Israel Institute of Technology, Haifa, Israel). Analyses were carried out using reverse-phase HPLC coupled to a mass spectrometry detector.

Method

Proteolysis

The analyzed samples were resuspended in 8 M Urea, 100 mM ammonium bicabonate (ABC) followed by reduction with 2.8 mM DTT (60° C. for 30 min) and modified with 8.8 mM iodoacetamide in 100 mM ABC in the dark, at ambient temperature for an additional 30 min. The proteins were digested overnight at 37° C. using modified trypsin (Promega) at a 1:50 enzyme-to-substrate ratio in 2 M Urea, 25 mM ABC.

Mass Spectrometry Analysis

The tryptic or chymotryptic peptides were desalted using stage tips (home-made C18), the residual buffer was evaporated and the pellet was resuspended in 0.1% (v/v) formic acid. Twenty nanogram of the resulting peptides were resolved by reversed-phase liquid chromatography on a 0.075×200-mm fused silica capillaries (J and W) packed with Reprosil reversed phase material (Dr Maisch GmbH, Germany). Peptides were eluted with a linear 60 minutes gradient of 5 to 45% followed by 15 minutes at 95% acetonitrile with 0.1% formic acid in water at flow rates of 0.25 μL/min. On-line mass spectrometry was performed on an ion-trap mass spectrometer (Orbitrap, Thermo) in a positive mode using repetitively full MS scan followed by collision induced dissociation (CID) of the 7 most dominant ions selected from the first MS scan. The mass spectrometry data was analyzed using the Discoverer software version 1.3 software using a specific protein derived database.

Results

The sequence was compared to the peptide sequence of the Etanercept sequence. The identified sequences are presented in Table V, below. Presented is 84.8% coverage of the reference sequence (see green color, FIG. 20).

TABLE V

Peptides Identified Following Digestion with Trypsin (SEQ ID NO: 19-203, ordered)

WQQGnVFScSVMHEALHnHYTQK

WQQGNVFScSVMHEALHNHYTqK

GFYPSDIAVEWESNGqPENnYKT qYNSTYRVVSVLTVLHqDWLNGK

WQqGNVFScSVMHEALHNHYTqKS

VVSVLTVLHQDWLNGKEYKc

VVSVLTVLHqDWLnGKEYK

SqHTqPTPEPSTAPSTSFLLPmGPSPPAEGSTGDEPK

WQQGnVFScSVMHEALHNHY

ScDKTHTcPPcPAPELLGGPSVFLFPPKPKD

GQPREPqVYTLPPSREEMTK

GFYPSDIAVEWESNGQPEnNYKT

LPAqVAFTPYAPEPGSTcR

EALHnHYTqK qNRIcTcRPGWYcALSKQEGcR

WQQGNVFScSVmHEALHnHYTQK

SqHTQPTPEPSTAPSTSFLLPMGPSPPAEGSTGDEPK

GQPREPqVYTLPPSREEmTK

GFYPSDIAVEWESnGQPENNYK

TABLE V-continued

Peptides Identified Following Digestion with Trypsin (SEQ ID NO: 19-203, ordered)

SqHTQPTPEPSTAPSTSFLLPmGPSPPAEGSTGDEPK

VVSVLTVLHQDWLnGK

TYTqLWNWVPEcLScGSRcSSDqVETQAcTR

WQQGNVFScSVMHEALHNHYTQK

GFYPSDIAVEWESnGQPEnnYKT

VVVDVSHEDPEVK

PSTSFLLPMGPSPPAEGSTGDEPK

LPAQVAFTPYAPEPGSTcR

TTPPVLDSDGSFFL

LSLSPGK

EPQVYTLPPSREEMTKN

SmAPGAVHLPQ

TTPPVLDSDGSFFLYSK

WQQGNVFScSVmHEALHNHYTQK

SMAPGAVH

SVmHEALHNHYTQK

VVSVLTVLH

SQHTQPTPEPSTAPSTSFLLPMGPSPPAEGSTGDEPK

GQPREPQVY

AQVAFTPYAPEPGSTcR cAPLRK

EPQVYTLPPSREEmTKnQVSLTcLVK

SmAPGAVH

VVSVLTVLHQD

LFPPKPK

GSFFLYSK

IcTcRPGWY

SQHTQPTPEPS

SVLTVLHQDWLnGKEYK

QVETQAcTR

SLSLSPGK

SDGSFFLYSK

KALPAPIEK

ALPAPIEK

AVcTSTSPTR

SQHTQPTPEPSTAPSTSF

QVSLTcLVK

LREYYDQTAqmccSKcSPGQHAK

TABLE V-continued

Peptides Identified Following Digestion with Trypsin (SEQ ID NO: 19-203, ordered)

WQQGNVFScSVMHEALH

DTLmISR

PmGPSPPAEGSTGDEPK

THTcPPcPAPELLGGPSVF

DTLMISR

SDQVETQAcTR

KcRPGFGVAR

WYVDGVEVHNAK

YVDGVEVHNAK

TTPPVLDSDGSFF

THTcPPcPAPELLGGPSVFLFPPKPK

PSPPAEGSTGDEPK

SLSLSPGKSEKD

MAPGAVHLPQPVSTR

VDGVEVHNAK

ScDKTHTcPPcPAPELLGGPSVF

VVSVLTVLHQDWLNGK

SLSLSPGKSEK

PPcPAPELLGGPSVFLFPPKPK

SFFLYSK

FNWYVDGVEVHNAK

FLLPMGPSPPAEGSTGDEPK

DAVcTSTSPTR

NQVSLTcLVK

NqVSLTcLVKG

SLSPGKSEK

TPEVTcVVVDVSHEDPEVK

LREYYDQTAQM

GFYPSDIAVEWESNGQPENNYK

FNWYVDGVEVHN

VVSVLTVLHQDWLN

SQHTQPTPEPSTAPST

RTPEVTcVVVDVSHEDPEVK

SLSLSPGKS

LSPGKSEKDEL

LPQPVSTR

TTPPVLDSDGSFFLY

TSDTVcDScEDSTYTQLWN

ALPAQVAFTPYAPEPGSTcR

EEQYNSTYR

ScDKTHTcPPcPAPELLGGPSVFLFPPKPK cSPGQHAKVFcTK

TPEVTcVVVDVSHED

SMAPGAVHLPQPV

TcRPGWYcALSK

TcPPcPAPELLGGPSVFLFPPKPK

TSDTVcDScEDSTYTQLWNWVPEcLScGSR

LcAPLRK

SPPAEGSTGDEPK

WVPEcLScGSR

GPSPPAEGSTGDEPK

SSDQVETQAcTR

EEQYnSTYR

VAFTPYAPEPGSTcR

PGWYcALSK cRPGFGVAR

ScSVmHEALHnHYTqK

VVSVLTVLHQDWLNGKEYK

LcAPLR

EPQVYTLPPSREEMTKnQVSLTcLVK

LLPMGPSPPAEGSTGDEPK

SQHTQPTPEPSTAPSTSFLLPmGPSPPAEGSTGDEPK

SLSLSPGKSE

EEMTKNqV

SVMHEALHNHYTQK

SQHTQPTPEPSTAPSTSFLLPMGPSPPAEGSTGDEPKScDK

EEmTKnQVSLTcLVKG

LREYYDQTAQmccSK cSSDqVETQAcTR

EPQVYTLPPSREEMTK

NQVSLTcLVKG cSSDQVETQAcTR nQVSLTcLVK

TKPREEQYNSTYR

PAQVAFTPYAPEPGSTcR

SLSLSPGKSEKDEL

AFTPYAPEPGSTcR

TABLE V-continued

Peptides Identified Following Digestion with
Trypsin (SEQ ID NO: 19-203, ordered)

APGAVHLPQPVSTR
SDGSFFLYSKLTVDK
THTcPPcPAPELLG
VVSVLTVLHQDWLn
EPQVYTLPPSR
SmAPGAVHLPQPVSTR
GQPREPQVYTLPPSREEmTK
TPYAPEPGSTcR
EVTcVVVDVSHEDPEVK
TKPREEQYnSTYR
VSnKALPAPIEK
LREYYDQTAQMccSK
FTPYAPEPGSTcR
SMAPGAVHLPQPVSTR
GPSVFLFPPKPK
VVSVLTVLHQDWLnGKEYK
SQHTQPTPEPSTAPS
SMAPGAVHLPQPVS
AVHLPQPVSTR
GQPREPQVYTLPPSR
PGAVHLPQPVSTR
TLMISR
KNqVSLTcLVKGFYPSDIAVEWESNGqPENnYK
LREYYDQTAQMc
SmAPGAVHLPQPV
LPAPIEK
EYYDQTAQMccSK
NWVPEcLScGSR
SLSPGKSEKDEL
IcTcRPGWYcALSK
SMAPGAVHLPQPVST
EYYDQTAQmccSK
ASMDAVcTSTSPTR
SQHTQPTPEPSTAPSTS
TLPPSREEMTK
SQHTQPTPEPSTAPSTSFL
TLmISR
EPQVYTLPPSREEmTK
GQPREPQVYTLPPSREEMTK TABLE V-continued Peptides Identified Following Digestion with
Trypsin (SEQ ID NO: 19-203, ordered)

TPEVTcVVVDVSHEDPEVKFN
ScDKTHTcPPcPAPELLG
GFYPSDIAVEWESNGqPENnYK
AKGQPREPQVYTLPPSR
LREYYDQTAQMcc
LPmGPSPPAEGSTGDEPK
ScSVMHEALHNHYTQK
FNWYVDGVEVHnAK
PMGPSPPAEGSTGDEPK
SMAPGAVHLPqPVSTR
SMAPGAVHLPQ
LPMGPSPPAEGSTGDEPK

Example 7

Evaluation of Orally Administered PRX-106 Plant Cells Expressing Recombinant TNFR2:Fc in the Clinical Context In order to assess safety of administration of orally administered plant cells expressing recombinant TNFR2:Fc, also referred to herein as OPRX-106 and to evaluate pharmacokinetic parameters of the OPRX-106, OPRX-106 is administered to healthy subjects as further described herein below.

Primary Objective

The primary objective of this trial is to evaluate the safety of OPRX-106, in healthy male volunteers.

Secondary Objective

The secondary objective of this clinical study is to evaluate the pharmacokinetics of TNFR2-Fc following administration of OPRX-106 in healthy male volunteers.

Overall Study Design and Plan—Description

This is a Phase 1, randomized, open-label study to evaluate the safety of OPRX-106 and pharmacokinetics of TNFR-Fc following oral administration of OPRX-106 in healthy volunteers. Up to 18 healthy male subjects (age 18 years and older) are randomly allocated to one of three dose cohorts (up to 6 and not less than 4 subjects per cohort) receiving OPRX-106 doses equivalent to 2 mg, 8 mg or 16 mg TNFR-Fc. Subjects receive daily oral administrations of OPRX-106 for 5 consecutive days. Subjects remain at the clinical center for 12 hours after the first administration of OPRX-106 and then return to the site as needed for additional administrations and study procedures. The cells are provided as a cell suspension.

At screening and on Days 1 (0 and 24 hours), 5 and 10, vital signs are measured, a physical examination is effected and blood samples are retrieved for laboratory tests. Adverse events (AEs) and concomitant medications are evaluated at all study visits.

Blood samples for Plasma TNFR-Fc levels are drawn three times (in 2 hour intervals) at screening, on Days 1 and 4: pre-administration, 2, 4, 6, 8, 10, 12, ±15 minutes at each time point, and 24±2 hours post administration.

A control (placebo) group is not necessary, as all safety endpoints are assessed as change from baseline. Subjects are allocated to a dose cohort to limit bias but the study is open-label in order to identify any dose-dependent adverse effects of OPRX-106.

Selection of Study Population

Inclusion Criteria

To be eligible for the study, subjects must meet the inclusion criteria listed below:
1. Healthy male age 18 or older;
2. BMI 20-25 kg/m$^2$;
3. Male subjects or their partners must use an adequate method of contraception at all times during the study;
4. Negative laboratory tests for HIV, HBcAb and anti HCV at the screening visit;
5. Naïve to any previous recombinant protein therapy;
6. Provide written informed consent; and
7. Have the ability to understand the requirements of the study and to comply with the study protocol and dosing regimen.

Exclusion Criteria

To be eligible for the study, subjects must not meet any of the exclusion criteria listed below:
1. Clinical evidence of any active significant disease that could potentially compromise the ability of the Investigator to evaluate or interpret the effects of the study treatment on safety assessment, thus increasing the risk to the subject to unacceptable levels;
2. Presence of any acute or chronic diseases;
3. History of any allergies or protein-drug hypersensitivity;
4. Suspected Tuberculosis (previous, active or latent);
5. Exposure to long-term steroid treatment within the last 12 months prior to the study;
6. Subject had a major operation in last 6 months;
7. Subject has received immunosuppressive treatment;
8. Chronic use of any medication including vitamins;
9. Participation in another clinical trial during the previous 3 months (subject report);
10. Reported history of alcohol or drug abuse;
11. Subjects with short bowel (more than 1 m removed of small bowel);

Removal of Subjects from Therapy or Assessment

Reasons for permanent discontinuation include the following:

Clinically significant adverse events (AEs);

Serious protocol violation;

Sponsor elects to terminate the study;

Subject requires the use of prohibited treatment or medication;

Intolerance to treatment;

The subject experiences progressive or severe hypersensitivity—to be treated appropriately and withdrawn from the study;

The subject requests to discontinue treatment or withdraws consent;

The Investigator feels that it is not in the best interest of the subject to continue treatment and/or if the Investigator believes that the subject can no longer be compliant with the requirements of the study;

Replacement Policy

Withdrawn subjects may be replaced upon Medical Director decision.

Primary Endpoint

The safety of each of the three doses of OPRX-106 as assessed by AEs, physical examinations, vital signs, concomitant medications and laboratory test results.

Vital signs are measured at screening and on Days 1 (0 pre-dose and 24 hours), 5 and 10. Vital signs comprising systolic and diastolic arterial blood pressure, pulse and body temperature are assessed at all study visits. Systolic and diastolic blood pressure is measured after the subject has been in supine position for at least 1 minute. All recordings are performed using standard equipment. Clinically significant abnormal findings are reported as AEs.

Clinical Laboratory Tests—Blood samples for clinical laboratory safety tests are collected after 8 hours fasting, at screening and pre-dose administration on Days 1, 2, and 5, and on Day 10. Clinical laboratory tests include total protein, albumin, alanine transaminase (ALT), aspartate aminotransferase (AST), alkaline phosphatase (ALP), gamma-glutamyl transpeptidase (GGTP), Lactate dehydrogenase (LDH), cholesterol, uric acid, creatinine, blood urea nitrogen (BUN), sodium (Na), potassium (K), fasting glucose, total bilirubin, and complete blood cell count (CBC) with differential. Clinically significant abnormal findings are reported as AEs.

Secondary Endpoint

The PK profile of TNFR-Fc following administration of each of the three doses of OPRX-106 on the first (Day 1) and last (Day 4) of administration as assessed by $AUCo_{0-t}$, $C_{max}$, $t_{max}$ and additional PK parameters based on observed results.

PK Parameters

Blood samples for Plasma TNFR-Fc levels are drawn three times (in 2 hour intervals) at screening, on Day1 and 4: pre-administration, 2, 4, 6, 8, 10, 12, ±15 minutes at each time point, and 24±2 hours post administration.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating an inflammatory bowel disease in a subject in need thereof, the method comprising orally administering to the subject a therapeutically effective amount of plant cells comprising a nucleic acid construct having a nucleic acid sequence encoding a plant produced chimeric polypeptide comprising:
   (i) a first domain which comprises a TNFα binding domain of a TNF receptor, and
   (ii) a second domain which comprises an Fc domain of an immunoglobulin, wherein said first domain and said second domain are N-terminally to C-terminally respectively sequentially translationally fused and wherein the chimeric polypeptide specifically binds TNFα,
   wherein said therapeutically effective amount of said polypeptide in the plant cells comprises 0.02-0.27 mg/kg, thereby treating the TNFα-associated medical condition in the subject.

2. The method of claim 1, wherein said therapeutically effective amount comprises 0.02-0.12 mg polypeptide/kg.

3. The method of claim 1, wherein said therapeutically effective amount comprises 0.12-0.27 mg polypeptide/kg.

4. The method of claim 1, wherein said inflammatory bowel disease is ulcerative colitis.

5. The method of claim 1, wherein said inflammatory bowel disease is Crohn's disease.

6. The method of claim 1, wherein said chimeric polypeptide comprises an additional domain encoding an endoplasmic reticulum signal peptide translationally fused N-terminally to said first domain.

7. The method of claim 6, wherein said signal peptide is a plant signal peptide.

8. The method of claim 7, wherein said plant signal peptide is as set forth in SEQ ID NO: 4.

9. The method of claim 1, wherein said first domain is 200-250 amino acids long.

10. The method of claim 9, wherein said first domain comprises the amino acid sequence LCAP (SEQ ID NO: 11) and VFCT (SEQ ID NO: 12).

11. The method of claim 10, wherein said first domain further comprises the amino acid sequence LPAQVAFX-PYAPEPGSTC (SEQ ID NO: 13).

12. The method of claim 11, wherein said first domain is as set forth in SEQ ID NO: 2.

13. The method of claim 1, wherein said immunoglobulin is IgG$_1$.

14. The method of claim 1, wherein said second domain is as set forth in SEQ ID NO: 9.

15. The method of claim 1, wherein said chimeric polypeptide is as set forth in SEQ ID NO: 6.

16. The method of claim 1, wherein said chimeric polypeptide comprises a plant-specific glycan.

17. The method of claim 1, wherein said chimeric polypeptide comprises an additional domain encoding an endoplasmic reticulum retention signal peptide translationally fused C-terminally to said second domain.

18. The method of claim 1, wherein said plant cells are tobacco cells from a suspension culture.

19. The method of claim 18, wherein said tobacco plant cells from suspension culture are tobacco Bright Yellow (BY) 2 cells.

20. A method of treating an inflammatory bowel disease in a subject in need thereof, the method comprising orally administering to the subject a therapeutically effective amount of tobacco BY-2 cells from suspension culture recombinantly expressing a chimeric polypeptide comprising:

(i) a first domain which comprises SEQ ID NO: 2, and
(ii) a second domain which comprises SEQ ID NO: 9,
wherein said first domain and said second domain are N-terminally to C-terminally respectively sequentially translationally fused and wherein the chimeric polypeptide specifically binds TNFα,
wherein said therapeutically effective amount of said polypeptide in the plant cells comprises 0.02-0.27 mg/kg, thereby treating the TNFα-associated medical condition in the subject.

21. The method of claim 20, wherein said chimeric polypeptide is as set forth in SEQ ID NO: 6.

22. The method of claim 20, wherein said inflammatory bowel disease is ulcerative colitis.

23. The method of claim 20, wherein said inflammatory bowel disease is Crohn's disease.

24. The method of claim 1, wherein said chimeric polypeptide is as set forth in SEQ ID NO: 7.

* * * * *

SEQUENCE LISTING

<160> NUMBER OF SEQ ID NOS: 205

<210> SEQ ID NO 1
<211> LENGTH: 705
<212> TYPE: DNA

<213> ORGANISM: Artificial sequence
<220> FEATURE:
<223> OTHER INFORMATION: DNA encoding a TNFR2 derived sequence

<400> SEQUENCE: 1

```
cttccagctc aggttgcttt tactccatat gctccggagc caggatctac ttgtaggctt    60
agggaatact acgatcagac tgctcaaatg tgctgctcta agtgctctcc aggacagcac   120
gctaaggttt tctgcactaa gacttcgata actgtttgcg attcttgcga ggattctact   180
tacactcagc tttggaattg ggttccagag tgtctttctt gtggatctag gtgctcttct   240
gatcaggttg agactcaggc ttgtactagg gagcagaata ggatttgtac ttgcaggcca   300
ggatggtatt gtgctctttc taagcaagag ggatgtaggc tttgtgctcc acttagaaag   360
tgcaggcctg gttttggagt tgctagacca ggaactgaga cttctgacgt tgtttgcaag   420
ccatgtgctc caggaacttt ctctaatact acttcttcta ctgatatttg caggccacat   480
caaatttgca atgttgttgc tattccaggt aatgcttcta tggatgctgt ttgcacttct   540
acttctccaa ctaggtctat ggctccagga gctgttcatc ttccacaacc agtttctact   600
aggtcacaac atactcagcc aactccagaa ccatctactg ctccatctac ttcattcctt   660
ttgccaatgg gaccatctcc accagctgaa ggatctactg gagat                   705
```

<210> SEQ ID NO 2
<211> LENGTH: 235
<212> TYPE: PRT
<213> ORGANISM: Artificial sequence
<220> FEATURE:
<223> OTHER INFORMATION: Amino acid sequence encoding TNFR2 derived sequence

<400> SEQUENCE: 2

```
Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205
```

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235

<210> SEQ ID NO 3
<211> LENGTH: 81
<212> TYPE: DNA
<213> ORGANISM: Artificial sequence
<220> FEATURE:
<223> OTHER INFORMATION: N. plumbaginifolia Calreticulin protein derived
      signal peptide encoding sequence

<400> SEQUENCE: 3
atggctactc aaaggagggc taatccatct tctcttcatc ttattactgt tttctctctt    60
cttgttgctg ttgtttctgc a                                              81

<210> SEQ ID NO 4
<211> LENGTH: 27
<212> TYPE: PRT
<213> ORGANISM: Artificial sequence
<220> FEATURE:
<223> OTHER INFORMATION: Amino acid sequence encoding signal peptide
      from N. plumbaginifolia Calreticulin protein

<400> SEQUENCE: 4

Met Ala Thr Gln Arg Arg Ala Asn Pro Ser Ser Leu His Leu Ile Thr
1               5                   10                  15

Val Phe Ser Leu Leu Val Ala Val Val Ser Ala
            20                  25

<210> SEQ ID NO 5
<211> LENGTH: 1506
<212> TYPE: DNA
<213> ORGANISM: Artificial sequence
<220> FEATURE:
<223> OTHER INFORMATION: Nucleic acid sequence encoding prh TNFR2:Fc
      (PRX106)

<400> SEQUENCE: 5
atggctactc aaaggagggc taatccatct tctcttcatc ttattactgt tttctctctt    60
cttgttgctg ttgtttctgc acttccagct caggttgctt ttactccata tgctccggag   120
ccaggatcta cttgtaggct tagggaatac tacgatcaga ctgctcaaat gtgctgctct   180
aagtgctctc caggacagca cgctaaggtt ttctgcacta agacttcaga tactgtttgc   240
gattcttgcg aggattctac ttacactcag ctttggaatt gggttccaga gtgtctttct   300
tgtggatcta ggtgctcttc tgatcaggtt gagactcagg cttgtactag ggagcagaat   360
aggatttgta cttgcaggcc aggatggtat tgtgctcttt ctaagcaaga gggatgtagg   420
ctttgtgctc cacttagaaa gtgcaggcct ggttttggag ttgctagacc aggaactgag   480
acttctgacg ttgtttgcaa gccatgtgct ccaggaactt ctctaatac tacttcttct   540 actgatattt gcaggccaca tcaaatttgc aatgttgttg ctattccagg taatgcttct   600
atggatgctg tttgcacttc tacttctcca actaggtcta tggctccagg agctgttcat   660
cttccacaac cagtttctac taggtcacaa catactcagc caactccaga accatctact   720
gctccatcta cttcattcct tttgccaatg ggaccatctc caccagctga aggatctact   780
ggagatgagc caaagtcttg cgataagact catacttgtc caccatgtcc agctccagaa   840
cttcttggag gaccatctgt tttcctttc ccaccaaagc caaggatac tcttatgatt   900

```
tctaggactc cagaggttac ttgcgttgtt gttgatgttt cacatgaaga tccagaggtg      960
aagttcaatt ggtacgttga tggagttgag gttcataatg ctaagactaa gccaagggag     1020
gagcaataca attcaacata cagggttgtt tctgttctta ctgttcttca tcaagattgg     1080
cttaatggaa aggaatacaa gtgcaaggtt tctaataagg ctttgccagc accaattgaa     1140
aagactattt ctaaggctaa gggacaacca agagagccac aagtttacac tcttccacca     1200
tctagggagg agatgactaa gaatcaagtt ctctcttactt gccttgttaa gggattctac     1260
ccatctgata ttgctgttga gtgggagtct aacggacagc tgagaataa ttacaagact      1320 actccaccag ttcttgattc tgatggatct ttcttccttt actctaagtt gactgttgat     1380
aagtctaggt ggcaacaggg aaatgttttc tcttgctctg ttatgcatga ggctcttcat     1440
aatcattaca ctcagaaatc actttctctt tctccaggta agagtgagaa ggacgagctc     1500
tgatga                                                                1506
```

<210> SEQ ID NO 6
<211> LENGTH: 500
<212> TYPE: PRT
<213> ORGANISM: Artificial sequence
<220> FEATURE:
<223> OTHER INFORMATION: prh TNFR2:Fc (PRX106) polypeptide

<400> SEQUENCE: 6

```
Met Ala Thr Gln Arg Arg Ala Asn Pro Ser Ser Leu His Leu Ile Thr
 1               5                  10                  15

Val Phe Ser Leu Leu Val Ala Val Val Ser Ala Leu Pro Ala Gln Val
            20                  25                  30

Ala Phe Thr Pro Tyr Ala Pro Glu Pro Gly Ser Thr Cys Arg Leu Arg
        35                  40                  45

Glu Tyr Tyr Asp Gln Thr Ala Gln Met Cys Cys Ser Lys Cys Ser Pro
    50                  55                  60

Gly Gln His Ala Lys Val Phe Cys Thr Lys Thr Ser Asp Thr Val Cys
65                  70                  75                  80

Asp Ser Cys Glu Asp Ser Thr Tyr Thr Gln Leu Trp Asn Trp Val Pro
                85                  90                  95

Glu Cys Leu Ser Cys Gly Ser Arg Cys Ser Ser Asp Gln Val Glu Thr
            100                 105                 110

Gln Ala Cys Thr Arg Glu Gln Asn Arg Ile Cys Thr Cys Arg Pro Gly
        115                 120                 125

Trp Tyr Cys Ala Leu Ser Lys Gln Glu Gly Cys Arg Leu Cys Ala Pro
    130                 135                 140

Leu Arg Lys Cys Arg Pro Gly Phe Gly Val Ala Arg Pro Gly Thr Glu
145                 150                 155                 160

Thr Ser Asp Val Val Cys Lys Pro Cys Ala Pro Gly Thr Phe Ser Asn
                165                 170                 175

Thr Thr Ser Ser Thr Asp Ile Cys Arg Pro His Gln Ile Cys Asn Val
            180                 185                 190

Val Ala Ile Pro Gly Asn Ala Ser Met Asp Ala Val Cys Thr Ser Thr
        195                 200                 205

Ser Pro Thr Arg Ser Met Ala Pro Gly Ala Val His Leu Pro Gln Pro
    210                 215                 220

Val Ser Thr Arg Ser Gln His Thr Gln Pro Thr Pro Glu Pro Ser Thr
225                 230                 235                 240

Ala Pro Ser Thr Ser Phe Leu Leu Pro Met Gly Pro Ser Pro Pro Ala
```

```
                    245                 250                 255
Glu Gly Ser Thr Gly Asp Glu Pro Lys Ser Cys Asp Lys Thr His Thr
                260                 265                 270
Cys Pro Pro Cys Pro Ala Pro Glu Leu Leu Gly Gly Pro Ser Val Phe
            275                 280                 285
Leu Phe Pro Pro Lys Pro Lys Asp Thr Leu Met Ile Ser Arg Thr Pro
290                 295                 300
Glu Val Thr Cys Val Val Val Asp Val Ser His Glu Asp Pro Glu Val
305                 310                 315                 320
Lys Phe Asn Trp Tyr Val Asp Gly Val Glu Val His Asn Ala Lys Thr
                325                 330                 335
Lys Pro Arg Glu Glu Gln Tyr Asn Ser Thr Tyr Arg Val Val Ser Val
            340                 345                 350
Leu Thr Val Leu His Gln Asp Trp Leu Asn Gly Lys Glu Tyr Lys Cys
                355                 360                 365
Lys Val Ser Asn Lys Ala Leu Pro Ala Pro Ile Glu Lys Thr Ile Ser
370                 375                 380
Lys Ala Lys Gly Gln Pro Arg Glu Pro Gln Val Tyr Thr Leu Pro Pro
385                 390                 395                 400
Ser Arg Glu Glu Met Thr Lys Asn Gln Val Ser Leu Thr Cys Leu Val
                405                 410                 415
Lys Gly Phe Tyr Pro Ser Asp Ile Ala Val Glu Trp Glu Ser Asn Gly
            420                 425                 430
Gln Pro Glu Asn Asn Tyr Lys Thr Thr Pro Pro Val Leu Asp Ser Asp
                435                 440                 445
Gly Ser Phe Phe Leu Tyr Ser Lys Leu Thr Val Asp Lys Ser Arg Trp
450                 455                 460
Gln Gln Gly Asn Val Phe Ser Cys Ser Val Met His Glu Ala Leu His
465                 470                 475                 480
Asn His Tyr Thr Gln Lys Ser Leu Ser Leu Ser Pro Gly Lys Ser Glu
                485                 490                 495
Lys Asp Glu Leu
            500

<210> SEQ ID NO 7
<211> LENGTH: 473
<212> TYPE: PRT
<213> ORGANISM: Artificial sequence
<220> FEATURE:
<223> OTHER INFORMATION: prh TNFR2:Fc (PRX106) mature polypeptide

<400> SEQUENCE: 7

Leu Pro Ala Gln Val Ala Phe Thr Pro Tyr Ala Pro Glu Pro Gly Ser
1               5                   10                  15
Thr Cys Arg Leu Arg Glu Tyr Tyr Asp Gln Thr Ala Gln Met Cys Cys
                20                  25                  30
Ser Lys Cys Ser Pro Gly Gln His Ala Lys Val Phe Cys Thr Lys Thr
            35                  40                  45
Ser Asp Thr Val Cys Asp Ser Cys Glu Asp Ser Thr Tyr Thr Gln Leu
        50                  55                  60
Trp Asn Trp Val Pro Glu Cys Leu Ser Cys Gly Ser Arg Cys Ser Ser
65                  70                  75                  80
Asp Gln Val Glu Thr Gln Ala Cys Thr Arg Glu Gln Asn Arg Ile Cys
                85                  90                  95
Thr Cys Arg Pro Gly Trp Tyr Cys Ala Leu Ser Lys Gln Glu Gly Cys
```

```
                100             105              110
     Arg Leu Cys Ala Pro Leu Arg Lys Cys Arg Pro Gly Phe Gly Val Ala
             115                 120                 125

Arg Pro Gly Thr Glu Thr Ser Asp Val Val Cys Lys Pro Cys Ala Pro
         130                 135                 140

Gly Thr Phe Ser Asn Thr Thr Ser Ser Thr Asp Ile Cys Arg Pro His
     145                 150                 155                 160

Gln Ile Cys Asn Val Val Ala Ile Pro Gly Asn Ala Ser Met Asp Ala
                     165                 170                 175

Val Cys Thr Ser Thr Ser Pro Thr Arg Ser Met Ala Pro Gly Ala Val
                 180                 185                 190

His Leu Pro Gln Pro Val Ser Thr Arg Ser Gln His Thr Gln Pro Thr
             195                 200                 205

Pro Glu Pro Ser Thr Ala Pro Ser Thr Ser Phe Leu Leu Pro Met Gly
         210                 215                 220

Pro Ser Pro Pro Ala Glu Gly Ser Thr Gly Asp Glu Pro Lys Ser Cys
     225                 230                 235                 240

Asp Lys Thr His Thr Cys Pro Pro Cys Pro Ala Pro Glu Leu Leu Gly
                     245                 250                 255

Gly Pro Ser Val Phe Leu Phe Pro Pro Lys Pro Lys Asp Thr Leu Met
                 260                 265                 270

Ile Ser Arg Thr Pro Glu Val Thr Cys Val Val Val Asp Val Ser His
             275                 280                 285

Glu Asp Pro Glu Val Lys Phe Asn Trp Tyr Val Asp Gly Val Glu Val
         290                 295                 300

His Asn Ala Lys Thr Lys Pro Arg Glu Glu Gln Tyr Asn Ser Thr Tyr
     305                 310                 315                 320

Arg Val Val Ser Val Leu Thr Val Leu His Gln Asp Trp Leu Asn Gly
                     325                 330                 335

Lys Glu Tyr Lys Cys Lys Val Ser Asn Lys Ala Leu Pro Ala Pro Ile
                 340                 345                 350

Glu Lys Thr Ile Ser Lys Ala Lys Gly Gln Pro Arg Glu Pro Gln Val
             355                 360                 365

Tyr Thr Leu Pro Pro Ser Arg Glu Glu Met Thr Lys Asn Gln Val Ser
         370                 375                 380

Leu Thr Cys Leu Val Lys Gly Phe Tyr Pro Ser Asp Ile Ala Val Glu
     385                 390                 395                 400

Trp Glu Ser Asn Gly Gln Pro Glu Asn Asn Tyr Lys Thr Thr Pro Pro
                     405                 410                 415

Val Leu Asp Ser Asp Gly Ser Phe Phe Leu Tyr Ser Lys Leu Thr Val
                 420                 425                 430

Asp Lys Ser Arg Trp Gln Gln Gly Asn Val Phe Ser Cys Ser Val Met
             435                 440                 445

His Glu Ala Leu His Asn His Tyr Thr Gln Lys Ser Leu Ser Leu Ser
         450                 455                 460

Pro Gly Lys Ser Glu Lys Asp Glu Leu
     465                 470

<210> SEQ ID NO 8
<211> LENGTH: 696
<212> TYPE: DNA
<213> ORGANISM: Artificial sequence
<220> FEATURE:
<223> OTHER INFORMATION: IgG1-FC encoding sequence
```

<400> SEQUENCE: 8

```
gagccaaagt cttgcgataa gactcatact tgtccaccat gtccagctcc agaacttctt      60
ggaggaccat ctgttttcct tttcccacca aagccaaagg atactcttat gatttctagg     120
actccagagg ttacttgcgt tgttgttgat gtttcacatg aagatccaga ggtgaagttc     180
aattggtacg ttgatggagt tgaggttcat aatgctaaga ctaagccaag ggaggagcaa     240
tacaattcaa catacagggt tgtttctgtt cttactgttc ttcatcaaga ttggcttaat     300
ggaaaggaat acaagtgcaa ggtttctaat aaggctttgc cagcaccaat tgaaaagact     360
atttctaagg ctaagggaca accaagagag ccacaagttt acactcttcc accatctagg     420
gaggagatga ctaagaatca gtttctcttt acttgccttg ttaagggatt ctacccatct     480
gatattgctg ttgagtggga gtctaacgga cagcctgaga taattacaa gactactcca       540
ccagttcttg attctgatgg atctttcttc ctttactcta gttgactgt tgataagtct      600
aggtggcaac agggaaatgt tttctcttgc tctgttatgc atgaggctct tcataatcat     660
tacactcaga aatcactttc tctttctcca ggtaag                                696
```

<210> SEQ ID NO 9
<211> LENGTH: 232
<212> TYPE: PRT
<213> ORGANISM: Artificial sequence
<220> FEATURE:
<223> OTHER INFORMATION: IgG1-FC

<400> SEQUENCE: 9

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
```

225                    230

<210> SEQ ID NO 10
<211> LENGTH: 467
<212> TYPE: PRT
<213> ORGANISM: Artificial sequence
<220> FEATURE:
<223> OTHER INFORMATION: Etanercept polypeptide

<400> SEQUENCE: 10

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val

```
                355                 360                 365
Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 11
<211> LENGTH: 4
<212> TYPE: PRT
<213> ORGANISM: Artificial sequence
<220> FEATURE:
<223> OTHER INFORMATION: Amino acid sequence encoding  TNFR2 derived
      sequence

<400> SEQUENCE: 11

Leu Cys Ala Pro
1

<210> SEQ ID NO 12
<211> LENGTH: 4
<212> TYPE: PRT
<213> ORGANISM: Artificial sequence
<220> FEATURE:
<223> OTHER INFORMATION: Amino acid sequence encoding  TNFR2 derived
      sequence

<400> SEQUENCE: 12

Val Phe Cys Thr
1

<210> SEQ ID NO 13
<211> LENGTH: 18
<212> TYPE: PRT
<213> ORGANISM: Artificial sequence
<220> FEATURE:
<223> OTHER INFORMATION: Amino acid sequence encoding TNFR2 derived
      sequence
<220> FEATURE:
<221> NAME/KEY: misc_feature
<222> LOCATION: (8)..(8)
<223> OTHER INFORMATION: Xaa can be any naturally occurring amino acid

<400> SEQUENCE: 13

Leu Pro Ala Gln Val Ala Phe Xaa Pro Tyr Ala Pro Glu Pro Gly Ser
1               5                   10                  15

Thr Cys

<210> SEQ ID NO 14
<211> LENGTH: 4
<212> TYPE: PRT
<213> ORGANISM: Artificial sequence
<220> FEATURE:
<223> OTHER INFORMATION: ER retention signal peptide
```

```
<400> SEQUENCE: 14

His Asp Glu Leu
1

<210> SEQ ID NO 15
<211> LENGTH: 4
<212> TYPE: PRT
<213> ORGANISM: Artificial sequence
<220> FEATURE:
<223> OTHER INFORMATION: ER retention signal peptide

<400> SEQUENCE: 15

Lys Asp Glu Leu
1

<210> SEQ ID NO 16
<211> LENGTH: 6
<212> TYPE: PRT
<213> ORGANISM: Artificial sequence
<220> FEATURE:
<223> OTHER INFORMATION: ER retention signal peptide

<400> SEQUENCE: 16

Ser Glu Lys Asp Glu Leu
1               5

<210> SEQ ID NO 17
<211> LENGTH: 18
<212> TYPE: PRT
<213> ORGANISM: Artificial Sequence
<220> FEATURE:
<223> OTHER INFORMATION: Amino acid sequence encoding TNFR2 derived
      sequence

<400> SEQUENCE: 17

Leu Pro Ala Gln Val Ala Phe Thr Pro Tyr Ala Pro Glu Pro Gly Ser
1               5                   10                  15

Thr Cys

<210> SEQ ID NO 18
<211> LENGTH: 5
<212> TYPE: PRT
<213> ORGANISM: Artificial Sequence
<220> FEATURE:
<223> OTHER INFORMATION: Peptide degradation product derived from prh
      TNFR2:Fc (PRX106)

<400> SEQUENCE: 18

Leu Pro Ala Gln Val
1               5

<210> SEQ ID NO 19
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 19

Trp Gln Gln Gly Asn Val Phe Ser Cys Ser Val Met His Glu Ala Leu
1               5                   10                  15

His Asn His Tyr Thr Gln Lys
            20
```

```
<210> SEQ ID NO 20
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 20

Trp Gln Gln Gly Asn Val Phe Ser Cys Ser Val Met His Glu Ala Leu
1               5                   10                  15

His Asn His Tyr Thr Gln Lys
            20

<210> SEQ ID NO 21
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 21

Gly Phe Tyr Pro Ser Asp Ile Ala Val Glu Trp Glu Ser Asn Gly Gln
1               5                   10                  15

Pro Glu Asn Asn Tyr Lys Thr
            20

<210> SEQ ID NO 22
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 22

Gln Tyr Asn Ser Thr Tyr Arg Val Val Ser Val Leu Thr Val Leu His
1               5                   10                  15

Gln Asp Trp Leu Asn Gly Lys
            20

<210> SEQ ID NO 23
<211> LENGTH: 24
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 23

Trp Gln Gln Gly Asn Val Phe Ser Cys Ser Val Met His Glu Ala Leu
1               5                   10                  15

His Asn His Tyr Thr Gln Lys Ser
            20

<210> SEQ ID NO 24
<211> LENGTH: 20
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 24

Val Val Ser Val Leu Thr Val Leu His Gln Asp Trp Leu Asn Gly Lys
```

```
Glu Tyr Lys Cys
            20

<210> SEQ ID NO 25
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 25

Val Val Ser Val Leu Thr Val Leu His Gln Asp Trp Leu Asn Gly Lys
1               5                   10                  15

Glu Tyr Lys

<210> SEQ ID NO 26
<211> LENGTH: 37
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 26

Ser Gln His Thr Gln Pro Thr Pro Glu Pro Ser Thr Ala Pro Ser Thr
1               5                   10                  15

Ser Phe Leu Leu Pro Met Gly Pro Ser Pro Pro Ala Glu Gly Ser Thr
                20                  25                  30

Gly Asp Glu Pro Lys
            35

<210> SEQ ID NO 27
<211> LENGTH: 20
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 27

Trp Gln Gln Gly Asn Val Phe Ser Cys Ser Val Met His Glu Ala Leu
1               5                   10                  15

His Asn His Tyr
            20

<210> SEQ ID NO 28
<211> LENGTH: 31
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 28

Ser Cys Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp
                20                  25                  30

<210> SEQ ID NO 29
<211> LENGTH: 20
<212> TYPE: PRT
```

<213> ORGANISM: Artificial sequence
<220> FEATURE:
<223> OTHER INFORMATION: Peptide degradation product derived from prh
      TNFR2:Fc (PRX106)

<400> SEQUENCE: 29

Gly Gln Pro Arg Glu Pro Gln Val Tyr Thr Leu Pro Pro Ser Arg Glu
1               5                   10                  15

Glu Met Thr Lys
            20

<210> SEQ ID NO 30
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 30

Gly Phe Tyr Pro Ser Asp Ile Ala Val Glu Trp Glu Ser Asn Gly Gln
1               5                   10                  15

Pro Glu Asn Asn Tyr Lys Thr
            20

<210> SEQ ID NO 31
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 31

Leu Pro Ala Gln Val Ala Phe Thr Pro Tyr Ala Pro Glu Pro Gly Ser
1               5                   10                  15

Thr Cys Arg

<210> SEQ ID NO 32
<211> LENGTH: 10
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 32

Glu Ala Leu His Asn His Tyr Thr Gln Lys
1               5                   10

<210> SEQ ID NO 33
<211> LENGTH: 22
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 33

Gln Asn Arg Ile Cys Thr Cys Arg Pro Gly Trp Tyr Cys Ala Leu Ser
1               5                   10                  15

Lys Gln Glu Gly Cys Arg
            20

<210> SEQ ID NO 34

```
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 34

Trp Gln Gln Gly Asn Val Phe Ser Cys Ser Val Met His Glu Ala Leu
1               5                   10                  15

His Asn His Tyr Thr Gln Lys
            20

<210> SEQ ID NO 35
<211> LENGTH: 37
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 35

Ser Gln His Thr Gln Pro Thr Pro Glu Pro Ser Thr Ala Pro Ser Thr
1               5                   10                  15

Ser Phe Leu Leu Pro Met Gly Pro Ser Pro Pro Ala Glu Gly Ser Thr
            20                  25                  30

Gly Asp Glu Pro Lys
        35

<210> SEQ ID NO 36
<211> LENGTH: 20
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 36

Gly Gln Pro Arg Glu Pro Gln Val Tyr Thr Leu Pro Pro Ser Arg Glu
1               5                   10                  15

Glu Met Thr Lys
            20

<210> SEQ ID NO 37
<211> LENGTH: 22
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 37

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 38
<211> LENGTH: 37
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 38
```

```
Ser Gln His Thr Gln Pro Thr Pro Glu Pro Ser Thr Ala Pro Ser Thr
1               5                   10                  15

Ser Phe Leu Leu Pro Met Gly Pro Ser Pro Pro Ala Glu Gly Ser Thr
                20                  25                  30

Gly Asp Glu Pro Lys
        35

<210> SEQ ID NO 39
<211> LENGTH: 16
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 39

Val Val Ser Val Leu Thr Val Leu His Gln Asp Trp Leu Asn Gly Lys
1               5                   10                  15

<210> SEQ ID NO 40
<211> LENGTH: 31
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 40

Thr Tyr Thr Gln Leu Trp Asn Trp Val Pro Glu Cys Leu Ser Cys Gly
1               5                   10                  15

Ser Arg Cys Ser Ser Asp Gln Val Glu Thr Gln Ala Cys Thr Arg
                20                  25                  30

<210> SEQ ID NO 41
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 41

Trp Gln Gln Gly Asn Val Phe Ser Cys Ser Val Met His Glu Ala Leu
1               5                   10                  15

His Asn His Tyr Thr Gln Lys
                20

<210> SEQ ID NO 42
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 42

Gly Phe Tyr Pro Ser Asp Ile Ala Val Glu Trp Glu Ser Asn Gly Gln
1               5                   10                  15

Pro Glu Asn Asn Tyr Lys Thr
                20

<210> SEQ ID NO 43
<211> LENGTH: 13
<212> TYPE: PRT
```

```
<213> ORGANISM: Artificial sequence
<220> FEATURE:
<223> OTHER INFORMATION: Peptide degradation product derived from prh
      TNFR2:Fc (PRX106)

<400> SEQUENCE: 43

Val Val Val Asp Val Ser His Glu Asp Pro Glu Val Lys
1               5                   10

<210> SEQ ID NO 44
<211> LENGTH: 24
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 44

Pro Ser Thr Ser Phe Leu Leu Pro Met Gly Pro Ser Pro Pro Ala Glu
1               5                   10                  15

Gly Ser Thr Gly Asp Glu Pro Lys
            20

<210> SEQ ID NO 45
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 45

Leu Pro Ala Gln Val Ala Phe Thr Pro Tyr Ala Pro Glu Pro Gly Ser
1               5                   10                  15

Thr Cys Arg

<210> SEQ ID NO 46
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 46

Thr Thr Pro Pro Val Leu Asp Ser Asp Gly Ser Phe Phe Leu
1               5                   10

<210> SEQ ID NO 47
<211> LENGTH: 7
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 47

Leu Ser Leu Ser Pro Gly Lys
1               5

<210> SEQ ID NO 48
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)
```

```
<400> SEQUENCE: 48

Glu Pro Gln Val Tyr Thr Leu Pro Pro Ser Arg Glu Glu Met Thr Lys
1               5                   10                  15

Asn

<210> SEQ ID NO 49
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 49

Ser Met Ala Pro Gly Ala Val His Leu Pro Gln
1               5                   10

<210> SEQ ID NO 50
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 50

Thr Thr Pro Pro Val Leu Asp Ser Asp Gly Ser Phe Phe Leu Tyr Ser
1               5                   10                  15

Lys

<210> SEQ ID NO 51
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 51

Trp Gln Gln Gly Asn Val Phe Ser Cys Ser Val Met His Glu Ala Leu
1               5                   10                  15

His Asn His Tyr Thr Gln Lys
            20

<210> SEQ ID NO 52
<211> LENGTH: 8
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 52

Ser Met Ala Pro Gly Ala Val His
1               5

<210> SEQ ID NO 53
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 53
```

```
Ser Val Met His Glu Ala Leu His Asn His Tyr Thr Gln Lys
1               5                   10
```

```
<210> SEQ ID NO 54
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 54

Val Val Ser Val Leu Thr Val Leu His
1               5
```

```
<210> SEQ ID NO 55
<211> LENGTH: 37
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 55

Ser Gln His Thr Gln Pro Thr Pro Glu Pro Ser Thr Ala Pro Ser Thr
1               5                   10                  15

Ser Phe Leu Leu Pro Met Gly Pro Ser Pro Pro Ala Glu Gly Ser Thr
            20                  25                  30

Gly Asp Glu Pro Lys
        35
```

```
<210> SEQ ID NO 56
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 56

Gly Gln Pro Arg Glu Pro Gln Val Tyr
1               5
```

```
<210> SEQ ID NO 57
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 57

Ala Gln Val Ala Phe Thr Pro Tyr Ala Pro Glu Pro Gly Ser Thr Cys
1               5                   10                  15

Arg
```

```
<210> SEQ ID NO 58
<211> LENGTH: 6
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 58
```

```
Cys Ala Pro Leu Arg Lys
1               5

<210> SEQ ID NO 59
<211> LENGTH: 26
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 59

Glu Pro Gln Val Tyr Thr Leu Pro Pro Ser Arg Glu Glu Met Thr Lys
1               5                   10                  15

Asn Gln Val Ser Leu Thr Cys Leu Val Lys
            20                  25

<210> SEQ ID NO 60
<211> LENGTH: 8
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 60

Ser Met Ala Pro Gly Ala Val His
1               5

<210> SEQ ID NO 61
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 61

Val Val Ser Val Leu Thr Val Leu His Gln Asp
1               5                   10

<210> SEQ ID NO 62
<211> LENGTH: 7
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 62

Leu Phe Pro Pro Lys Pro Lys
1               5

<210> SEQ ID NO 63
<211> LENGTH: 8
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 63

Gly Ser Phe Phe Leu Tyr Ser Lys
1               5

<210> SEQ ID NO 64
<211> LENGTH: 9
```

-continued

```
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 64

Ile Cys Thr Cys Arg Pro Gly Trp Tyr
1               5

<210> SEQ ID NO 65
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 65

Ser Gln His Thr Gln Pro Thr Pro Glu Pro Ser
1               5                   10

<210> SEQ ID NO 66
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 66

Ser Val Leu Thr Val Leu His Gln Asp Trp Leu Asn Gly Lys Glu Tyr
1               5                   10                  15

Lys

<210> SEQ ID NO 67
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 67

Gln Val Glu Thr Gln Ala Cys Thr Arg
1               5

<210> SEQ ID NO 68
<211> LENGTH: 8
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 68

Ser Leu Ser Leu Ser Pro Gly Lys
1               5

<210> SEQ ID NO 69
<211> LENGTH: 10
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 69
```

```
Ser Asp Gly Ser Phe Phe Leu Tyr Ser Lys
1               5                   10

<210> SEQ ID NO 70
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 70

Lys Ala Leu Pro Ala Pro Ile Glu Lys
1               5

<210> SEQ ID NO 71
<211> LENGTH: 8
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 71

Ala Leu Pro Ala Pro Ile Glu Lys
1               5

<210> SEQ ID NO 72
<211> LENGTH: 10
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 72

Ala Val Cys Thr Ser Thr Ser Pro Thr Arg
1               5                   10

<210> SEQ ID NO 73
<211> LENGTH: 18
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 73

Ser Gln His Thr Gln Pro Thr Pro Glu Pro Ser Thr Ala Pro Ser Thr
1               5                   10                  15

Ser Phe

<210> SEQ ID NO 74
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 74

Gln Val Ser Leu Thr Cys Leu Val Lys
1               5

<210> SEQ ID NO 75
<211> LENGTH: 23
```

```
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 75

Leu Arg Glu Tyr Tyr Asp Gln Thr Ala Gln Met Cys Cys Ser Lys Cys
1               5                   10                  15

Ser Pro Gly Gln His Ala Lys
            20

<210> SEQ ID NO 76
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 76

Trp Gln Gln Gly Asn Val Phe Ser Cys Ser Val Met His Glu Ala Leu
1               5                   10                  15

His

<210> SEQ ID NO 77
<211> LENGTH: 7
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 77

Asp Thr Leu Met Ile Ser Arg
1               5

<210> SEQ ID NO 78
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 78

Pro Met Gly Pro Ser Pro Pro Ala Glu Gly Ser Thr Gly Asp Glu Pro
1               5                   10                  15

Lys

<210> SEQ ID NO 79
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 79

Thr His Thr Cys Pro Pro Cys Pro Ala Pro Glu Leu Leu Gly Gly Pro
1               5                   10                  15

Ser Val Phe

<210> SEQ ID NO 80
<211> LENGTH: 7
```

```
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 80

Asp Thr Leu Met Ile Ser Arg
1               5

<210> SEQ ID NO 81
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 81

Ser Asp Gln Val Glu Thr Gln Ala Cys Thr Arg
1               5                   10

<210> SEQ ID NO 82
<211> LENGTH: 10
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 82

Lys Cys Arg Pro Gly Phe Gly Val Ala Arg
1               5                   10

<210> SEQ ID NO 83
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 83

Trp Tyr Val Asp Gly Val Glu Val His Asn Ala Lys
1               5                   10

<210> SEQ ID NO 84
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 84

Tyr Val Asp Gly Val Glu Val His Asn Ala Lys
1               5                   10

<210> SEQ ID NO 85
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 85

Thr Thr Pro Pro Val Leu Asp Ser Asp Gly Ser Phe Phe
```

<210> SEQ ID NO 86
<211> LENGTH: 26
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 86

Thr His Thr Cys Pro Pro Cys Pro Ala Pro Glu Leu Leu Gly Gly Pro
1               5                   10                  15

Ser Val Phe Leu Phe Pro Pro Lys Pro Lys
            20                  25

<210> SEQ ID NO 87
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 87

Pro Ser Pro Pro Ala Glu Gly Ser Thr Gly Asp Glu Pro Lys
1               5                   10

<210> SEQ ID NO 88
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 88

Ser Leu Ser Leu Ser Pro Gly Lys Ser Glu Lys Asp
1               5                   10

<210> SEQ ID NO 89
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 89

Met Ala Pro Gly Ala Val His Leu Pro Gln Pro Val Ser Thr Arg
1               5                   10                  15

<210> SEQ ID NO 90
<211> LENGTH: 10
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 90

Val Asp Gly Val Glu Val His Asn Ala Lys
1               5                   10

<210> SEQ ID NO 91
<211> LENGTH: 23
<212> TYPE: PRT

<213> ORGANISM: Artificial sequence
<220> FEATURE:
<223> OTHER INFORMATION: Peptide degradation product derived from prh
      TNFR2:Fc (PRX106)

<400> SEQUENCE: 91

Ser Cys Asp Lys Thr His Thr Cys Pro Pro Cys Pro Ala Pro Glu Leu
1               5                   10                  15

Leu Gly Gly Pro Ser Val Phe
            20

<210> SEQ ID NO 92
<211> LENGTH: 16
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 92

Val Val Ser Val Leu Thr Val Leu His Gln Asp Trp Leu Asn Gly Lys
1               5                   10                  15

<210> SEQ ID NO 93
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 93

Ser Leu Ser Leu Ser Pro Gly Lys Ser Glu Lys
1               5                   10

<210> SEQ ID NO 94
<211> LENGTH: 22
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 94

Pro Pro Cys Pro Ala Pro Glu Leu Leu Gly Gly Pro Ser Val Phe Leu
1               5                   10                  15

Phe Pro Pro Lys Pro Lys
            20

<210> SEQ ID NO 95
<211> LENGTH: 7
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 95

Ser Phe Phe Leu Tyr Ser Lys
1               5

<210> SEQ ID NO 96
<211> LENGTH: 14
<212> TYPE: PRT
<213> ORGANISM: Artificial sequence
<220> FEATURE:
<223> OTHER INFORMATION: Peptide degradation product derived from prh TNFR2:Fc (PRX106)

<400> SEQUENCE: 96

Phe Asn Trp Tyr Val Asp Gly Val Glu Val His Asn Ala Lys
1               5                   10

<210> SEQ ID NO 97
<211> LENGTH: 20
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 97

Phe Leu Leu Pro Met Gly Pro Ser Pro Pro Ala Glu Gly Ser Thr Gly
1               5                   10                  15

Asp Glu Pro Lys
            20

<210> SEQ ID NO 98
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 98

Asp Ala Val Cys Thr Ser Thr Ser Pro Thr Arg
1               5                   10

<210> SEQ ID NO 99
<211> LENGTH: 10
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 99

Asn Gln Val Ser Leu Thr Cys Leu Val Lys
1               5                   10

<210> SEQ ID NO 100
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 100

Asn Gln Val Ser Leu Thr Cys Leu Val Lys Gly
1               5                   10

<210> SEQ ID NO 101
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 101

Ser Leu Ser Pro Gly Lys Ser Glu Lys
1               5

<210> SEQ ID NO 102
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 102

Thr Pro Glu Val Thr Cys Val Val Val Asp Val Ser His Glu Asp Pro
1               5                   10                  15

Glu Val Lys

<210> SEQ ID NO 103
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 103

Leu Arg Glu Tyr Tyr Asp Gln Thr Ala Gln Met
1               5                   10

<210> SEQ ID NO 104
<211> LENGTH: 22
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 104

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 105
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 105

Phe Asn Trp Tyr Val Asp Gly Val Glu Val His Asn
1               5                   10

<210> SEQ ID NO 106
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 106

Val Val Ser Val Leu Thr Val Leu His Gln Asp Trp Leu Asn
1               5                   10

<210> SEQ ID NO 107
<211> LENGTH: 16

```
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 107

Ser Gln His Thr Gln Pro Thr Pro Glu Pro Ser Thr Ala Pro Ser Thr
1               5                   10                  15

<210> SEQ ID NO 108
<211> LENGTH: 20
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 108

Arg Thr Pro Glu Val Thr Cys Val Val Val Asp Val Ser His Glu Asp
1               5                   10                  15

Pro Glu Val Lys
            20

<210> SEQ ID NO 109
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 109

Ser Leu Ser Leu Ser Pro Gly Lys Ser
1               5

<210> SEQ ID NO 110
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 110

Leu Ser Pro Gly Lys Ser Glu Lys Asp Glu Leu
1               5                   10

<210> SEQ ID NO 111
<211> LENGTH: 8
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 111

Leu Pro Gln Pro Val Ser Thr Arg
1               5

<210> SEQ ID NO 112
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)
```

<400> SEQUENCE: 112

Thr Thr Pro Pro Val Leu Asp Ser Asp Gly Ser Phe Phe Leu Tyr
1               5                   10                  15

<210> SEQ ID NO 113
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 113

Thr Ser Asp Thr Val Cys Asp Ser Cys Glu Asp Ser Thr Tyr Thr Gln
1               5                   10                  15

Leu Trp Asn

<210> SEQ ID NO 114
<211> LENGTH: 20
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 114

Ala Leu Pro Ala Gln Val Ala Phe Thr Pro Tyr Ala Pro Glu Pro Gly
1               5                   10                  15

Ser Thr Cys Arg
            20

<210> SEQ ID NO 115
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 115

Glu Glu Gln Tyr Asn Ser Thr Tyr Arg
1               5

<210> SEQ ID NO 116
<211> LENGTH: 30
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 116

Ser Cys Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys
            20                  25                  30

<210> SEQ ID NO 117
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 117

```
Cys Ser Pro Gly Gln His Ala Lys Val Phe Cys Thr Lys
1               5                   10
```

```
<210> SEQ ID NO 118
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 118
```

```
Thr Pro Glu Val Thr Cys Val Val Val Asp Val Ser His Glu Asp
1               5                   10                  15
```

```
<210> SEQ ID NO 119
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 119
```

```
Ser Met Ala Pro Gly Ala Val His Leu Pro Gln Pro Val
1               5                   10
```

```
<210> SEQ ID NO 120
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 120
```

```
Thr Cys Arg Pro Gly Trp Tyr Cys Ala Leu Ser Lys
1               5                   10
```

```
<210> SEQ ID NO 121
<211> LENGTH: 24
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 121
```

```
Thr Cys Pro Pro Cys Pro Ala Pro Glu Leu Leu Gly Gly Pro Ser Val
1               5                   10                  15

Phe Leu Phe Pro Pro Lys Pro Lys
                20
```

```
<210> SEQ ID NO 122
<211> LENGTH: 30
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 122
```

```
Thr Ser Asp Thr Val Cys Asp Ser Cys Glu Asp Ser Thr Tyr Thr Gln
1               5                   10                  15

Leu Trp Asn Trp Val Pro Glu Cys Leu Ser Cys Gly Ser Arg
                20                  25                  30
```

<210> SEQ ID NO 123
<211> LENGTH: 7
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 123

Leu Cys Ala Pro Leu Arg Lys
1               5

<210> SEQ ID NO 124
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 124

Ser Pro Pro Ala Glu Gly Ser Thr Gly Asp Glu Pro Lys
1               5                   10

<210> SEQ ID NO 125
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 125

Trp Val Pro Glu Cys Leu Ser Cys Gly Ser Arg
1               5                   10

<210> SEQ ID NO 126
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 126

Gly Pro Ser Pro Pro Ala Glu Gly Ser Thr Gly Asp Glu Pro Lys
1               5                   10                  15

<210> SEQ ID NO 127
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 127

Ser Ser Asp Gln Val Glu Thr Gln Ala Cys Thr Arg
1               5                   10

<210> SEQ ID NO 128
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

```
<400> SEQUENCE: 128

Glu Glu Gln Tyr Asn Ser Thr Tyr Arg
1               5

<210> SEQ ID NO 129
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 129

Val Ala Phe Thr Pro Tyr Ala Pro Glu Pro Gly Ser Thr Cys Arg
1               5                   10                  15

<210> SEQ ID NO 130
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 130

Pro Gly Trp Tyr Cys Ala Leu Ser Lys
1               5

<210> SEQ ID NO 131
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 131

Cys Arg Pro Gly Phe Gly Val Ala Arg
1               5

<210> SEQ ID NO 132
<211> LENGTH: 16
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 132

Ser Cys Ser Val Met His Glu Ala Leu His Asn His Tyr Thr Gln Lys
1               5                   10                  15

<210> SEQ ID NO 133
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 133

Val Val Ser Val Leu Thr Val Leu His Gln Asp Trp Leu Asn Gly Lys
1               5                   10                  15

Glu Tyr Lys
```

```
<210> SEQ ID NO 134
<211> LENGTH: 6
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 134

Leu Cys Ala Pro Leu Arg
1               5

<210> SEQ ID NO 135
<211> LENGTH: 26
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 135

Glu Pro Gln Val Tyr Thr Leu Pro Pro Ser Arg Glu Glu Met Thr Lys
1               5                   10                  15

Asn Gln Val Ser Leu Thr Cys Leu Val Lys
            20                  25

<210> SEQ ID NO 136
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 136

Leu Leu Pro Met Gly Pro Ser Pro Pro Ala Glu Gly Ser Thr Gly Asp
1               5                   10                  15

Glu Pro Lys

<210> SEQ ID NO 137
<211> LENGTH: 37
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 137

Ser Gln His Thr Gln Pro Thr Pro Glu Pro Ser Thr Ala Pro Ser Thr
1               5                   10                  15

Ser Phe Leu Leu Pro Met Gly Pro Ser Pro Pro Ala Glu Gly Ser Thr
            20                  25                  30

Gly Asp Glu Pro Lys
            35

<210> SEQ ID NO 138
<211> LENGTH: 10
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 138

Ser Leu Ser Leu Ser Pro Gly Lys Ser Glu
1               5                   10
```

<210> SEQ ID NO 139
<211> LENGTH: 8
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 139

Glu Glu Met Thr Lys Asn Gln Val
1               5

<210> SEQ ID NO 140
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 140

Ser Val Met His Glu Ala Leu His Asn His Tyr Thr Gln Lys
1               5                   10

<210> SEQ ID NO 141
<211> LENGTH: 41
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 141

Ser Gln His Thr Gln Pro Thr Pro Glu Pro Ser Thr Ala Pro Ser Thr
1               5                   10                  15

Ser Phe Leu Leu Pro Met Gly Pro Ser Pro Pro Ala Glu Gly Ser Thr
                20                  25                  30

Gly Asp Glu Pro Lys Ser Cys Asp Lys
            35                  40

<210> SEQ ID NO 142
<211> LENGTH: 16
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 142

Glu Glu Met Thr Lys Asn Gln Val Ser Leu Thr Cys Leu Val Lys Gly
1               5                   10                  15

<210> SEQ ID NO 143
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 143

Leu Arg Glu Tyr Tyr Asp Gln Thr Ala Gln Met Cys Cys Ser Lys
1               5                   10                  15

<210> SEQ ID NO 144

```
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 144

Cys Ser Ser Asp Gln Val Glu Thr Gln Ala Cys Thr Arg
1               5                   10

<210> SEQ ID NO 145
<211> LENGTH: 16
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 145

Glu Pro Gln Val Tyr Thr Leu Pro Pro Ser Arg Glu Glu Met Thr Lys
1               5                   10                  15

<210> SEQ ID NO 146
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 146

Asn Gln Val Ser Leu Thr Cys Leu Val Lys Gly
1               5                   10

<210> SEQ ID NO 147
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 147

Cys Ser Ser Asp Gln Val Glu Thr Gln Ala Cys Thr Arg
1               5                   10

<210> SEQ ID NO 148
<211> LENGTH: 10
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 148

Asn Gln Val Ser Leu Thr Cys Leu Val Lys
1               5                   10

<210> SEQ ID NO 149
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 149
```

```
Thr Lys Pro Arg Glu Glu Gln Tyr Asn Ser Thr Tyr Arg
1               5                   10

<210> SEQ ID NO 150
<211> LENGTH: 18
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 150

Pro Ala Gln Val Ala Phe Thr Pro Tyr Ala Pro Glu Pro Gly Ser Thr
1               5                   10                  15

Cys Arg

<210> SEQ ID NO 151
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 151

Ser Leu Ser Leu Ser Pro Gly Lys Ser Glu Lys Asp Glu Leu
1               5                   10

<210> SEQ ID NO 152
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 152

Ala Phe Thr Pro Tyr Ala Pro Glu Pro Gly Ser Thr Cys Arg
1               5                   10

<210> SEQ ID NO 153
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 153

Ala Pro Gly Ala Val His Leu Pro Gln Pro Val Ser Thr Arg
1               5                   10

<210> SEQ ID NO 154
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 154

Ser Asp Gly Ser Phe Phe Leu Tyr Ser Lys Leu Thr Val Asp Lys
1               5                   10                  15

<210> SEQ ID NO 155
<211> LENGTH: 14
<212> TYPE: PRT
```

```
<213> ORGANISM: Artificial sequence
<220> FEATURE:
<223> OTHER INFORMATION: Peptide degradation product derived from prh
      TNFR2:Fc (PRX106)

<400> SEQUENCE: 155

Thr His Thr Cys Pro Pro Cys Pro Ala Pro Glu Leu Leu Gly
1               5                   10

<210> SEQ ID NO 156
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 156

Val Val Ser Val Leu Thr Val Leu His Gln Asp Trp Leu Asn
1               5                   10

<210> SEQ ID NO 157
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 157

Glu Pro Gln Val Tyr Thr Leu Pro Pro Ser Arg
1               5                   10

<210> SEQ ID NO 158
<211> LENGTH: 16
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 158

Ser Met Ala Pro Gly Ala Val His Leu Pro Gln Pro Val Ser Thr Arg
1               5                   10                  15

<210> SEQ ID NO 159
<211> LENGTH: 20
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 159

Gly Gln Pro Arg Glu Pro Gln Val Tyr Thr Leu Pro Pro Ser Arg Glu
1               5                   10                  15

Glu Met Thr Lys
            20

<210> SEQ ID NO 160
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 160
```

```
Thr Pro Tyr Ala Pro Glu Pro Gly Ser Thr Cys Arg
1               5                   10
```

```
<210> SEQ ID NO 161
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 161

Glu Val Thr Cys Val Val Val Asp Val Ser His Glu Asp Pro Glu Val
1               5                   10                  15
Lys
```

```
<210> SEQ ID NO 162
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 162

Thr Lys Pro Arg Glu Glu Gln Tyr Asn Ser Thr Tyr Arg
1               5                   10
```

```
<210> SEQ ID NO 163
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 163

Val Ser Asn Lys Ala Leu Pro Ala Pro Ile Glu Lys
1               5                   10
```

```
<210> SEQ ID NO 164
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 164

Leu Arg Glu Tyr Tyr Asp Gln Thr Ala Gln Met Cys Cys Ser Lys
1               5                   10                  15
```

```
<210> SEQ ID NO 165
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 165

Phe Thr Pro Tyr Ala Pro Glu Pro Gly Ser Thr Cys Arg
1               5                   10
```

```
<210> SEQ ID NO 166
<211> LENGTH: 16
```

```
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 166

Ser Met Ala Pro Gly Ala Val His Leu Pro Gln Pro Val Ser Thr Arg
1               5                   10                  15

<210> SEQ ID NO 167
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 167

Gly Pro Ser Val Phe Leu Phe Pro Pro Lys Pro Lys
1               5                   10

<210> SEQ ID NO 168
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 168

Val Val Ser Val Leu Thr Val Leu His Gln Asp Trp Leu Asn Gly Lys
1               5                   10                  15

Glu Tyr Lys

<210> SEQ ID NO 169
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 169

Ser Gln His Thr Gln Pro Thr Pro Glu Pro Ser Thr Ala Pro Ser
1               5                   10                  15

<210> SEQ ID NO 170
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 170

Ser Met Ala Pro Gly Ala Val His Leu Pro Gln Pro Val Ser
1               5                   10

<210> SEQ ID NO 171
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 171
```

```
Ala Val His Leu Pro Gln Pro Val Ser Thr Arg
1               5                   10

<210> SEQ ID NO 172
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 172

Gly Gln Pro Arg Glu Pro Gln Val Tyr Thr Leu Pro Pro Ser Arg
1               5                   10                  15

<210> SEQ ID NO 173
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 173

Pro Gly Ala Val His Leu Pro Gln Pro Val Ser Thr Arg
1               5                   10

<210> SEQ ID NO 174
<211> LENGTH: 6
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 174

Thr Leu Met Ile Ser Arg
1               5

<210> SEQ ID NO 175
<211> LENGTH: 33
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 175

Lys Asn Gln Val Ser Leu Thr Cys Leu Val Lys Gly Phe Tyr Pro Ser
1               5                   10                  15

Asp Ile Ala Val Glu Trp Glu Ser Asn Gly Gln Pro Glu Asn Asn Tyr
            20                  25                  30

Lys

<210> SEQ ID NO 176
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 176

Leu Arg Glu Tyr Tyr Asp Gln Thr Ala Gln Met Cys
1               5                   10
```

<210> SEQ ID NO 177
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 177

Ser Met Ala Pro Gly Ala Val His Leu Pro Gln Pro Val
1               5                   10

<210> SEQ ID NO 178
<211> LENGTH: 7
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 178

Leu Pro Ala Pro Ile Glu Lys
1               5

<210> SEQ ID NO 179
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 179

Glu Tyr Tyr Asp Gln Thr Ala Gln Met Cys Cys Ser Lys
1               5                   10

<210> SEQ ID NO 180
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 180

Asn Trp Val Pro Glu Cys Leu Ser Cys Gly Ser Arg
1               5                   10

<210> SEQ ID NO 181
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 181

Ser Leu Ser Pro Gly Lys Ser Glu Lys Asp Glu Leu
1               5                   10

<210> SEQ ID NO 182
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

```
<400> SEQUENCE: 182

Ile Cys Thr Cys Arg Pro Gly Trp Tyr Cys Ala Leu Ser Lys
1               5                   10

<210> SEQ ID NO 183
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 183

Ser Met Ala Pro Gly Ala Val His Leu Pro Gln Pro Val Ser Thr
1               5                   10                  15

<210> SEQ ID NO 184
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 184

Glu Tyr Tyr Asp Gln Thr Ala Gln Met Cys Cys Ser Lys
1               5                   10

<210> SEQ ID NO 185
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 185

Ala Ser Met Asp Ala Val Cys Thr Ser Thr Ser Pro Thr Arg
1               5                   10

<210> SEQ ID NO 186
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 186

Ser Gln His Thr Gln Pro Thr Pro Glu Pro Ser Thr Ala Pro Ser Thr
1               5                   10                  15

Ser

<210> SEQ ID NO 187
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 187

Thr Leu Pro Pro Ser Arg Glu Glu Met Thr Lys
1               5                   10

<210> SEQ ID NO 188
```

```
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 188

Ser Gln His Thr Gln Pro Thr Pro Glu Pro Ser Thr Ala Pro Ser Thr
1               5                   10                  15

Ser Phe Leu

<210> SEQ ID NO 189
<211> LENGTH: 6
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 189

Thr Leu Met Ile Ser Arg
1               5

<210> SEQ ID NO 190
<211> LENGTH: 16
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 190

Glu Pro Gln Val Tyr Thr Leu Pro Pro Ser Arg Glu Glu Met Thr Lys
1               5                   10                  15

<210> SEQ ID NO 191
<211> LENGTH: 20
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 191

Gly Gln Pro Arg Glu Pro Gln Val Tyr Thr Leu Pro Pro Ser Arg Glu
1               5                   10                  15

Glu Met Thr Lys
            20

<210> SEQ ID NO 192
<211> LENGTH: 21
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 192

Thr Pro Glu Val Thr Cys Val Val Val Asp Val Ser His Glu Asp Pro
1               5                   10                  15

Glu Val Lys Phe Asn
            20

<210> SEQ ID NO 193
<211> LENGTH: 18
```

<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 193

Ser Cys Asp Lys Thr His Thr Cys Pro Pro Cys Pro Ala Pro Glu Leu
1               5                   10                  15

Leu Gly

<210> SEQ ID NO 194
<211> LENGTH: 22
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 194

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 195
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 195

Ala Lys Gly Gln Pro Arg Glu Pro Gln Val Tyr Thr Leu Pro Pro Ser
1               5                   10                  15

Arg

<210> SEQ ID NO 196
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 196

Leu Arg Glu Tyr Tyr Asp Gln Thr Ala Gln Met Cys Cys
1               5                   10

<210> SEQ ID NO 197
<211> LENGTH: 18
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 197

Leu Pro Met Gly Pro Ser Pro Pro Ala Glu Gly Ser Thr Gly Asp Glu
1               5                   10                  15

Pro Lys

<210> SEQ ID NO 198
<211> LENGTH: 16

```
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 198

Ser Cys Ser Val Met His Glu Ala Leu His Asn His Tyr Thr Gln Lys
1               5                   10                  15

<210> SEQ ID NO 199
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 199

Phe Asn Trp Tyr Val Asp Gly Val Glu Val His Asn Ala Lys
1               5                   10

<210> SEQ ID NO 200
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 200

Pro Met Gly Pro Ser Pro Pro Ala Glu Gly Ser Thr Gly Asp Glu Pro
1               5                   10                  15

Lys

<210> SEQ ID NO 201
<211> LENGTH: 16
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 201

Ser Met Ala Pro Gly Ala Val His Leu Pro Gln Pro Val Ser Thr Arg
1               5                   10                  15

<210> SEQ ID NO 202
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 202

Ser Met Ala Pro Gly Ala Val His Leu Pro Gln
1               5                   10

<210> SEQ ID NO 203
<211> LENGTH: 18
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 203
```

```
Leu Pro Met Gly Pro Ser Pro Ala Glu Gly Ser Thr Gly Asp Glu
1               5                   10                  15

Pro Lys

<210> SEQ ID NO 204
<211> LENGTH: 474
<212> TYPE: PRT
<213> ORGANISM: Artificial Sequence
<220> FEATURE:
<223> OTHER INFORMATION: PRX106

<400> SEQUENCE: 204

Ala Leu Pro Ala Gln Val Ala Phe Thr Pro Tyr Ala Pro Glu Pro Gly
1               5                   10                  15

Ser Thr Cys Arg Leu Arg Glu Tyr Tyr Asp Gln Thr Ala Gln Met Cys
            20                  25                  30

Cys Ser Lys Cys Ser Pro Gly Gln His Ala Lys Val Phe Cys Thr Lys
        35                  40                  45

Thr Ser Asp Thr Val Cys Asp Ser Cys Glu Asp Ser Thr Tyr Thr Gln
    50                  55                  60

Leu Trp Asn Trp Val Pro Glu Cys Leu Ser Cys Gly Ser Arg Cys Ser
65                  70                  75                  80

Ser Asp Gln Val Glu Thr Gln Ala Cys Thr Arg Glu Gln Asn Arg Ile
                85                  90                  95

Cys Thr Cys Arg Pro Gly Trp Tyr Cys Ala Leu Ser Lys Gln Glu Gly
            100                 105                 110

Cys Arg Leu Cys Ala Pro Leu Arg Lys Cys Arg Pro Gly Phe Gly Val
        115                 120                 125

Ala Arg Pro Gly Thr Glu Thr Ser Asp Val Val Cys Lys Pro Cys Ala
    130                 135                 140

Pro Gly Thr Phe Ser Asn Thr Thr Ser Ser Thr Asp Ile Cys Arg Pro
145                 150                 155                 160

His Gln Ile Cys Asn Val Val Ala Ile Pro Gly Asn Ala Ser Met Asp
                165                 170                 175

Ala Val Cys Thr Ser Thr Ser Pro Thr Arg Ser Met Ala Pro Gly Ala
            180                 185                 190

Val His Leu Pro Gln Pro Val Ser Thr Arg Ser Gln His Thr Gln Pro
        195                 200                 205

Thr Pro Glu Pro Ser Thr Ala Pro Ser Thr Ser Phe Leu Leu Pro Met
    210                 215                 220

Gly Pro Ser Pro Pro Ala Glu Gly Ser Thr Gly Asp Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335
```

```
Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
                355                 360                 365

Val Tyr Thr Leu Pro Pro Ser Arg Glu Glu Met Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
                435                 440                 445

Met His Glu Ala Leu His Asn His Tyr Thr Gln Lys Ser Leu Ser Leu
                450                 455                 460

Ser Pro Gly Lys Ser Glu Lys Asp Glu Leu
465                 470

<210> SEQ ID NO 205
<211> LENGTH: 472
<212> TYPE: PRT
<213> ORGANISM: Artificial Sequence
<220> FEATURE:
<223> OTHER INFORMATION: PRX106

<400> SEQUENCE: 205

Pro Ala Gln Val Ala Phe Thr Pro Tyr Ala Pro Glu Pro Gly Ser Thr
1               5                   10                  15

Cys Arg Leu Arg Glu Tyr Tyr Asp Gln Thr Ala Gln Met Cys Cys Ser
                20                  25                  30

Lys Cys Ser Pro Gly Gln His Ala Lys Val Phe Cys Thr Lys Thr Ser
                35                  40                  45

Asp Thr Val Cys Asp Ser Cys Glu Asp Ser Thr Tyr Thr Gln Leu Trp
            50                  55                  60

Asn Trp Val Pro Glu Cys Leu Ser Cys Gly Ser Arg Cys Ser Ser Asp
65                  70                  75                  80

Gln Val Glu Thr Gln Ala Cys Thr Arg Glu Gln Asn Arg Ile Cys Thr
                85                  90                  95

Cys Arg Pro Gly Trp Tyr Cys Ala Leu Ser Lys Gln Glu Gly Cys Arg
                100                 105                 110

Leu Cys Ala Pro Leu Arg Lys Cys Arg Pro Gly Phe Gly Val Ala Arg
            115                 120                 125

Pro Gly Thr Glu Thr Ser Asp Val Val Cys Lys Pro Cys Ala Pro Gly
            130                 135                 140

Thr Phe Ser Asn Thr Thr Ser Ser Thr Asp Ile Cys Arg Pro His Gln
145                 150                 155                 160

Ile Cys Asn Val Val Ala Ile Pro Gly Asn Ala Ser Met Asp Ala Val
                165                 170                 175

Cys Thr Ser Thr Ser Pro Thr Arg Ser Met Ala Pro Gly Ala Val His
                180                 185                 190

Leu Pro Gln Pro Val Ser Thr Arg Ser Gln His Thr Gln Pro Thr Pro
            195                 200                 205

Glu Pro Ser Thr Ala Pro Ser Thr Ser Phe Leu Leu Pro Met Gly Pro
            210                 215                 220
```

-continued

```
Ser Pro Pro Ala Glu Gly Ser Thr Gly Asp Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys Ser Glu Lys Asp Glu Leu
465                 470
```